United States Patent
Campisi et al.

(10) Patent No.: US 9,884,065 B2
(45) Date of Patent: Feb. 6, 2018

(54) INHIBITING ACTIVITY OF SENESCENT CELLS USING A GLUCOCORTICOID

(71) Applicant: Buck Institute for Research on Aging, Novato, CA (US)

(72) Inventors: Judith Campisi, Berkeley, CA (US); Remi-Martin Laberge, S. San Francisco, CA (US); Francis Rodier, Novato, CA (US); Marco Demaria, Groningen (NL)

(73) Assignee: Buck Institute for Research on Aging, Novato, CA (US)

( * ) Notice: Subject to any disclaimer, the term of this patent is extended or adjusted under 35 U.S.C. 154(b) by 0 days.

(21) Appl. No.: 15/077,630

(22) Filed: Mar. 22, 2016

(65) Prior Publication Data

US 2017/0119789 A1     May 4, 2017

Related U.S. Application Data

(63) Continuation of application No. 14/365,040, filed as application No. PCT/US2012/069601 on Dec. 13, 2012, now abandoned.

(60) Provisional application No. 61/692,680, filed on Aug. 23, 2012, provisional application No. 61/570,166, filed on Dec. 13, 2011.

(51) Int. Cl.
| | |
|---|---|
| *A61P 35/04* | (2006.01) |
| *A61K 31/56* | (2006.01) |
| *A61K 31/573* | (2006.01) |
| *G01N 33/50* | (2006.01) |
| *A61K 31/352* | (2006.01) |
| *A61K 45/06* | (2006.01) |

(52) U.S. Cl.
CPC .......... *A61K 31/573* (2013.01); *A61K 31/352* (2013.01); *A61K 45/06* (2013.01); *G01N 33/502* (2013.01); *G01N 33/5011* (2013.01); *G01N 33/5044* (2013.01)

(58) Field of Classification Search
None
See application file for complete search history.

(56) References Cited

U.S. PATENT DOCUMENTS

| | | | |
|---|---|---|---|
| 6,201,020 | B1 | 3/2001 | Zhang et al. |
| 7,390,799 | B2 | 6/2008 | Bruncko et al. |
| 7,642,260 | B2 | 1/2010 | Bruncko et al. |
| 7,767,684 | B2 | 8/2010 | Bruncko et al. |
| 7,829,556 | B2 | 11/2010 | Bemis et al. |
| 7,842,681 | B2 | 11/2010 | Elmore et al. |
| 7,851,626 | B2 | 12/2010 | Ding et al. |
| 7,879,857 | B2 | 2/2011 | Mabire et al. |
| 7,928,104 | B2 | 4/2011 | Mabire et al. |
| 7,973,161 | B2 | 7/2011 | Bruncko et al. |
| 8,071,623 | B2 | 12/2011 | Jones et al. |
| 8,168,645 | B2 | 5/2012 | Baell et al. |
| 8,343,967 | B2 | 1/2013 | Ding et al. |
| 8,426,422 | B2 | 4/2013 | Hexamer et al. |
| 8,518,970 | B2 | 8/2013 | Baell et al. |
| 8,541,417 | B2 | 9/2013 | Brown et al. |
| 8,557,983 | B2 | 10/2013 | Bruncko et al. |
| 8,563,735 | B2 | 10/2013 | Bruncko et al. |
| 8,586,754 | B2 | 11/2013 | Bruncko et al. |
| 8,609,623 | B2 | 12/2013 | Bondarev |
| 8,614,318 | B2 | 12/2013 | Bruncko et al. |
| 8,624,027 | B2 | 1/2014 | Shah et al. |
| 9,089,561 | B2 | 7/2015 | Yamaguchi et al. |
| 2003/0147899 | A1 | 8/2003 | Dhabhar |
| 2005/0019865 | A1 | 1/2005 | Kihm et al. |
| 2005/0181076 | A1 | 8/2005 | Ziegler |
| 2007/0099186 | A1 | 5/2007 | D'Adda et al. |
| 2008/0221132 | A1 | 9/2008 | Cai et al. |
| 2008/0234362 | A1 | 9/2008 | Chandler |
| 2009/0202654 | A1 | 8/2009 | Nixon |
| 2009/0281129 | A1 | 11/2009 | Chang et al. |
| 2010/0016218 | A1 | 1/2010 | Lichter et al. |
| 2010/0125064 | A1 | 5/2010 | Boettcher et al. |
| 2010/0190807 | A1 | 7/2010 | Porter et al. |
| 2010/0260733 | A1 | 10/2010 | Qi |
| 2010/0292200 | A1 | 11/2010 | Kile et al. |
| 2010/0310504 | A1 | 12/2010 | Lowe et al. |
| 2011/0027806 | A1 | 2/2011 | Gordon et al. |
| 2011/0124607 | A1 | 5/2011 | Park et al. |
| 2011/0212909 | A1 | 9/2011 | Wen et al. |

(Continued)

FOREIGN PATENT DOCUMENTS

| | | |
|---|---|---|
| CN | 101588805 A | 11/2009 |
| JP | 2009161494 A | 7/2009 |

(Continued)

OTHER PUBLICATIONS

Cristofalo et al, 1979. Federation Proceedings. 38(5): 1851-1856.*
Grove et al, 1977. J Cell Physiol. 90: 415-522.*
Dimri et al, 1995. Proc Natl Acad Sci USA. 92: 9363-9367.*
Funder et al, 1997. Annu Rev Med. 48: 231-240.*
McKay, et al. Corticosteroids in the Treatment of Neoplasms. Holland-Frei Cancer Medicine. 6th edition. Copyright 2003, BC Decker Inc. 9 pages.
Adams. Healing and hurting: molecular mechanisms, functions, and pathologies of cellular senescence. Mol Cell. Oct. 9, 2009;36(1):2-14. doi: 10.1016/j.molcel.2009.09.021.
Allshire, et al. Human telomeres contain at least three types of G-rich repeat distributed non-randomly. Nucleic Acids Res. Jun. 26, 1989;17(12):4611-27.
Baker et al. Clearance of p16Ink4a-positive senescent cells delays ageing-associated disorders. Nature 479(7372):232-236 (2011).
Bennett, et al. SP600125, An Anthrapyrazolone Inhibitor of Jun N-Terminal Kinase. PNAS, vol. 98, No. 24, 20, 2001, pp. 13681-13686.

(Continued)

*Primary Examiner* — Zachary Howard
(74) *Attorney, Agent, or Firm* — Michael Schiff; Wilson Sonsini Goodrich & Rosati

(57) ABSTRACT

Methods are provided herein for enhancing the effectiveness of medical therapies by administering agents that suppress a biological damage response that is inducible by the medical therapy administered to a subject. In certain embodiments, a method is provided for administering an anti-senescent cell agent that suppresses a biological response comprising cellular senescence that is induced by the medical therapy.

15 Claims, 38 Drawing Sheets

(56) References Cited

U.S. PATENT DOCUMENTS

| | | |
|---|---|---|
| 2011/0300112 A1 | 12/2011 | Marban et al. |
| 2012/0108590 A1 | 5/2012 | Birtalan et al. |
| 2012/0129853 A1 | 5/2012 | Elmore et al. |
| 2012/0183534 A1 | 7/2012 | Gruber |
| 2012/0277210 A1 | 11/2012 | Catron et al. |
| 2013/0096121 A1 | 4/2013 | Wang et al. |
| 2013/0267534 A1 | 10/2013 | Bruncko et al. |
| 2013/0287763 A1 | 10/2013 | Sathyanarayanan et al. |
| 2013/0302283 A1 | 11/2013 | Kihm |
| 2014/0017341 A1 | 1/2014 | Gourlaouen |
| 2014/0073640 A1 | 3/2014 | Judd et al. |
| 2014/0275082 A1 | 9/2014 | Tao et al. |
| 2014/0328893 A1 | 11/2014 | Adnot |
| 2014/0329854 A1 | 11/2014 | Larsen et al. |
| 2014/0335074 A1 | 11/2014 | Campisi et al. |
| 2014/0378683 A1 | 12/2014 | Porter et al. |
| 2015/0044184 A1 | 2/2015 | Chen et al. |
| 2015/0056195 A1 | 2/2015 | Bertolotto-Ballotti |
| 2015/0072950 A1 | 3/2015 | Sauve et al. |
| 2015/0072972 A1 | 3/2015 | Mevellec et al. |
| 2015/0140036 A1 | 5/2015 | Mannick et al. |
| 2015/0210717 A1 | 7/2015 | Günes et al. |

FOREIGN PATENT DOCUMENTS

| | | |
|---|---|---|
| WO | WO-03028443 A1 | 4/2003 |
| WO | WO-2005069880 A2 | 8/2005 |
| WO | WO-2006018632 A2 | 2/2006 |
| WO | WO-2006125166 A2 | 11/2006 |
| WO | WO-2008113131 A1 | 9/2008 |
| WO | WO-2009039553 A1 | 4/2009 |
| WO | WO-2009085216 A2 | 7/2009 |
| WO | WO-2009105234 A2 | 8/2009 |
| WO | WO-2010134790 A2 | 11/2010 |
| WO | WO-2010148447 A1 | 12/2010 |
| WO | WO-2011068561 A1 | 6/2011 |
| WO | WO-2011150016 A1 | 12/2011 |
| WO | WO-2013054153 A1 | 4/2013 |
| WO | WO-2013170174 A1 | 11/2013 |
| WO | WO-2014041125 A1 | 3/2014 |
| WO | WO-2014174511 A1 | 10/2014 |
| WO | WO-2014186878 A1 | 11/2014 |
| WO | WO-2015044649 A1 | 4/2015 |
| WO | WO-2015051766 A1 | 4/2015 |
| WO | WO-2015066442 A1 | 5/2015 |
| WO | WO-2015070280 A1 | 5/2015 |
| WO | WO-2015073644 A1 | 5/2015 |

OTHER PUBLICATIONS

Berenson, et al. Maintenance therapy with alternate-day prednisone improves survival in multiple myeloma patients. Blood. 99(9). May 1, 2002. 3163-8.

Braun, et al. Cellular senescence limits regenerative capacity and allograft survival.J Am Soc Nephrol. Sep. 2012;23(9):1467-73. doi: 10.1681/ASN.2011100967. Epub Jul. 12, 2012.

Campisi, et al. Cellular senescence: a link between cancer and age-related degenerative disease? Semin Cancer Biol. Dec. 2011;21(6):354-9. doi: 10.1016/j.semcancer.2011.09.001. Epub Sep. 10, 2011.

Campisi, et al. Cellular senescence: when bad things happen to good cells. Nature Reviews Molecular Cell Biology 8:729-740, 2007.

Campisi, J. Cellular senescence: putting the paradoxes in perspective. Curr Opin Genet Dev. Feb. 2011;21(1):107-12. doi: 10.1016/j.gde.2010.10.005. Epub Nov. 17, 2010.

Campisi, J. Senescent cells, tumor suppression, and organismal aging: good citizens, bad neighbors. Cell. Feb. 25, 2005;120(4):513-22.

Chang, et al. Effects of p21 Wafl/Cipl/Sdilon cellular gene expression: Implications for carcinogenesis, senescence, and age-related diseases. PNAS 97(8):4291-4296, 2000.

Chistiakov. How to fight with senescent cells? Geriatr Gerontol Int. Apr. 2011;11(2):233-5. doi: 10.1111/.1447-0594.2010.00654.x.

Chung, et al. Molecular inflammation: underpinnings of aging and age-related diseases. Ageing Res Rev. Jan. 2009;8(1):18-30. doi: 10.1016/j.arr.2008.07.002. Epub Jul. 18, 2008.

Coppe, et al. Senescence-associated secretory phenotypes reveal cell-nonautonomous functions of oncogenic RAS and the p53 tumor suppressor. PLoS Biol. Dec. 2, 2008;6(12):2853-68. doi: 10.1371/journal.pbio.0060301.

Davalos, et al. p53-dependent release of Alarmin HMGB1 is a central mediator of senescent phenotypes. J Cell Biol. May 13, 2013;201(4):613-29. doi: 10.1083/jcb.201206006. Epub May 6, 2013.

Davalos, et al. Senescent cells as a source of inflammatory factors for tumor progression. Cancer Metastasis Rev. Jun. 2010;29(2):273-83. doi: 10.1007/s10555-010-9220-9.

Deursen. Clearance of senescent cells and adult aging phenotypes. Pitts. Jun. 2014. 15 pages.

Deursen, et al. Senescent cells have some nerve! Mayo Clinic. NCI. Mar. 2015. Rochester, MN. 15 pages.

Deursen, et al. Senescent cells shorten health and life span. Mayo Clinic. Berlin. Febs 2015. 30 pages.

Deursen, et al. Senescent in aging and age-related disease: from mechanism to therapy. Mayo Clinic. ICSA Conference. Jul. 2015. Santiago de Compostela. 40 pages.

Deursen. Senescent Cells as Drivers of Cancer & Aging. Mayo Clinic. NYU Dec. 2014. 55 pages.

Deursen. The role of p16+ (senescent) cells in aging. Erice. Jun. 2015. 17 pages.

Deursen. Understanding Senescence and Chromosomal Instability in Cancer and Aging. Mayo Clinic. Ohio State. Jan. 2015. 49 pages.

Efeyan, et al. Induction of p53-dependent senescence by the MDM2 antagonist nutlin-3a in mouse cells of fibroblast origin. Cancer Res. Aug. 1, 2007;67(15):7350-7.

Elion, et al. Selectivity of action of an antiherpetic agent, 9-(2-hydroxyethoxymethyl) guanine. Proc Natl Acad Sci U S A. Dec. 2007;74(12):5716-20.

Field, et al. 9-([2-hydroxy-1-(hydroxymethyl)ethoxy]methyl) guanine: a selective inhibitor of herpes group virus replication. Proc Natl Acad Sci U S A. Jul. 1983;80(13):4139-43.

Freund, et al. Inflammatory networks during cellular senescence: causes and consequences. Trends Mol Med. May 2010;16(5):238-46. doi: 10.1016/j.molmed.2010.03.003. Epub May 3, 2010.

Freund, et al. Lamin B1 loss is a senescence-associated biomarker. Mol Biol Cell. Jun. 2012;23(11):2066-75. doi: 10.1091/mbc.E11-10-0884. Epub Apr. 11, 2012.

Gorenne, et al. Vascular smooth muscle cell senescence in atherosclerosis. Cardiovasc Res. Oct. 1, 2012;72(1):9-17. Epub Jun. 6, 2006.

Gorgoulis, et al. Oncogene-induced senescence: the bright and dark side of the response. Curr Opin Cell Biol. Dec. 2010;22(6):816-27. doi: 10.1016/j.ceb.2010.07.013. Epub Sep. 16, 2010.

Greider, et al. Identification of a specific telomere terminal transferase activity in Tetrahymena extracts. Cell. Dec. 1985;43(2 Pt 1):405-13.

Hahn, et al. Inhibition of telomerase limits the growth of human cancer cells. Nat Med. Oct. 1999;5(10):1164-70.

Harnden, et al. Synthesis and antiviral activity of 9-[4-hydroxy-3-(hydroxymethyl)but-1-yl]purines. J Med Chem. Sep. 1987;30(9):1636-42.

Hodge, et al. Mode of action of 9-(4-hydroxy-3-hydroxymethylbut-1-yl)guanine (BRL 39123) against herpes simplex virus in MRC-5 cells. Antimicrob Agents Chemother. Feb. 1989;33(2):223-9.

Hultdin, et al. Telomere analysis by fluorescence in situ hybridization and flow cytometry. Nucleic Acids Res. Aug. 15, 1998;26(16):3651-6.

International search report and written opinion dated Apr. 30, 2013 for PCT/US2012/069601.

Kassem, et al. Senescence-associated intrinsic mechanisms of osteoblast dysfunctions. Aging Cell. Apr. 2011;10(2):191-7. doi: 10.1111/j.1474-9726.2011.00669.x. Epub Feb. 18, 2011.

(56) References Cited

OTHER PUBLICATIONS

Kim, et al. SP600125, an inhibitor of Jnk pathway, reduces viability of relatively resistant cancer cells to doxorubicin. Biochem Biophys Res Commun. Sep. 25, 2009;387(3):450-5. doi: 10.1016/j.bbrc.2009.07.036. Epub Jul. 14, 2009.
Kim, et al. Specific association of human telomerase activity with immortal cells and cancer. Science. Dec. 23, 1994;266(5193):2011-5.
Krtolica, et al. Senescent fibroblasts promote epithelial cell growth and tumorigenesis: a link between cancer and aging. Proc Natl Acad Sci U S A. Oct. 9, 2001;98(21):12072-7. Epub Oct. 2, 2001.
Kuilman, et al. The essence of senescence. Genes Develop., 2010, 24:2463-2479.
Laberge, et al. Glucocorticoids suppress selected components of the senescence-associated secretory phenotype. Aging Cell 11(4):569-578, 2012.
Le, et al. Ionizing radiation-induced long-term expression of senescence markers in mice is independent of p53 and immune status. Aging Cell. Jun. 2010;9(3):398-409. doi: 10.1111/j.1474-9726.2010.00567.x. Epub Mar. 13, 2010.
Lessene; et al., "Structure-guided design of a selective BCL-X(L) inhibitor.", Jun. 2013, 9(6), 390-7.
Lycke, et al. Acyclovir levels in serum and cerebrospinal fluid after oral administration of valacyclovir. Antimicrob Agents Chemother. Aug. 2003;47(8):2438-41.
Martin, et al. 9-[(1,3-Dihydroxy-2-propoxy)methyl]guanine: a new potent and selective antiherpes agent. J Med Chem. May 1983;26(5):759-61.
Martin, et al. The Role of Chondrocyte Senescence in the Pathogenesis of Osteoarthritis and in Limiting Cartilage Repair. J Bone Joint Surg Am, vol. 85, Suppl 2, Apr. 2003, pp. 106-110.
Minamino et al., Vascular Cell Senescence: Contribution to Atherosclerosis. Journal of the American Heart Association, Circ Res. Jan. 5, 2007;100(1):15-26.
National Cancer Institute. Metastatic Cancer Fact Sheet (http://www.cancer.gov/about-cancer/what-is-cancer/metastatic-fact-sheet). May 28, 2013. Accessed on Sep. 15, 2015. 8 pages.
Office action dated Sep. 22, 2015 for U.S. Appl. No. 14/365,040.
Orjalo et al. Cell surface-bound IL-1alpha is an upstream regulator of the senescence-associated IL-6/IL-8 cytokine network. PNAS USA 106(40)17031-17036 (2009).
Piketty, et al. Monitoring plasma levels of ganciclovir in AIDS patients receiving oral ganciclovir as maintenance therapy for CMV retinitis. Clin Microbiol Infect. Mar. 2000;6(3):117-20.
Prieur, et al. Cellular senescence in vivo: a barrier to tumorigenesis. Curr Opin Cell Biol. Apr. 2008;20(2):150-5. doi: 10.1016/j.ceb.2008.01.007. Epub Mar. 18, 2008.
Roberts, et al. Senescence in human intervertebral discs. Eur Spine J. Aug. 2006;15 Suppl 3:S312-6. Epub Jun. 14, 2006.
Rodier, et al. Persistent DNA damage signalling triggers senescence-associated inflammatory cytokine secretion. Nat Cell Biol. Aug. 2009;11(8):973-9. doi: 10.1038/ncb1909. Epub Jul. 13, 2009.
Roninson. Tumor Cell Senescence in Cancer Treatment. Cancer Research 63(11):2705-2715, 2003.
Shain. Metastatic myeloma? Blood. 119(24). Jun. 14, 2012. 5612-3.
Shangary, et al. Temporal activation of p53 by a specific MDM2 inhibitor is selectively toxic to tumors and leads to complete tumor growth inhibition. Proc Natl Acad Sci U S A. Mar. 11, 2008;105(10):3933-8. doi: 10.1073/pnas.0708917105. Epub Mar. 3, 2008.
Sharpless, et al. Telomeres, stem cells, senescence, and cancer. Journal of Clinical Investigation 113(2):160-168, 2004.
Sis, et al. Accelerated expression of senescence associated cell cycle inhibitor p16INK4A in kidneys with glomerular disease. Kidney Int. Feb. 2007;71(3):218-26. Epub Dec. 20, 2006.
Smee, et al. Anti-herpesvirus activity of the acyclic nucleoside 9-(1,3-dihydroxy-2-propoxymethyl)guanine. Antimicrob Agents Chemother. May 1983;23(5):676-82.
Stanley et al. Senescence and the Healing Rates of Venous Ulcers. J Vasc Surg. Jun. 2001;33(6):1206-11.
Tchkonia, et al. Fat tissue, aging, and cellular senescence. Aging Cell. Oct. 2010;9(5):667-84.
Tsuji, et al. Alveolar cell senescence exacerbates pulmonary inflammation in patients with chronic obstructive pulmonary disease. Respiration. 2010;80(1):59-70. doi: 10.1159/000268287. Epub Dec. 17, 2009.
Velin, et al. Telomerase is not activated in human hyperplastic and adenomatous parathyroid tissue. Eur J Endocrinol. Aug. 2001;145(2):161-4.
Wege, et al. SYBR Green real-time telomeric repeat amplification protocol for the rapid quantification of telomerase activity. Nucleic Acids Res. Jan. 15, 2003;31(2):E3-3.
Wright, et al. Telomerase activity in human germline and embryonic tissues and cells. Dev Genet. 1996;18(2):173-9.
Yang, et al. Effects of GM-CSF, IL-3, and GM-CSF/IL-3 fusion protein on apoptosis of human myeloid leukemic cell line Tf-1 induced by irradiation. Acta Pharmacol Sin. Jan. 2004;25(1):68-75.
Yeager, et al. Telomerase-negative immortalized human cells contain a novel type of promyelocytic leukemia (PML) body. Cancer Res. Sep. 1, 1999;59(17):4175-9.
Zhao; et al., "Small molecule inhibitors of MDM2-p53 and MDMX-p53 interactions as new cancer therapeutics. BioDiscovery, 8.", 2013, 8(4), 15 pages.

* cited by examiner

Entire 9267 nt sequence, uninterrupted
ctaaattgtaagcgttaatatttttgttaaaattcgcgttaaatttttgttaaatcagctcattt
tttaaccaataggcgaaatcggcaaaatcccttataaatcaaaagaatagaccgagataggt
tgagtgttgttccagtttggaacaagagtccactattaaagaacgtggactccaacgtcaaagg
gcgaaaaaccgtctatcaggcgatggcccactacgtgaaccatcaccctaatcaagttttttg
gggtcgaggtgccgtaaagcactaaatcggaaccctaaagggagcccccgatttagagcttgac
ggggaaagccggcgaacgtggcgagaaaggaaggaagaaagcgaaaggagcggcgctaggc
gctggcaagtgtagcggtcacgctgcgcgtaaccaccacaccgccgcgcttaatgcgccgcta
cagggcgcgtcccattcgccattcaggctgcgcaactgttgggaagggcgatcggtgcgggcct
cttcgctattacgccagctggcgaaagggggatgtgctgcaaggcgattaagttgggtaacgcc
agggttttcccagtcacgacgttgtaaaacgacggccagtgagcgcgcgtaatacgactcacta
tagggcgaattggagctccaccgcggtggcggccgctctagaactagtgGATCCGTGTAAAGTC
ACTGCTTTTATAGCTACATCTGCATAGATCCCTGTATGAAAGCATGTACTACCTGGATAATAA
TATCTGTATTTTTCTGTAGTAGGAAATCAGTGTAGTTTTTAAAACCAAAAAGTATTGTTATTAA
TCTATCTTTGATCTCAAACAATTTCAATGACCTAGTATAGTGATTCTACGGAAAGCCCTGCAA
TTTACTCAAAGCAGTTTTTAAATATTGTTTTAAAAGTGTGTGTGTGTGTGTGTGTGTGTGTGT
TGTGTGTGTGGTGTTAAAGTCATTTTCAAACCCCTCACAATGTCTTGAATGTGACATTTGAGTC
ATTTATGGTAACTTATAACTCCTTTGAAGAAGTTATTCAGAATTGAGGTTCCAGACACACAAAT
GCACAATACACCATTTTTCCTTCCAGTTAACAATCAGAGGGCAACACTTATTTTAAAGGAAAA
TCGACTCCATAAGGGACTTTATAAAGGGGTAGACATAAACCAGTATCAGGGATAAACTCTCCGT
TCCCCTGTTTAACCTAATTTTCCCAGGGCCATCCTGGAATACGAATTTTCTCTTGAAATACAGT
CAAAGAAAAAGTGGTAGGCTACAGAGCAGAGGAAACACTGGACACAGCGACCCACCCCAGAGTCACTT
CCCTTAATCTAATGACTAGGTTTTTTCTGAAAGTTATTTTGTTAGAACACAGGAACTTTT
GCGACCACAGTGATGCTTTTAGAGGGTTGAATCCTCAAAAAGAAAATTAATCGCAACTAGTAGA
AGGGAGATTACTTATTGATTCTTATAACTTCTGCAGGAATACACAGTTATGAGTTAGGGCAAAG
AGAAAATTGACTTTTAATATTCTCTATCACTAACATGAGAGAACATGTATGTGTTCCAAAATAA
TTTTTATTTATTGAAAACCCGCTATATACCTGGATTTTCACAGAATATTCATTACTCTCCAAAA
TGGCCTTTTCTAGGTGAATTTTATTTTCCTTACAGACCTCAAGAAGTTTACATAATTTACTTAA
ACCTGAGGAGAGAGAACAAAGCCTCAGAAAATTTACATAGTTTATTTAAACTAAACTCAGCTTG
CTTGGTAGCAGCTTCTAATCCCAGCAGTTAAAGAGACAGAAGCAGGGCCAACCTGGGGTATAAT
ATAAGGTGAGACTCTCCTTTCTTTCTCTCTGTCTCTGTCTGTCTCTGTCTCTGTGTGTGTGT
GTGTGTGTGTGTGTGTGTGTCTCCTCTCTCTCTCTCTCTCTCTCTCTCTCTCTCTCTCTCTG
TCTCTCTCTCCCTCCCCCTCCCTCCCTCTCCCCCTCCTCTCTCCCTCCCTCTCCCTCCCCCCC
CCCACACATTTGAATTCGTGGAGTTGGTAAATGAGGGGTCAGTTCTCTGTCTGTCTGTAGTTTT
GTGTCCACAGGATATGACTGACATTCTCACCACACACATACAAAGTCAAAAATAGCTGTGGCCA
TATAAAGAATATGGGGAGAGAAAATTATTCAAAATCTGCAGAAAATAATGCCAGGCCTTTAATC
CTGGCACCCAGGAGGCAGAAGGGAGACAGAGTTCTGAGTTTATGCTGAGTTCCAGGAGTGGAAG
AAAGGGCCATTGCCTTTCTGGTGAGGACTGTCTTTTTAAATCCTCCCTTCTGTCCAGTACTGGT
AACTCTGCCCAAAGCGTGTTCTTCTTCCTGCCTCACAAGATTGCAAAGACGTTTTTAACGAACA
ATTTAAACCGGTGCAACGTTTATGCGCAGCACACCAACTCATTTAAACAAACAACAGCCCCATA
AAATAGAAATACTTTATAAGCAGATTGCCCTCCGATGACTTCACCCCGTCACTTTTTTATAGTT
GTGTACAGAATCCTAGCACTGATACAGCAACATCAGAAATGTTTCTGCAAATCCTTCGCAAAGA
TTCGGATTTCATACTGGGCGTGGTACCCTCCAAAATGAGTTGTTTGAGCTAGGGTTGTTGGGAT
CTCAGCTTGGCGAAGTTGTAGCTCTTCTTCTGAATAAAGATGACACAATTTCTGCTAAGAT

*Fig. 10A*

```
GTTAAATACCTTAAGTTTCAGTGTAGTGATGAAAATTACCCTCCTTCGTTTTTCTAATACCTGG
GTGTTGCACTGGGGAGGAAGGAGAGATTTCGAGAAGGACTAGTTCACTTTCTCAGAAGACACGT
GTGCACTTCTTTGCTGTGCGGGTCCAGAAGGAGCCCAGCGTGTCAAAGGGTGACCAGGCATGGG
GGAGGGGTGTTAGCGTGGGTAGCAGGCGGGGGCTGTCCGATCCTTTAGCGCTGTTTCAACGCCC
AGCTCTCCTCCTGAACCCTGCATCTCTTCTGTAGTCCGGCTCCATCCCTTTCCCTCCCCCAT
CCGGAGGTGGGGGAACAGCAGTGTTTTCAGGGGTGTTCAATTCATGCTATATTCAGGGCAAAT
AGCGCCACCTATGGCGGGCTGTGGAGCCAGGTCAGGAGCAGAGTGTGGCTCCCCCCCCCCCCA
CACCATCCTCAGAGGAAGGAAGGAGGGACCCACTGGTCACACGACTGGGCGATTGGGCGGGCAC
TGAATCTCCGCGAGGAAAGCGAACTCGAGGAGAGCCATCACGCGTAGCatggggagtagcaaga
gcaagcctaaggacccagccagcgctctagaggcgtccaagtcgaaaccattagtcccggcga
tggcagaacatttcctaaaaggggacaaacatgtgtcgtccattatacaggcatgttggaggac
ggcaaaaaggtggacagtagtagagatcgcaataaacctttcaaattcatgttgggaaaacaag
aagtcattaggggatgggaggagggcgtggctcaaatgtccgtcggccaacgcgctaagctcac
catcagccccgactacgcatacggcgctacggacatcccggaattattccccctcacgctacc
ttggtgtttgacgtcgaactgttgaagctcgagactagaggagtgcaggtggagactatctccc
caggagacgggcgcaccttccccaagcgcggccagacctgcgtggtgcactacaccgggatgct
tgaagatggaaagaaagttgattcctcccgggacagaaacaagcccctttaagtttatgctaggc
aagcaggaggtgatccgaggctgggaagaaggggttgcccagatgagtgtgggtcagagagcca
aactgactatatctccagattatgcctatggtgccactgggcacccaggcatcatcccaccaca
tgccactctcgtcttcgatgtggagcttctaaaactggaaactagtagtgaatcacagactttg
gacaaagtttaccaaatgaaaagcaaacctcggggatactgtctgatcatcaacaatcacaatt
ttgcaaaagcacgggagaaagtgcccaaacttcacagcattagggacaggaatggaacacactt
ggatgcaggggctttgaccacgacctttgaagagcttcatttgagatcaagccccacgatgac
tgcacagtagagcaaatctatgagattttgaaaatctaccaactcatggaccacagtaacatgg
actgcttcatctgctgtatcctctcccatggagacaagggcatcatctatggcactgatggaca
ggaggcccccatctatgagctgacatctcagttcactggtttgaagtgcccttcccttgctgga
aaacccaaagtgttttttattcaggcttgtcaggggataactaccagaaaggtatacctgttg
agactgattcagaggagcaaccctatttagaaatggatttatcatcacctcaaacgagatatat
cccggatgaggctgactttctgctgggatgccactgtgaataactgtgtttcctaccgaaac
cctgcagagggaacctggtacatccagtcactttgccagagcctgagagagcgatgtcctcgag
gcgatgatattctcaccatcctgactgaagtgaactatgaagtaagcaacaaggatgacaagaa
aaacatggggaaacagatgcctcagcctactttcacactaagaaaaaacttgtcttcccttct
gatgattacaaggatgacgacgataagtgaggatcaacctcgaggaattcACGCGTTTAATTAA
CTCGAGGTTTTCGAGGTCGACGGTATCGATAAGCTTGATATCGAATTCCGCCCCTCTCCCTCCC
CCCCCCCTAACGTTACTGGCCGAAGCCGCTTGGAATAAGGCCGGTGTGCGTTTGTCTATATGTT
ATTTTCCACCATATTGCCGTCTTTTGGCAATGTGAGGGCCCGGAAACCTGGCCCTGTCTTCTTG
ACGAGCATTCCTAGGGGTCTTTCCCCTCTCGCCAAAGGAATGCAAGGTCTGTTGAATGTCGTGA
AGGAAGCAGTTCCTCTGGAAGCTTCTTGAAGACAAACAACGTCTGTAGCGACCCTTTGCAGGCA
GCGGAACCCCCCACCTGGCGACAGGTGCCTCTGCGGCCAAAAGCCACGTGTATAAGATACACCT
GCAAAGGCGGCACAACCCCAGTGCCACGTTGTGAGTTGGATAGTTGTGGAAAGAGTCAAATGGC
TCTCCTCAAGCGTATTCAACAAGGGCTGAAGGATGCCCAGAAGGTACCCCATTGTATGGGATC
TGATCTGGGGCCTCGGTGCACATGCTTTACATGTGTTTAGTCGAGGTTAAAAAAACGTCTAGGC
```

*Fig. 10B*

```
CCCCCGAACCACGGGGACGTGGTTTTCCTTTGAAAAACACGATGATAATATGGCCACAACCATG
GTGAGCAAGGGCGAGGAGCTGTTCACCGGGGTGGTGCCCATCCTGGTCGAGCTGGACGGCGACG
TAAACGGCCACAAGTTCAGCGTGTCCGGCGAGGGCGAGGGCGATGCCACCTACGGCAAGCTGAC
CCTGAAGTTCATCTGCACCACCGGCAAGCTGCCCGTGCCCTGGCCCACCCTCGTGACCACCCTG
ACCTACGGCGTGCAGTGCTTCAGCCGCTACCCCGACCACATGAAGCAGCACGACTTCTTCAAGT
CCGCCATGCCCGAAGGCTACGTCCAGGAGCGCACCATCTTCTTCAAGGACGACGGCAACTACAA
GACCCGCGCCGAGGTGAAGTTCGAGGGCGACACCCTGGTGAACCGCATCGAGCTGAAGGGCATC
GACTTCAAGGAGGACGGCAACATCCTGGGGCACAAGCTGGAGTACAACTACAACAGCCACAACG
TCTATATCATGGCCGACAAGCAGAAGAACGGCATCAAGGTGAACTTCAAGATCCGCCACAACAT
CGAGGACGGCAGCGTGCAGCTCGCCGACCACTACCAGCAGAACACCCCCATCGGCGACGGCCCC
GTGCTGCTGCCCGACAACCACTACCTGAGCACCCAGTCCGCCCTGAGCAAAGACCCCAACGAGA
AGCGCGATCACATGGTCCTGCTGGAGTTCGTGACCGCCGCCGGGATCACTCTCGGCATGGACGA
GCTGTACAAGTAAAGCGGCCGCGATCTTTTTCCCTCTGCCAAAAATTATGGGGACATCATGAAG
CCCCTTGAGCATCTGACTTCTGGCTAATAAAGGAAATTTATTTTCATTGCAATAGTGTGTTGGA
ATTTTTTGTGTCTCTCACTCGGAAGGACATATGGGAGGGCAAATCATTTAAAACATCAGAATGA
GTATTTGGTTTAGAGTTTGGCAACATATGCCATATGCTGGCTGCCATGAACAAAGGTGGCTATA
AAGAGGTCATCAGTATATGAAACAGCCCCCTGCTGTCCATTCCTTATTCCATAGAAAAGCCTTG
ACTTGAGGTTAGATTTTTTTATATTTTGTTTTGTGTTATTTTTTTCTTTAACATCCCTAAAAT
TTTCCTTACATGTTTTACTAGCCAGATTTTTCCTCCTCTCCTGACTACTCCCAGTCATAGCTGT
CCCTCTTCTCTTATGAAGATCCCTCGACCTGCAGCCCAAGCTTGGCGTAATCATGGTCATAGCT
GTTTCCTGTGTGAAATTGTTATCCGCTCACAATTCCACACAACATACGAGCCGGAAGCATAAAG
TGTAAAGCCTGGGGTGCCTAATGAGTGAGCTAACTCACATTAATTGCGTTGCGCTCACTGCCCG
CTTTCCAGTCGGGAAACCTGTCGTGCCAGCGGATCCGCATCTCAATTAGTCAGCAACCATAGTC
CCGCCCCTAACTCCGCCCATCCCGCCCCTAACTCCGCCCAGTTCCGCCCATTCTCCGCCCCATG
GCTGACTAATTTTTTTATTTATGCAGAGGCCGAGGCCGCCTAAACGGCCGGCCATcgataccg
tcgacctcgagggggggcccggtacccagcttttgttcccttttagtgagggttaattgcgcgct
tggcgtaatcatggtcatagctgtttcctgtgtgaaattgttatccgctcacaattccacacaa
catacgagccggaagcataaagtgtaaagcctggggtgcctaatgagtgagctaactcacatta
attgcgttgcgctcactgcccgctttccagtcgggaaacctgtcgtgccagctgcattaatgaa
tcggccaacgcgcggggagaggcggtttgcgtattgggcgctcttccgcttcctcgctcactga
ctcgctgcgctcggtcgttcggctgcggcgagcggtatcagctcactcaaaggcggtaatacgg
ttatccacagaatcaggggataacgcaggaaagaacatgtgagcaaaaggccagcaaaaggcca
ggaaccgtaaaaaggccgcgttgctggcgtttttccataggctccgcccccctgacgagcatca
caaaaatcgacgctcaagtcagaggtggcgaaacccgacaggactataaagataccaggcgttt
ccccctggaagctccctcgtgcgctctcctgttccgaccctgccgcttaccggatacctgtccg
cctttctcccttcgggaagcgtggcgctttctcatagctcacgctgtaggtatctcagttcggt
gtaggtcgttcgctccaagctgggctgtgtgcacgaaccccccgttcagcccgaccgctgcgcc
ttatccggtaactatcgtcttgagtccaacccggtaagacacgacttatcgccactggcagcag
ccactggtaacaggattagcagagcgaggtatgtaggcggtgctacagagttcttgaagtggtg
gcctaactacggctacactagaaggacagtatttggtatctgcgctctgctgaagccagttacc
ttcggaaaaagagttggtagctcttgatccggcaaacaaaccaccgctggtagcggtggttttt
ttgtttgcaagcagcagattacgcgcagaaaaaaaggatctcaagaagatcctttgatcttttc
```

*Fig. 10C*

```
tacggggtctgacgctcagtggaacgaaaactcacgttaagggattttggtcatgagattatca
aaaaggatcttcacctagatccttttaaattaaaaatgaagttttaaatcaatctaaagtatat
atgagtaaacttggtctgacagttaccaatgcttaatcagtgaggcacctatctcagcgatctg
tctatttcgttcatccatagttgcctgactcccgtcgtgtagataactacgatacgggagggc
ttaccatctggcccagtgctgcaatgataccgcgagacccacgctcaccggctccagatttat
cagcaataaaccagccagccggaagggccgagcgcagaagtggtcctgcaactttatccgcctc
catccagtctattaattgttgccgggaagctagagtaagtagttcgccagttaatagtttgcgc
aacgttgttgccattgctacaggcatcgtggtgtcacgctcgtcgtttggtatggcttcattca
gctccggttcccaacgatcaaggcgagttacatgatcccccatgttgtgcaaaaaagcggttag
ctccttcggtcctccgatcgttgtcagaagtaagttggccgcagtgttatcactcatggttatg
gcagcactgcataattctcttactgtcatgccatccgtaagatgcttttctgtgactggtgagt
actcaaccaagtcattctgagaatagtgtatgcggcgaccgagttgctcttgcccggcgtcaat
acgggataataccgcgccacatagcagaactttaaaagtgctcatcattggaaaacgttcttcg
gggcgaaaactctcaaggatcttaccgctgttgagatccagttcgatgtaacccactcgtgcac
ccaactgatcttcagcatcttttactttcaccagcgtttctgggtgagcaaaaacaggaaggca
aaatgccgcaaaaaagggaataagggcgacacggaaatgttgaatactcatactcttcctttt
caatattattgaagcatttatcaggttattgtctcatgagcggatacatatttgaatgtattt
agaaaaataaacaaatagggggttccgcgcacatttccccgaaaagtgccac (SEQ ID
NO:1)
```

*Fig. 10D* ctaaattgtaagcgttaatattttgttaaaattcgcgttaaattttttgttaaatcagctcattt
tttaaccaataggccgaaatcggcaaaatcccttataaatcaaaagaatagaccgagatagggt
tgagtg (SEQ ID NO:2)

F1 ori:
ttgttccagtttggaacaagagtccactattaaagaacgtggactccaacgtcaaagggcgaaa
aaccgtctatcagggcgatggcccactacgtgaaccatcaccctaatcaagttttttggggtcg
aggtgccgtaaagcactaaatcggaaccctaaagggagccccccgatttagagcttgacggggaa
agccggcgaacgtggcgagaaaggaagggaagaaagcgaaaggagcgggcgctaggcgctggc
aagtgtagcggtcacgctgcgcgtaaccaccacaccgccgcgcttaatgcgccgctacagggc
gcgtc (SEQ ID NO:3)

LacZ alpha:
ccattcgccattcaggctgcgcaactgttgggaagggcgatcggtgcgggcctcttcgctatta
cgccagctggcgaaaggggatgtgctgcaaggcgattaagttgggtaacgccagggttttccc
agtcacgacgt (SEQ ID NO:4)

M13 fwd:
tgtaaaacgacggccagtgagcgcgc (SEQ ID NO:5)

T7:
gtaatacgactcactataggcgaattggagctccaccgcggtggcggccgctctagaactagtg
(SEQ ID NO:6)

BAMH1, p16 promoter:
GATCC (SEQ ID NO:7)

forprimer3, p16 promoter:
GTGTAAAGTCACT (SEQ ID NO:8)

*Fig. 11A* p16 promoter:
CTTTTATAGCTACATCTGCATAGATCCCCTGTATGAAAGCATGTACTACCTGGATAATAATATC
TGTATTTTTCTGTAGTAGGAAATCAGTGTAGTTTTTAAAACCAAAAAGTATTGTTATTAATCTA
TCTTTGATCTCAAACAATTTCAATGACCTAGTATAGTGATTTCTACGGAAAGCCCTGCAATTTA
CTCAAAGCAGTTTTTAAATATTGTTTTAAAAGTGTGTGTGTGTGTGTGTGTGTGTGTGTGTGTG
TGTGTGGTGTTAAAGTCATTTTCAAACCCCTCACAATGTCTTGAATGTGACATTTGAGTCATTT
ATGGTAACTTATAACTCCTTTGAAGAAGTTATTCAGAATTGAGGTTCCAGACACACAAATGCAC
AATACACCATTTTTCCTTCCAGTTAACAATCAGAGGGCAACACTTATTTTTAAAGGAAAATCGA
CTCCATAAGGGACTTTATAAAGGGGTAGACATAAACCAGTATCAGGGATAAACTCTCCGTTCCC
CTGTTTAACCTAATTTTCCCAGGGCCATCCTGGAATACGAATTTTCTCTTGAAATACAGTCAAA
GAAAAAGTGGTAGGCTACAGAGCAGAGGAAACACTGGACACAGCGACCCACCCCAGAGTCACTT
CCCTTAATCTAATGACTAGGTTTTTTCTGAAAGTTATTTTGTTAGAACACAGGAACTTTTGCGA
CCACAGTGATGCTTTTAGAGGGTTGAATCCTCAAAAAGAAAATTAATCGCAACTAGTAGAAGGG
AGATTACTTATTGATTCTTATAACTTCTGCAGGAATACACAGTTATGAGTTAGGGCAAAGAGAA
AATTGACTTTTAATATTCTCTATCACTAACATGAGAGAACATGTATGTGTTCCAAAATAATTTT
TATTTATTGAAAACCGCTATATACCTGGATTTTCACAGAATATTCATTACTCCAAAATGGC
CTTTTCTAGGTGAATTTTATTTTCCTTACAGACCTCAAGAAGTTTACATAATTTACTTAAACCT
GAGGAGAGAGAACAAAGCCTCAGAAAATTTACATAGTTTATTTAAACTAAACTCAGCTTGCTTG
GTAGCAGCTTCTAATCCCAGCAGTTAAAGAGACAGAAGCAGGGCCAACCTGGGGTATAATATAA
GGTGAGACTCTCCTTTCTTTCTCTCTGTCTCTGTCTGTCTCTGTCTCTGTGTGTGTGTGTGTGT
GTGTGTGTGTGTGTGTGTCTCCTCTCTCTCTCTCTCTCTCTCTCTCTCTCTCTCTCTCTGTCTC
TCTCTCCCTCCCCCTCCCTCCCTCTCCCCCTCCTCTCTCCCTCCCTCTCCCTCCCCCCCCCCCA
CACATTTGAATTCGTGGAGTTGGTAAATGAGGGGTCAGTTCTCTGTCTGTCTGTAGTTTTGTGT
CCACAGGATATGACTGACATTCTCACCACACACATACAAAGTCAAAAATAGCTGTGGCCATATA
AAGAATATGGGGAGAGAAAATTATTCAAAATCTGCAGAAAATAATGCCAGGCCTTTAATCCTGG
CACCCAGGAGGCAGAAGGGAGACAGAGTTCTGAGTTTATGCTGAGTTCCAGGAGTGGAAGAAAG
GGCCATTGCCTTTCTGGTGAGGACTGTCTTTTTAAATCCTCCCTTCTGTCCAGTACTGGTAACT
CTGCCCAAAGCGTGTTCTTCTTCCTGCCTCACAAGATTGCAAAGACGTTTTTAACGAACAATTT
AAACCGGTGCAACGTTTATGCGCAGCACACCAACTCATTTAAACAAACAACAGCCCCATAAAAT
AGAAATACTTTATAAGCAGATTGCCCTCCGATGACTTCACCCCGTCACTTTTTTATAGTTGTGT
ACAGAATCCTAGCACTGATACAGCAACATCAGAAATGTTTCTGCAAATCCTTCGCAAAGATTCG
GATTTCATACTGGGCGTGGTACCCTCCAAAATGAGTTGTTTGAGCTAGGGTTGTTGGGATCTCA
GCTTGGCGAAGTTGTAGCTCTTTCTTCTGAATAAAAGATGACACAATTTTCTGCTAAGATGTTA
AATACCTTAAGTTTCAGTGTAGTGATGAAAATTACCCTCCTTCGTTTTTCTAATACCTGGGTGT
TGCACTGGGGAGGAAGGAGAGATTTCGAGAAGGACTAGTTCACTTTCTCAGAAGACACGTGTGC
ACTTCTTTGCTGTGCGGGTCCAGAAGGAGCCCAGCGTGTCAAAGGGTGACCAGGCATGGGGGAG
GGGTGTTAGCGTGGGTAGCAGGCGGGGGCTGTCCGATCCTTTAGCGCTGTTTCAACGCCCAGCT
CTCCTCCTGAACCCTGCATCTCTTCTGTAGTCCGGGCTCCATCCCTTTCCCCTCCCCCATCCGG
AGGTGGGGGGAACAGCAGTGTTTTCAGGGGTGTTCAATTCATGCTATATTCAGGGCAAATAGCG
CCACCTATGGCGGGCTGTGGAGCCAGGTCAGGAGCAGAGTGTGGCTCCCCCCCCCCCACACC
ATCCTCAGAGGAAGGAAGGAGGGACCCACTGGTCACACGACTGGGCGATTGGGCGGGCACTGAA
TCTCCGCGAGGAAAGCGAACTCGAGGAGAGCCATCACGCGTAGC (SEQ ID NO:9)

*Fig. 11B*

FKBP:
atggggagtagcaagagcaagcctaaggaccccagccagcgctctagaggcgtccaagtcgaaa
ccattagtcccggcgatggcagaacatttcctaaaaggggacaaacatgtgtcgtccattatac
aggcatgttggaggacggcaaaaaggtggacagtagtagagatcgcaataaacctttcaaattc
atgttgggaaaacaagaagtcattaggggatggaggagggcgtggctcaaatgtccgtcggcc
aacgcgctaagctcaccatcagccccgactacgcatacggcgctaccggacatccggaattat
tcccctcacgctaccttggtgtttgacgtcgaactgttgaagctcgagactagaggagtgcag
gtggagactatctccccaggagacgggcgcaccttccccaagcgcggccagacctgcgtggtgc
actacaccgggatgcttgaagatggaaagaaagttgattcctcccgggacagaaacaagccctt
taagtttatgctaggcaagcaggaggtgatccgaggctgggaagaaggggttgcccagatgagt
gtgggtcagagagccaaactgactatatctccagattatgcctatggtgccactgggcacccag
gcatcatcccaccacatgccactctcgtcttcgatgtggagcttctaaaactggaaactagt
(SEQ ID NO:10)

Casp8:
agtgaatcacagactttggacaaagtttaccaaatgaaaagcaaacctcggggatactgtctga
tcatcaacaatcacaattttgcaaaagcacggggagaaagtgcccaaacttcacagcattaggga
caggaatggaacacacttggatgcagggctttgaccacgacctttgaagagcttcatttgag
atcaagccccacgatgactgcacagtagagcaaatctatgagattttgaaaatctaccaactca
tggaccacagtaacatggactgcttcatctgctgtatcctctcccatggagacaaggcatcat
ctatggcactgatggacaggaggccccatctatgagctgacatctcagttcactggtttgaag
tgcccttcccttgctggaaaacccaaagtgttttttattcaggcttgtcaggggataactacc
agaaaggtatacctgttgagactgattcagaggagcaaccctatttagaaatggatttatcatc
acctcaaacgagatatatcccggatgaggctgactttctgctggggatggccactgtgaataac
tgtgtttcctaccgaaaccctgcagagggaacctggtacatccagtcactttgccagagcctga
gagagcgatgtcctcgaggcgatgatattctcaccatcctgactgaagtgaactatgaagtaag
caacaaggatgacaagaaaaacatggggaaacagatgcctcagcctacttcacactaagaaaa
aaacttgtcttcccttctgat (SEQ ID NO:11)

Flag/Tag/Stop:
Gattacaaggatgacgacgataagtga (SEQ ID NO:12)

3'UTR:
ggatc (SEQ ID NO:13)

Multiple cloning site (MluI, PacI, XhoI, PmeI)
aacctcgaggaattcACGCGTTAATTAACTCGAGGTTT (SEQ ID NO:14)

*Fig. 11C*

IRES, GFP:
TCGAGGTCGACGGTATCGATAAGCTTGATATCGAATTCCGCCCCTCTCCCTCCCCCCCCCTAA
CGTTACTGGCCGAAGCCGCTTGGAATAAGGCCGGTGTGCGTTTGTCTATATGTTATTTTCCACC
ATATTGCCGTCTTTTGGCAATGTGAGGGCCCGGAAACCTGGCCCTGTCTTCTTGACGAGCATTC
CTAGGGGTCTTTCCCCTCTCGCCAAAGGAATGCAAGGTCTGTTGAATGTCGTGAAGGAAGCAGT
TCCTCTGGAAGCTTCTTGAAGACAAACAACGTCTGTAGCGACCCTTTGCAGGCAGCGGAACCCC
CCACCTGGCGACAGGTGCCTCTGCGGCCAAAAGCCACGTGTATAAGATACACCTGCAAAGGCGG
CACAACCCCAGTGCCACGTTGTGAGTTGGATAGTTGTGGAAAGAGTCAAATGGCTCTCCTCAAG
CGTATTCAACAAGGGGCTGAAGGATGCCCAGAAGGTACCCATTGTATGGGATCTGATCTGGGG
CCTCGGTGCACATGCTTTACATGTGTTTAGTCGAGGTTAAAAAAACGTCTAGGCCCCCGAACC
ACGGGGACGTGGTTTTCCTTTGAAAAACACGATGATAATATGGCCACAACCATGGTGAGCAAGG
GCGAGGAGCTGTTCACCGGGGTGGTGCCCATCCTGGTCGAGCTGGACGGCGACGTAAACGGCCA
CAAGTTCAGCGTGTCCGGCGAGGGCGAGGGCGATGCCACCTACGGCAAGCTGACCCTGAAGTTC
ATCTGCACCACCGGCAAGCTGCCCGTGCCCTGGCCCACCCTCGTGACCACCCTGACCTACGGCG
TGCAGTGCTTCAGCCGCTACCCCGACCACATGAAGCAGCACGACTTCTTCAAGTCCGCCATGCC
CGAAGGCTACGTCCAGGAGCGCACCATCTTCTTCAAGGACGACGGCAACTACAAGACCCGCGCC
GAGGTGAAGTTCGAGGGCGACACCCTGGTGAACCGCATCGAGCTGAAGGGCATCGACTTCAAGG
AGGACGGCAACATCCTGGGGCACAAGCTGGAGTACAACTACAACAGCCACAACGTCTATATCAT
GGCCGACAAGCAGAAGAACGGCATCAAGGTGAACTTCAAGATCCGCCACAACATCGAGGACGGC
AGCGTGCAGCTCGCCGACCACTACCAGCAGAACACCCCCATCGGCGACGGCCCCGTGCTGCTGC
CCGACAACCACTACCTGAGCACCCAGTCCGCCCTGAGCAAAGACCCCAACGA (SEQ ID
NO:15)

Rabbit B-globin PA:
GAAGCGCGATCACATGGTCCTGCTGGAGTTCGTGACCGCCGCCGGGATCACTCTCGGCATGGAC
GAGCTGTACAAGTAAAGCGGCCGCGATCTTTTTCCCTCTGCCAAAAATTATGGGGACATCATGA
AGCCCCTTGAGCATCTGACTTCTGGCTAATAAAGGAAATTTATTTTCATTGCAATAGTGTGTTG
GAATTTTTTGTGTCTCTCACTCGGAAGGACATATGGGAGGGCAAATCATTTAAAACATCAGAAT
GAGTATTTGGTTTAGAGTTTGGCAACATATGCCATATGCTGGCTGCCATGAACAAAGGTGGCTA
TAAAGAGGTCATCAGTATATGAAACAGCCCCCTGCTGTCCATTCCTTATTCCATAGAAAAGCCT
TGACTTGAGGTTAGATTTTTTTTATATTTTGTTTTGTGTTATTTTTTCTTTAACATCCCTAAA
ATTTTCCTTACATGTTTTACTAGCCAGATTTTCCTCCTCCTGACTACTCCCAGTCATAGCT
GTCCCTCTTCTCTTATGAAGATCCCTCGACCTGCAGCCCAAGCTTGGCGTAAT (SEQ ID
NO:16)

M13-rev:
CATGGTCATAGCTGTTTCCTGTGTGA (SEQ ID NO:17)

*Fig. 11D*

LacO:
AATTGTTATCCGCTCACAATTCCACACAACATACGAGCCGGAAGCATAAAGTGTAAAGCCTGGG
GTGCCTAATGAGTGAGCTAACTCACATTAATTGCGTTGCGCTCACTGCCCGCTTTCCAGTCGGG
AAACCTGTCGTGCCAGCGGATCCGCATCTCAATTAGTCAGCAACCATAGTCCCGCCCCTAACTC
CGCCCATCCCGCCCCTAACTCCGCCCAGTTCCGCCCATTCTCCGCCCCATGGCTGACTAATTTT
TTTTATTTATGCAGAGGCCGAGGCCGCCT (SEQ ID NO:18)

Fsel, linker:
AAACGGCCGGCCATcgataccgtcgacctcgagggggggcccggtacccagcttttgt (SEQ
ID NO:19)

T3:
Tccctttagtgagggttaattgcgcgcttggcgtaat (SEQ ID NO:20)

M13-rev:
Catggtcatagctgtttcctgtgtga (SEQ ID NO:21)

LacO:
Aattgttatccgctcacaattccacacaacatacgagccggaagcataaagtgtaaagcctggg
gtgcctaatgagtgagctaactcacattaattgcgttgcgctcactgcccgctttccagtcggg
aaacctgtcgtgccagctgcattaatgaatcggccaacgcgcggggagaggcggtttgcgtatt
gggcgctcttccgcttcctcgctcactgactcgctgcgctcggtcgttcggctgcggcgagcgg
tatcagctcactcaaaggcggtaatacggttatccacagaatcaggggataacgcaggaaagaa
catgtgagcaaaaggccagcaaaaggccaggaaccgtaaaaa (SEQ ID NO:22)

ColE1 origin:
Ggccgcgttgctggcgtttttccataggctccgcccccctgacgagcatcacaaaaatcgacgc
tcaagtcagaggtggcgaaacccgacaggactataaagataccaggcgtttccccctggaagct
ccctcgtgcgctctcctgttccgaccctgccgcttaccggatacctgtccgcctttctcccttc
gggaagcgtggcgctttctcatagctcacgctgtaggtatctcagttcggtgtaggtcgttcgc
tccaagctgggctgtgtgcacgaaccccccgttcagcccgaccgctgcgccttatccggtaact
atcgtcttgagtccaacccggtaagacacgacttatcgccactggcagcagccactggtaacag
gattagcagagcgaggtatgtaggcggtgctacagagttcttgaagtggtggcctaactacggc
tacactagaaggacagtatttggtatctgcgctctgctgaagccagttaccttcggaaaaagag
ttggtagctcttgatccggcaaacaaaccaccgctggtagcggtggtttttttgtttgcaagca
gcagattacgcgcagaaaaaaaggatctcaagaagatcctttgatcttttctacggggtctgac
gctcagtggaacgaaaactcacgttaagggattttggtcatgagattatcaaaaaggatcttca
cctagatccttttaaattaaaaatgaagttttaaatcaatctaaagtatatatgagtaaacttg
gtctgacagtta (SEQ ID NO:23)

*Fig. 11E*

AmpR:
Ccaatgcttaatcagtgaggcacctatctcagcgatctgtctatttcgttcatccatagttgcc
tgactccccgtcgtgtagataactacgatacgggagggcttaccatctggccccagtgctgcaa
tgataccgcgagacccacgctcacggctccagatttatcagcaataaaccagccagccggaag
ggccgagcgcagaagtggtcctgcaactttatccgcctccatccagtctattaattgttgccgg
gaagctagagtaagtagttcgccagttaatagtttgcgcaacgttgttgccattgctacaggca
tcgtggtgtcacgctcgtcgtttggtatggcttcattcagctccggttcccaacgatcaaggcg
agttacatgatccccatgttgtgcaaaaaagcggttagctccttcggtcctccgatcgttgtc
agaagtaagttggccgcagtgttatcactcatggttatggcagcactgcataattctcttactg
tcatgccatccgtaagatgcttttctgtgactggtgagtactcaaccaagtcattctgagaata
gtgtatgcggcgaccgagttgctcttgcccggcgtcaatacgggataataccgcgccacatagc
agaactttaaaagtgctcatcattggaaaacgttcttcggggcgaaaactctcaaggatcttac
cgctgttgagatccagttcgatgtaacccactcgtgcacccaactgatcttcagcatcttttac
tttcaccagcgtttctgggtgagcaaaaacaggaaggcaaaatgccgcaaaaaagggaataagg
gcgacacggaaatgttgaatactcatactcttcctttttcaatattattgaagcatttatcagg
gttattgtctcatgagcggatacatatttgaatgtatttagaaaaataaacaaataggggttcc
gcgcacatttccccgaaaagtgccac (SEQ ID NO:24)

*Fig. 11F*

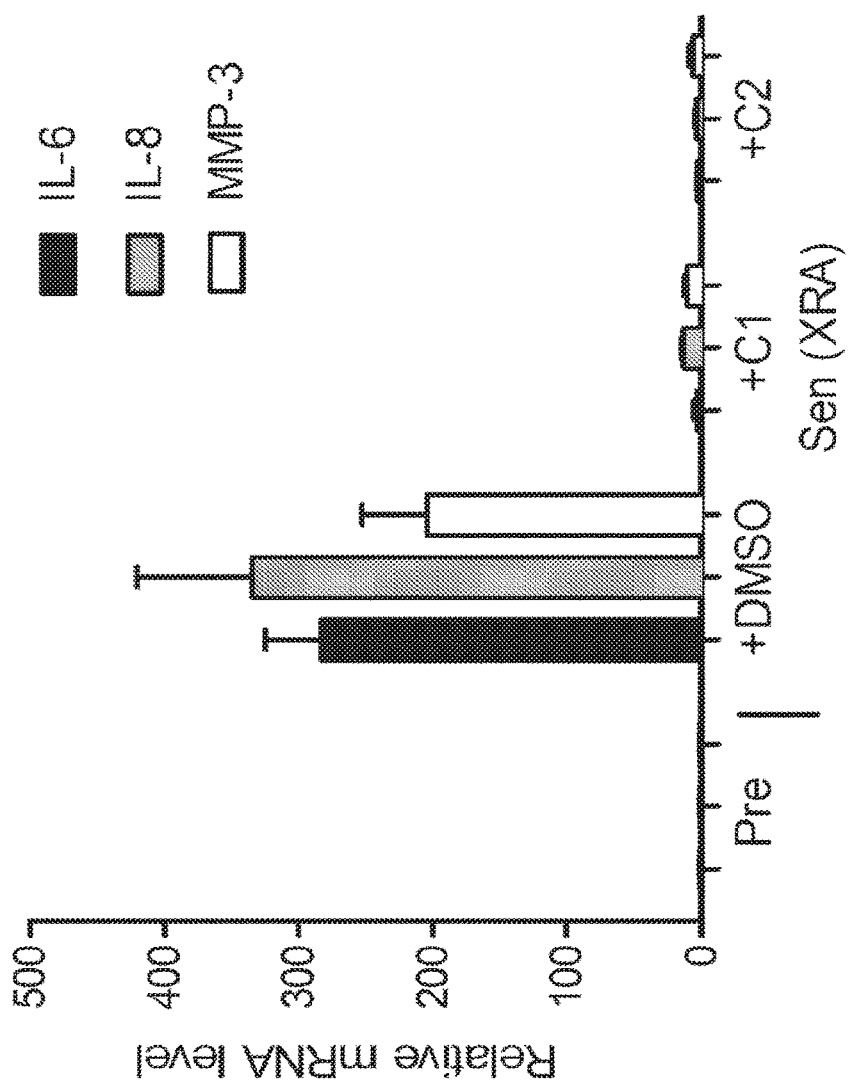
Fig. 13A1

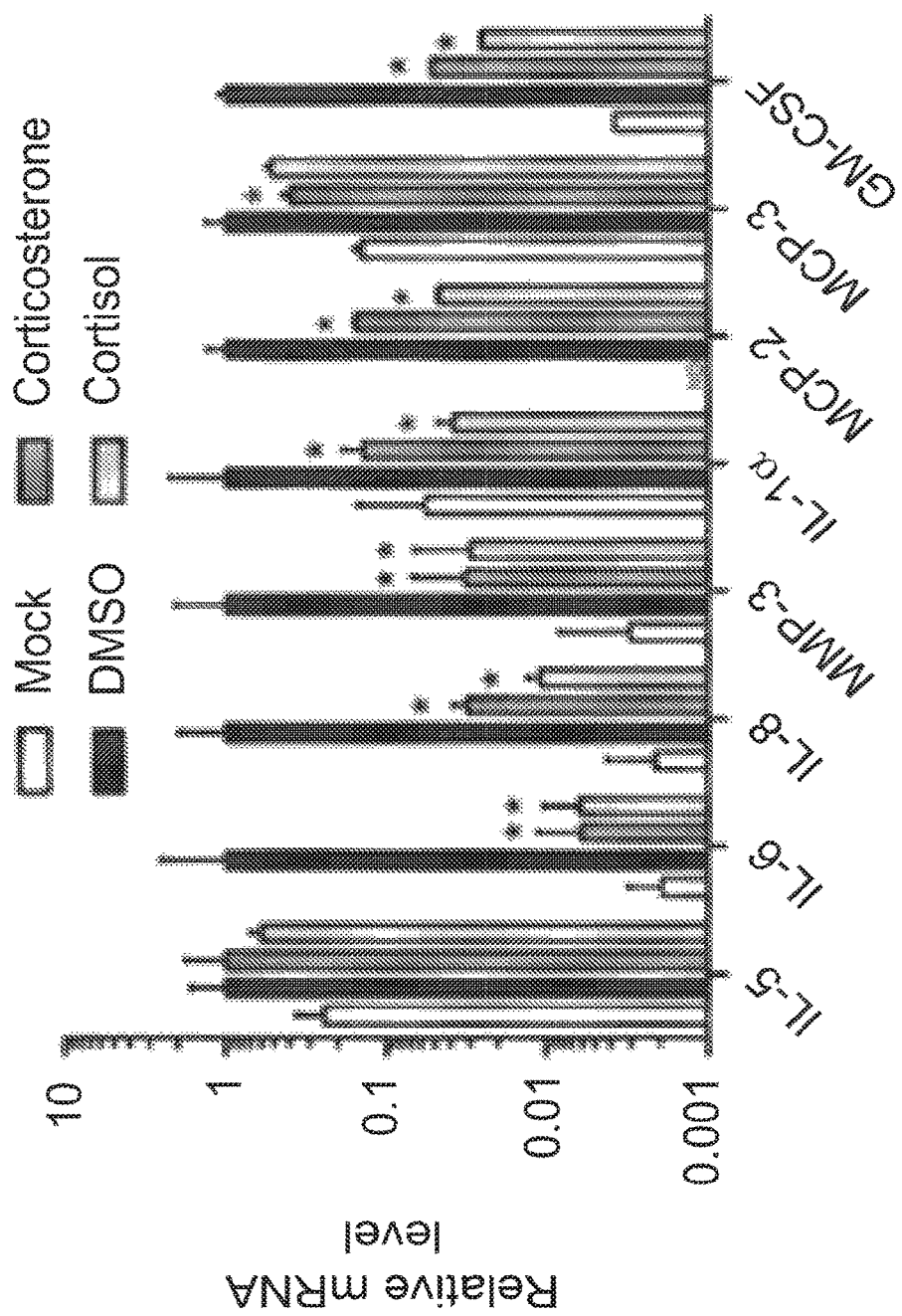
Fig. 13A2

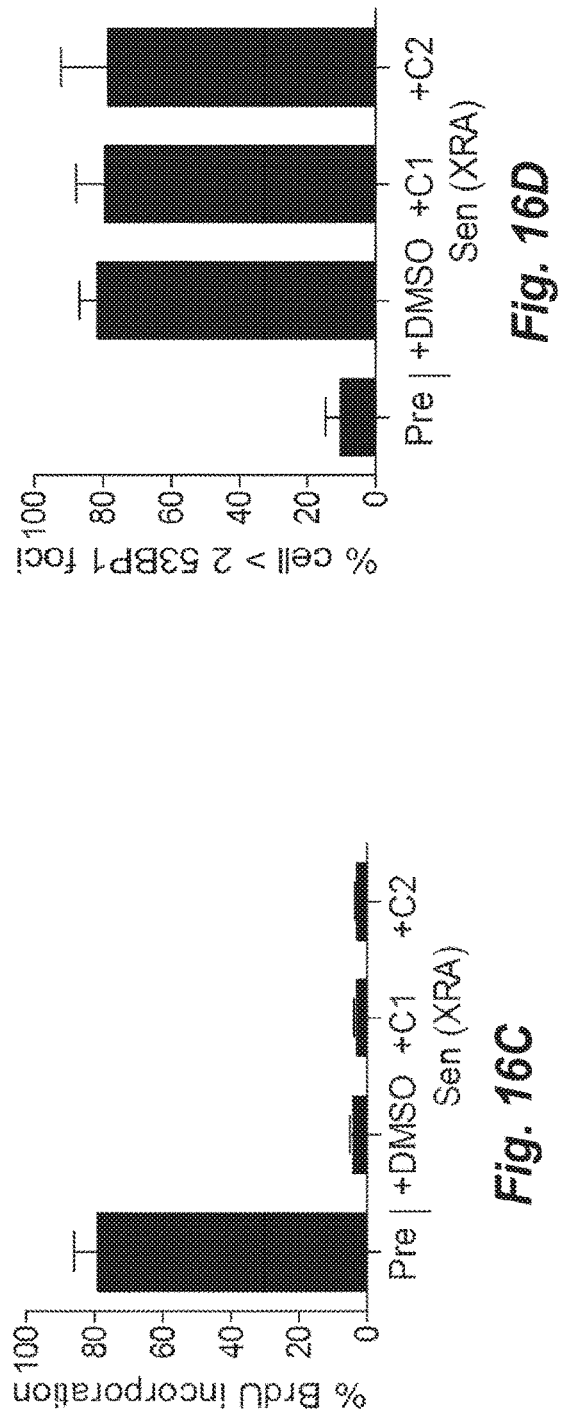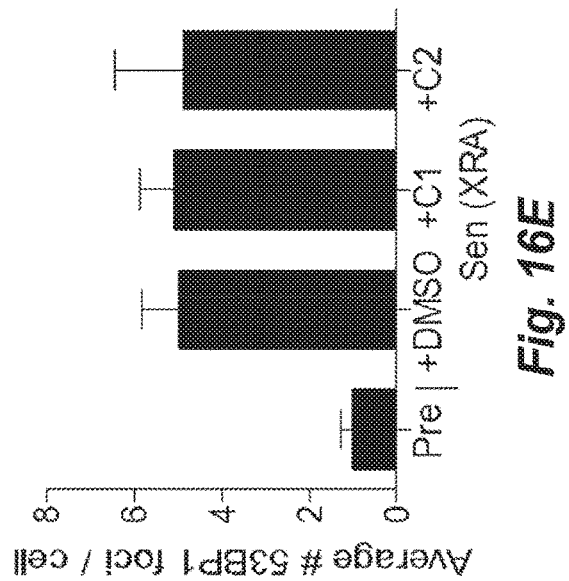

FIG. 17A
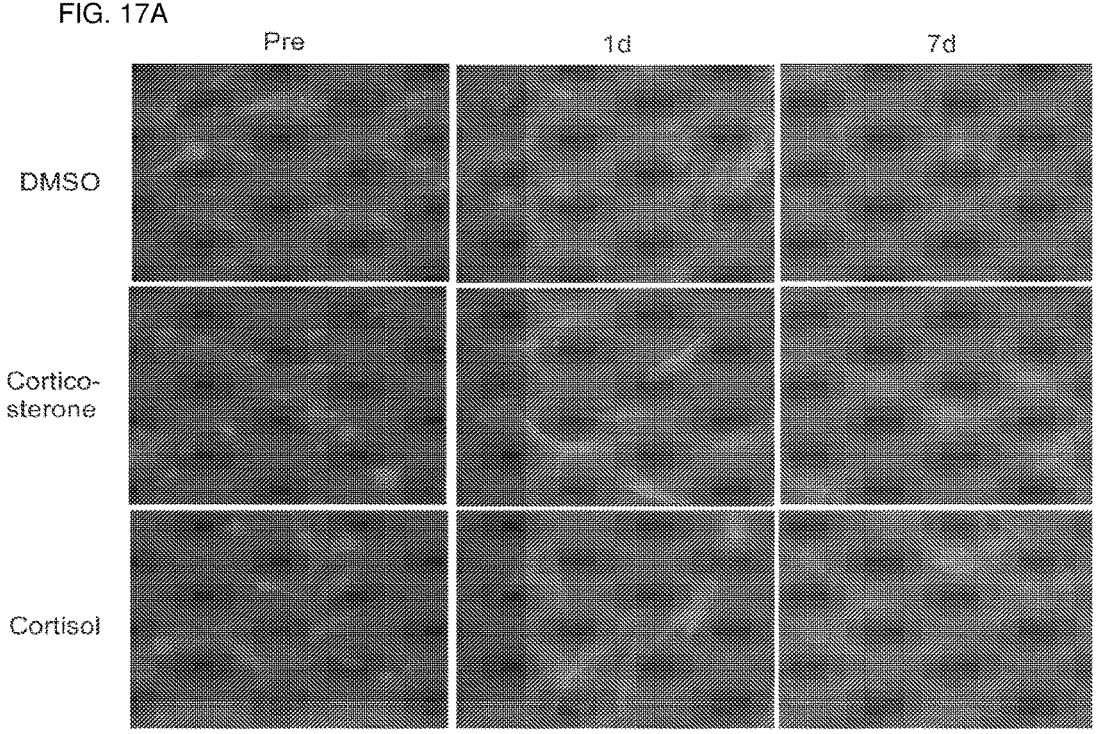
FIG. 17B
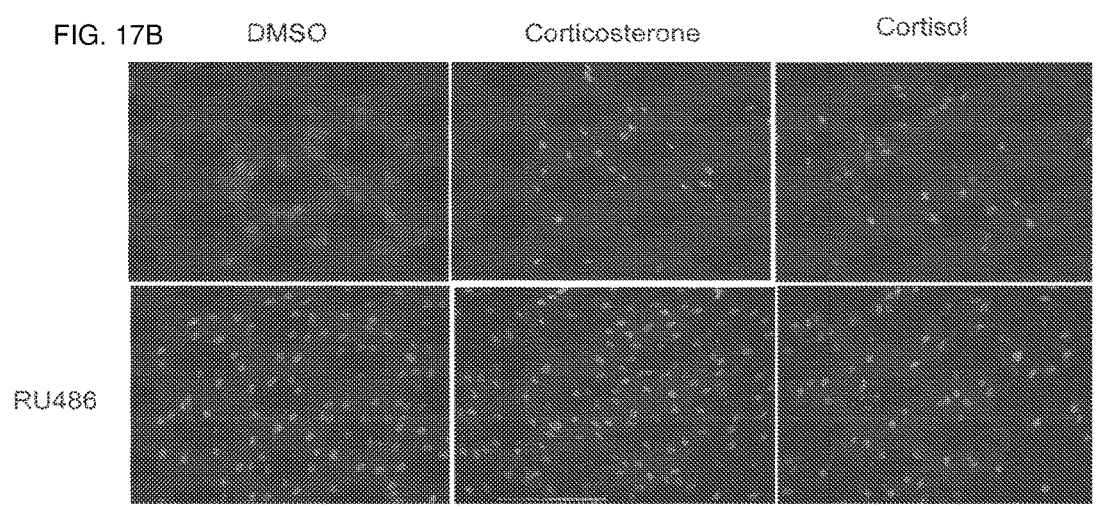
*Fig. 17*

INHIBITING ACTIVITY OF SENESCENT CELLS USING A GLUCOCORTICOID

CROSS REFERENCE TO RELATED APPLICATIONS

This application is a continuation application of U.S. application Ser. No. 14/365,040, filed Jun. 12, 2014, now abandoned, which is a U.S. National Stage Application filed under 35 U.S.C. § 371 of International Patent Application No. PCT/US2012/069601, filed Dec. 13, 2012, which claims the benefit under 35 U.S.C. § 119(e) to U.S. Provisional Application No. 61/570,166 filed Dec. 13, 2011 and U.S. Provisional Application No. 61/692,680 filed Aug. 23, 2012, which applications are incorporated by reference herein in their entirety.

STATEMENT OF GOVERNMENTAL INTEREST

This invention was made with government support under Grant Nos: AG025901, AG09909, and AG017242 awarded by the National Institutes of Health. The Government has certain rights in this invention.

STATEMENT REGARDING SEQUENCE LISTING

The Sequence Listing associated with this application is provided in text format in lieu of a paper copy, and is hereby incorporated by reference into the specification. The name of the text file containing the Sequence Listing is 200201_402WO_SEQUENCE_LISTING.txt. The text file is 30 KB, was created on Dec. 13, 2012 and is being submitted electronically via EFS-Web.

BACKGROUND

Technical Field

Methods for enhancing the effectiveness of various medical therapies used for treating diseases, such as cancer, HIV/AIDS, and autoimmune diseases, are provided herein. Agents used in these methods include agents that suppress a biological damage response.

Description of the Related Art

Cytotoxic and genotoxic therapies are administered to hundreds of thousands of patients each year for treatment of a variety of diseases, most notably, cancers. Cancer includes a broad range of diseases and affects approximately one in four individuals worldwide. In the United States, cancer is the second leading cause of death, accounting for 23% of all deaths. While the five-year relative survival rate for all cancers diagnosed is approximately 68%, treatments and their rates of success vary between cancer types. Even though chemotherapies and radiotherapies are designed to target cancer cells, the therapies can adversely affect normal cells and tissue to an extent that the beneficial effect of the cancer therapy can be significantly compromised.

Highly active anti-retroviral therapy administered to men and women who are HIV infected and have developed AIDS has contributed to extending the lifespan and improving the general health of those infected. However, this therapy can also adversely affect normal cell physiology as well.

BRIEF SUMMARY

Briefly, provided herein are methods for enhancing the effectiveness of a medical therapy by administering an agent that suppresses a biological damage response, including cellular senescence, which is inducible by the medical therapy. Provided herein are the following embodiments.

In one embodiment, a method is provided herein for enhancing the effectiveness of a medical therapy in a subject, the method comprising administering to the subject an agent that suppresses a biological damage response inducible by the medical therapy. In a specific embodiment, the method for enhancing the effectiveness of a medical therapy in a subject comprises administering to the subject an agent that suppresses a biological damage response inducible by the medical therapy, wherein the agent is administered prior to, subsequent to, or concurrent with administration of the medical therapy. In certain embodiments, the medical therapy increases the proportion of senescent cells in the subject. In another specific embodiment, a method is provided for enhancing the effectiveness of a medical therapy in a subject comprising administering to the subject an agent that suppresses a biological damage response inducible by the medical therapy, wherein the agent is administered prior to, subsequent to, or concurrent with administration of the medical therapy, wherein the agent is selected from (a) an agent that selectively destroys or facilitates selective destruction of one or more senescent cells; and (b) an agent that inhibits expression or secretion of one or more senescence cell-associated molecules produced by a senescent cell. In a specific embodiment, the agent is administered to the subject at least 3 days, at least 4 days, at least 5 days, at least 6 days, at least 7 days, at least 10 days, at least 30, at least 60, or at least 90 days subsequent to administration of the medical therapy. In a particular embodiment, the agent that suppresses the biological damage response selectively destroys or facilitates selective destruction of one or more senescent cells. In another embodiment, the agent is administered to the subject prior to administration of the medical therapy. In particular embodiments the agent is administered to the subject at least 1 day, at least 2-6 days, at least 1 week, at least 2 weeks, at least 3 weeks, at least 4-5 weeks, at least 6-8 weeks, or at least 10-12 weeks prior to administration of the medical therapy. In still another specific embodiment, the agent is administered concurrently with at least a portion of the administered medical therapy. In the embodiments described above and herein, the agent that suppresses the biological damage response inhibits expression or secretion of one or more senescence cell-associated molecules produced by a senescent cell. In a specific embodiment, the agent is a small molecule, polypeptide, peptide, antibody, antigen-binding fragment, peptibody, recombinant viral vector, or a nucleic acid. In certain embodiments, the medical therapy increases the proportion of senescent cells in a subject. In another specific embodiment, the medical therapy comprises radiation, a chemotherapy, an anti-viral therapy, or a hormone. In certain embodiments, the subject has a cancer, is in cancer remission, is at risk of developing a recurrence of a cancer, or is at risk of developing a cancer, and wherein the medical therapy comprises an anti-cancer therapy. In a more specific embodiment, the cancer comprises a solid tumor, and in other specific embodiments, the cancer comprises a liquid tumor. In other specific embodiments of the methods described above and herein, the cancer is metastatic cancer. In another particular embodiment, the methods for enhancing the effectiveness of a medical therapy described above and herein may be used when the subject has a cancer and has received or will receive a stem cell transplant, and wherein the medical therapy is high dose chemotherapy or high dose radiotherapy or a combination thereof. In particular embodiment, the stem cell transplant is an autologous or allogenic stem cell transplant.

In another particular embodiment of the methods described above and herein, the anti-viral therapy is an HIV/AIDS management therapy, wherein in one embodiment, the HIV/AIDS management therapy comprises a highly active antiretroviral therapy (HAART). In still another specific embodiment of the methods described above and herein, the subject has a cardiovascular disease or is at risk of developing a cardiovascular disease, and the medical therapy is angiotensin. In yet another specific embodiment of the methods described above and herein, the subject has diabetes, and the medical therapy is insulin.

In one embodiment, a method is provided for enhancing the effectiveness of a medical therapy in a subject comprising (a) administering to the subject the medical therapy, which medical therapy induces senescence in one or more cells of the subject; and then (b) administering to the subject an anti-senescent cell agent, which agent selectively destroys or facilitates the selective destruction of the one or more senescent cells. In a specific embodiment, the agent is administered to the subject at least 3 days, at least 4 days, at least 5 days, at least 6 days, at least 7 days, or at least 10 days, at least 30 days, at least 60 days, or at least 90 days subsequent to administration of the medical therapy. In particular embodiments, the agent is a small molecule, polypeptide, peptide, antibody, antigen-binding fragment, peptibody, recombinant viral vector, or a nucleic acid. In certain embodiments, the medical therapy increases the proportion of senescent cells in a subject. In certain embodiments, the medical therapy comprises radiation, a chemotherapy, an anti-viral therapy, or a hormone. In a specific embodiment, the subject has a cancer, is in cancer remission, is at risk of developing a recurrence of a cancer, or is at risk of developing a cancer, and wherein the medical therapy comprises an anti-cancer therapy. In another specific embodiment, the cancer comprises a solid tumor, and in yet another specific embodiment, the cancer is a liquid tumor. In other specific embodiments, the cancer is metastatic cancer. In another particular embodiment, the methods for enhancing the effectiveness of a medical therapy described above and herein may be used when the subject has a cancer and has received or will receive a stem cell transplant, and wherein the medical therapy is high dose chemotherapy or high dose radiotherapy or a combination thereof. In particular embodiment, the stem cell transplant is an autologous or allogenic stem cell transplant.

In another particular embodiment of the methods described above and herein, the anti-viral therapy is an HIV/AIDS management therapy, wherein in one embodiment, the HIV/AIDS management therapy comprises a highly active antiretroviral therapy (HAART). In still another specific embodiment of the methods described above and herein, the subject has a cardiovascular disease or is at risk of developing a cardiovascular disease, and the medical therapy is angiotensin. In yet another specific embodiment of the methods described above and herein, the subject has diabetes, and the medical therapy is insulin.

In another embodiment, is provided a use of an agent that suppresses a biological damage response inducible by a medical therapy for enhancing the effectiveness of the medical therapy, wherein the agent is suitable for administration prior to, subsequent to, or concurrent with administration of the medical therapy. In a specific embodiment, the agent is suitable for administration at least 3 days, at least 4 days, at least 5 days, at least 6 days, at least 7 days, at least 10 days, at least 30, at least 60, or at least 90 days subsequent to administration of the medical therapy. In one embodiment, the agent that suppresses the biological damage response selectively destroys or facilitates selective destruction of one or more senescent cells. In another specific embodiment, the agent is administered prior to administration of the medical therapy. In still another embodiment, the agent is administered at least 1 day, at least 2-6 days, at least 1 week, at least 2 weeks, at least 3 weeks, at least 4-5 weeks, at least 6-8 weeks, or at least 10-12 weeks prior to administration of the medical therapy. In another specific embodiment, the agent is administered concurrently with at least a portion of the administered medical therapy. In certain embodiments, the agent that suppresses the biological damage response inhibits expression or secretion of one or more senescence cell-associated molecules produced by a senescent cell. In certain embodiments, the agent is a small molecule, polypeptide, peptide, antibody, antigen-binding fragment, peptibody, recombinant viral vector, or a nucleic acid. In still another particular embodiment, the medical therapy increases the proportion of senescent cells in a subject. In one embodiment, the medical therapy comprises radiation, a chemotherapy, an anti-viral therapy, or a hormone. In another embodiment, the medical therapy is an anti-cancer therapy. In still another embodiment, the cancer comprises a solid tumor or a liquid tumor, which in certain embodiments, is metastatic cancer. In still other embodiments, the anti-viral therapy is an HIV/AIDS management therapy. In another embodiment, the HIV/AIDS management therapy comprises a highly active antiretroviral therapy (HAART). In as specific embodiment, the medical therapy is high dose chemotherapy or high dose radiotherapy or a combination thereof, which is administered prior to or subsequent to administration of a stem cell transplant. In another embodiment, the stem cell transplant is selected from (a) an autologous stem cell transplant, and (b) an allogenic stem cell transplant. In still another embodiment, the agent is useful for treating or preventing a cardiovascular disease wherein the medical therapy is angiotensin. In another embodiment, the agent is useful for treating or preventing diabetes, wherein the medical therapy is insulin.

Also provided herein is a use of an anti-senescent cell agent for enhancing the effectiveness of a medical therapy wherein the medical therapy induces senescence in one or more cells, and wherein the agent selectively destroys or facilitates the selective destruction of the one or more senescent cells.

In the following description, certain specific details are set forth in order to provide a thorough understanding of various embodiments. However, one skilled in the art will understand that the invention may be practiced without these details. In other instances, well-known structures have not been shown or described in detail to avoid unnecessarily obscuring descriptions of the embodiments. Unless the context requires otherwise, throughout the specification and claims which follow, the word "comprise" and variations thereof, such as, "comprises" and "comprising" are to be construed in an open, inclusive sense, that is, as "including, but not limited to." In addition, the term "comprising" (and related terms such as "comprise" or "comprises" or "having" or "including") is not intended to exclude that in other certain embodiments, for example, an embodiment of any composition of matter, composition, method, or process, or the like, described herein, may "consist of" or "consist essentially of" the described features. Headings provided herein are for convenience only and do not interpret the scope or meaning of the claimed embodiments.

Reference throughout this specification to "one embodiment" or "an embodiment" means that a particular feature, structure or characteristic described in connection with the embodiment is included in at least one embodiment. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

Also, as used in this specification and the appended claims, the singular forms "a," "an," and "the" include plural referents unless the content clearly dictates otherwise. Thus, for example, reference to "a non-human animal" may refer to one or more non-human animals, or a plurality of such animals, and reference to "a cell" or "the cell" includes reference to one or more cells and equivalents thereof (e.g., plurality of cells) known to those skilled in the art, and so forth. When steps of a method are described or claimed, and the steps are described as occurring in a particular order, the description of a first step occurring (or being performed) "prior to" (i.e., before) a second step has the same meaning if rewritten to state that the second step occurs (or is performed) "subsequent" to the first step. The term "about" when referring to a number or a numerical range means that the number or numerical range referred to is an approximation within experimental variability (or within statistical experimental error), and thus the number or numerical range may vary between 1% and 15% of the stated number or numerical range. It should also be noted that the term "or" is generally employed in its sense including "and/or" unless the content clearly dictates otherwise. The term, "at least one," for example, when referring to at least one compound or to at least one composition, has the same meaning and understanding as the term, "one or more."

BRIEF DESCRIPTION OF THE DRAWINGS

FIGS. 10A-10D provide a listing of an illustrative transgene selectively expressed in senescent cells, the nucleic acid sequence of a pBLUESCRIPT II KS vector containing a p16$^{Ink4a}$ promoter-FKBP-caspase-IRES-GFP nucleic acid construct (SEQ ID NO:1).

FIG. 11A-11F provide a listing of the nucleic acid sequences of FIG. 10 with the various vector components and construct components labeled.

(FIG. 12A) Senescent X-irradiated with 10 Gy (Sen (XRA)) HCA2 fibroblasts were incubated in medium plus 10% serum containing the indicated concentrations of corticosterone or the highest concentration of DMSO (vehicle control). The cells were given corticosterone or DMSO immediately after irradiation and analyzed 6 days later. The cells were washed and incubated in serum-free medium without corticosterone to generate conditioned media. Conditioned media from pre-senescent (Pre) and control or corticosterone-treated Sen (XRA) cells were analyzed by ELISA for IL-6. (FIG. 12B) Cells were treated, and conditioned media were generated and analyzed as described in (FIG. 12A) except cortisol was used at the indicated concentrations. (FIG. 12C) Conditioned media were collected from presenescent (PRE) or senescent (XRA)

cells that were treated with DMSO, corticosterone (50 nM), or cortisol (100 nM) as described in (FIG. 12A). The conditioned media were analyzed by antibody arrays. Average signal from PRE and XRA DMSO cells was used as the baseline. Signals higher than baseline are light gray (see +1 on scale to right); signals lower than baseline are dark gray as illustrated by PRE DMSO (see −1 on scale at right). Color intensities represent $log_2$-fold changes from the average value. The hierarchical clustering relationship between samples is shown as a dendrogram (left). *Factors significantly ($P<0.05$) suppressed by cortisol. ‡Factors significantly suppressed by corticosterone ($P<0.05$). (FIG. 12D) Cells were infected with RAS- or MKK6-expressing lentiviruses. After selection, the cells were given DMSO-, 500 nM corticosterone (C1) and 100 nM cortisol (C2) for 6 days. Conditioned media were generated as previously described and analyzed by ELISA for IL-6. *Factors significantly different from DMSO treatment ($P<0.05$). (FIG. 12E) Cells were treated with 500 nM corticosterone for the indicated intervals (a-d, indicated by the thick lines in the lower panel) before or after X-irradiation (XRA, indicated by the arrow). Conditioned media were prepared and analyzed by ELISA for IL-6 (upper panel). *Factors significantly different from DMSO treatment ($P<0.05$).

FIGS. 13A1-13G show the effect of glucocorticoids on the SASP depends on the glucocorticoid receptor (GR). (FIG. 13A1) mRNA was extracted from presenescent (Pre) or senescent (Sen (XRA)) HCA2 cells treated with DMSO, 500 nM corticosterone (C1) or 100 nM cortisol (C2) as described in the legend to FIG. 12. (FIG. 13A2) mRNA was extracted from presenescent (Mock) or senescent X-irradiated HCA2 cells treated with DMSO, 500 nM corticosterone, or 100 nM cortisol as described in FIG. 12. Transcripts for IL-5, IL-6, IL-8, MMP-3, IL-1α, MCP-2, MCP-3, and GM-CSF were quantified by quantitative PCR (normalized to tubulin). *Factors significantly different from DMSO treatment ($P<0.05$). (FIG. 13G) Cells were treated as described in (FIG. 13F) except for the addition of RU-486 at the indicated doses. Conditioned media were collected and analyzed by ELISA for IL-6 secretion.

(FIG. 14A) Presenescent (Pre) HCA2 cells were treated with DMSO, 500 nM corticosterone, or 100 nM cortisol for 24 hours or were induced to senesce by X-irradiation (Sen (XRA)) and given DMSO, corticosterone, or cortisol immediately thereafter. mRNA was extracted after the indicated intervals, and transcripts for IL-1α were quantified by PCR (normalized to tubulin). (FIG. 14B) mRNA extracted from cells described in (FIG. 14A) was used to quantify transcripts for IL-6 (normalized to tubulin). (FIG. 14C) Pre and Sen (XRA) cells, prepared as described in (FIG. 14A), were immunostained for IL-1α. Sen (XRA) cells were immunostained 7 days after irradiation.

(FIG. 15A) Total HCA2 cell lysates were prepared from presenescent (Pre) cells, or senescent cells (Sen (XRA)) treated with DMSO, 500 nM corticosterone (C1), or 100 nM cortisol (C2) in the absence (left panel) or presence (right panel) of recombinant IL-1α protein (rIL-1α). The lysates were analyzed by western blotting for IRAK1, IκBα, RelA, and actin (control). (FIG. 15B) After irradiation, Sen (XRA) cells were given DMSO, 50 nM corticosterone, or 100 nM cortisol. Six days later, the cells were given recombinant IL-1a protein at the indicated doses in the presence of the glucorticoids in serum free media. Conditioned media were collected 24 hours later and analyzed by ELISA for IL-6. (FIG. 15C) Nuclear extracts were prepared from Pre cells and Sen (XRA) cells treated with DMSO, 500 nM corticosterone (C1) or 100 nM cortisol (C2) as described above, and analyzed for NF-κB DNA binding activity. (FIG. 15D) Cells were infected with a lentivirus carrying an NF-κB-luciferase reporter construct, irradiated, and allowed to senesce. Immediately after irradiation cells were treated with DMSO, 500 nM corticosterone, or 100 nM cortisol, plus 0.5 µM RU-486 or 2.5 ng mL$^{-1}$ IL-1α, as indicated. Seven days after irradiation, cells were trypsinized, counted, lysed, and assayed for luciferase activity, which was normalized to cell number. (FIG. 15E) Conditioned media from presenescent (Pre) or senescent (Sen (XRA)) cells that had been treated with corticosterone (C1) or cortisol (C2) as described in FIG. 12 were prepared. The conditioned media were then assayed for ability to stimulate T47D human breast cancer cells to invade a basement membrane, as described in the Experimental Procedures. (FIG. 15F) Nuclear extracts were prepared from Pre cells, and Sen (XRA) treated cells treated with DMSO, 500 nM corticosterone, or 100 nM cortisol in the absence (left panel) or presence (right panel) of recombinant IL-1α protein (rIL-1α) and analyzed for NF-κB DNA binding activity.

FIG. 16A-16E—FIG. 16A shows IMR-90 fibroblasts that were induced to senesce by X-irradiation (10 Gy; Sen (XRA)) and treated immediately after irradiation with the indicated concentrations of corticosterone or the highest concentration of DMSO (vehicle control) for 7 days. Conditioned media from presenescent (Pre) and the control and glucocorticoid-treated Sen (XRA) cells were analyzed by ELISA for IL-6. FIG. 16B shows Sen (XRA) HCA2 cells that were treated with DMSO, 500 nM corticosterone (C1), or 100 nM cortisol (C2) for 7 days. The percentage of presenescent (Pre) and Sen (XRA) cells that express SA-Bgal were scored (upper panel). A representative field corresponding to each condition is also shown (bottom panels). FIG. 16C shows the Pre and Sen (XRA) HCA2 cells described in (B), given BrdU for 24 hours, fixed, and immunostained for nuclear BrdU staining, and then analyzed for the percentage of BrdU-positive cells. FIG. 16D shows Pre and Sen (XRA) cells described in (B) immunostained for 53BP1. The percentage of cells with >2 53BP1 nuclear foci was determined using CELL PROFILER software. At least 200 cells were analyzed per condition. FIG. 16E shows the average number of 53BP1 foci from (D), determined using the CELL PROFILER software.

FIG. 17A-17B—FIG. 17A shows presenescent (A) or Sen (Xra) HCA2 cells immunostained for the mineralocorticoid receptor. Sen (XRA) cells were given DMSO, 500 nM corticosterone, or 100 nM cortisol immediately after irradiation and immunostained 1 or 7 days thereafter. FIG. 17B shows Sen (XRA) HCA2 cells that were treated with DMSO, 500 nM corticosterone, or 100 nM cortisol in the presence or not (−) of RU486, and immunostained for the GR.

DETAILED DESCRIPTION

Figure 1B:
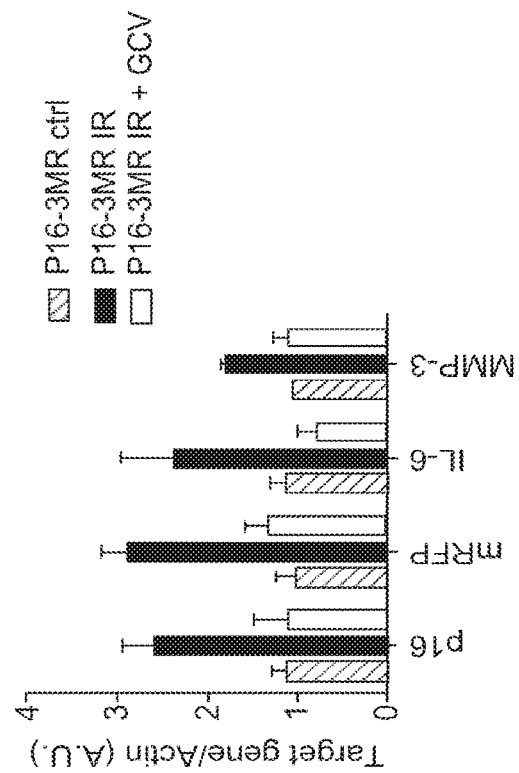
FIGS. 1A and 1B show radiation induces persistent senescent cells in p16-3MR transgenic mice and that GCV treatment leads to depletion of senescent cells and reduction of the level of several SASP (senescence associated secretory phenotype) biomarkers. The transgenic p16-3MR mice were mock irradiated (Ctrl) or irradiated (IR) (7 Gy whole body X-ray), housed for 3 months, and then treated with vehicle or GCV as described herein. Various tissues were isolated (results here shown are for lung tissue) and measured for bioluminescence (FIG. 1A) and the abundance of mRNAs encoding the p16INK4a, mRFP, IL-6 and MMP-3 proteins. Results are shown in arbitrary units (AU) after setting Ctrl levels at 1.

Provided herein are methods for enhancing the effectiveness of a medical therapy by administering an agent that suppresses a biological damage response that is inducible by the medical therapy. Medical therapies, such as cancer chemotherapy, radiation treatment, hormone therapy, and various anti-viral therapies, are intended and designed to target aberrant or abnormal cells that cause the disease, which because of aberrant metabolism, proliferation, repair capacity and/or other physiological and biological properties are presumed to be more sensitive to these therapies. However, these medical therapies, particularly those that are administered systemically, act on normal cells resulting in cell damaging, cytotoxic, and/or genotoxic effects, including inducing cellular senescence. The biological response of the damaged normal cells and tissue to the medical therapy may result in a reduction in the effectiveness of the therapy to treat the underlying disease, for example, by promoting resistance to the medical therapy and/or by exacerbating the underlying disease. Accordingly, the disclosure herein contributes to the medical art by providing methods for enhancing the effectiveness of a medical therapy by administering agents that suppress a damaging biological response.

In one embodiment, agents that suppress a biological damage response and that are useful in the methods described herein include agents (called herein anti-senescent cell agents) that (a) selectively destroy (kill, clear, remove) one or more senescent cells or that facilitate selective destruction, killing, clearance, or removal of one or more senescent cells and/or (b) suppress production and secretion of one or more senescence cell-associated molecules (e.g., by way of non-limiting example, cytokines, chemokines, growth factors, and proteases) by senescent cells. As exemplified herein, even after cellular senescence has been established in animals due to exposure to a cancer therapy, removal of senescent cells by an anti-senescent cell agent enhanced the efficacy of the therapy to inhibit tumor progression, and significantly reduced metastatic disease. Also described herein, when a biological damage response comprises induction of cellular senescence, agents that inhibit expression or secretion of senescence cell-associated molecules by the senescent cell suppress tumor cell invasiveness.

Methods for Enhancing the Effectiveness of a Medical Therapy

By suppressing the biological damage response that is inducible by the medical therapy, the suppressive agents administered to a subject in need thereof provide enhancement (i.e., improvement) of the effectiveness (i.e., efficacy) of the medical therapy. Administration of an agent that suppresses a biological damage response inducible by the therapy results in an improvement or increase of the medical therapy's therapeutic and/or prophylactic benefit compared with the benefit observed in the absence of administering the agent. In certain embodiments, enhancing the effectiveness of the medical therapy comprises suppressing the deleterious biological and physiological effects of the medical therapy.

As described herein, methods are provided for enhancing the effectiveness of a medical therapy in a subject who is in need thereof, which method comprises administering to the subject an agent capable of suppressing (i.e., reducing, decreasing, preventing, inhibiting, attenuating) a biological damage response that is inducible by exposure to the medical therapy. Agents that suppress the biological damage response may be administered to the subject prior to or subsequent to administration of the medical therapy. In certain embodiments, agents may be administered concurrently with the medical therapy. These agents include, by way of example, a small molecule, polypeptide, peptide, antibody, antigen-binding fragment, peptibody, recombinant viral vector, or a nucleic acid.

A biological damage response that is inducible by a medical therapy includes a cellular, tissue-related, and/or systemic response of the subject, which response is induced upon exposure of the treated subject to the therapy. The biological damage response inducible by the medical therapies described herein includes, but is not limited to, cellular senescence, a DNA damage response (also called herein and in the art, DDR), a tumor-promoting response in a subject who has cancer, or combinations thereof. In certain instances, when medical therapies induce cellular senescence, the proportion of senescent cells in the subject is increased. Stated another way, the number of senescent cells in the subject is greater than would be present in the subject in the absence of receiving the medical therapy.

Agents useful for suppressing a biological damage response include agents that alter the activity or physiology of a senescent cell in a manner that blunts or reduces (suppresses) the biological damage response. Agents that suppress (i.e., reduce or inhibit in a statistically or clinically significant manner) the biological damage response include those that inhibit or reduce expression and/or secretion of a polypeptide (for example, a senescence cell-associated polypeptide) that is expressed and/or up-regulated by a cell in response to a medical therapy that is cell damaging. Accordingly, such agents include those that inhibit, prevent, or disrupt a cell signaling pathway or that inhibit or reduce, or in some manner interfere with, transcription or translation or transport of the polypeptide.

In instances when the induced biological damage response comprises induction and establishment of cellular senescence, useful agents include an anti-senescent cell agent that suppresses the damage response by destroying or facilitating destruction (or clearance, killing, removal) of senescence cells. Accordingly, in a specific embodiment, methods are provided that comprise administering to the subject the medical therapy, which medical therapy induces senescence in one or more cells of the subject; and then administering to the subject an anti-senescent cell agent, which agent selectively destroys or facilitates the selective destruction of the one or more senescent cells. Also useful are agents that alter (e.g., block or inhibit) a biological activity or in some manner alter the physiology of a senescent cell such that the agent has suppressed a biological damage response. In certain embodiments, the agent inhibits the expression or secretion of one or more senescence cell-associated molecules produced by the cell.

As discussed in greater detail herein, reducing production and secretion of senescence cell-associated polypeptides may suppress a biological damage response, which with respect to a cancer, thereby reduces tumor progression and/or metastasis. Senescence cell-associated polypeptides include those described in greater detail herein and in the art that are components or molecules of a senescence associated secretory phenotype (SASP) of the senescent cell. In certain embodiments, an agent useful for suppressing a biological damage response include an agent (also called herein anti-senescent cell agents) that selectively destroys (or kills, removes, clears) one or more senescent cells or that facilitate selective destruction, killing, clearance, or removal of one or more senescent cells. In vitro cell studies indicate that senescence is established between approximately 3 to 10 days after exposure to irradiation as evidenced by the time before a SASP was established (see, e.g., Coppe et al., *PLoS Biol.* 6:2853-68 (2008); Rodier et al., *Nature Cell Biol.* 11:973-70 (2009); Laberge et al., *Aging Cell* 11(4):569-578 (2012). doi: 10.1111/j.1474-9726.2012.00818.x. Epub 2012 Apr. 17)). In particular embodiments, agents useful in the methods described herein include those capable of suppressing, inhibiting, eliminating, or reducing the biological damage response (e.g., cellular senescence) once it has been induced by exposure of cells and tissues to a medical therapy. Accordingly, in one embodiment, such an agent that suppresses this biological damage response is administered subsequent to administration of the medical therapy.

Agents useful in the methods described herein also include agents that specifically bind to and interact with a senescent cell-associated molecule to inhibit one or more biological activities of the senescent cell-associated molecule. Alternatively, an agent may bind to a cognate ligand (e.g., a cell receptor or other cell surface polypeptide, signaling molecule, secreted molecule) of a senescent cell-associated molecule thereby blocking or inhibiting binding of the senescent cell-associated molecule to its cognate ligand. This inhibition or blocking may then suppress a biologically damaging activity that would have otherwise occurred in the absence of the agent.

As discussed in greater detail herein, surprisingly, reducing production and/or secretion of polypeptides of senescent cell associated molecules characteristic of a SASP and/or reducing populations of senescent cells (characterized by a senescence associated secretory phenotype) can improve therapeutic (or prophylactic) outcome (e.g., a reduction in tumor progression and/or metastasis). In one embodiment, methods are provided for enhancing the effectiveness of a medical therapy that is a cancer therapy (e.g., irradiation, chemotherapy). As described herein, a biological damage response induced by cancer therapies, such as radiation and chemotherapy drugs, comprises cellular senescence. The presence of senescent cells promotes tumor progression, which may include promoting tumor growth and increasing size, promoting metastasis, and altering differentiation. As exemplified herein, when senescent cells are destroyed, tumor progression is significantly inhibited, resulting in tumors of small size and with little or no observed metastatic growth.

A biological damage response inducible by a medical therapy, which includes a cancer therapy (e.g., radiation or chemotherapy) includes expression of senescence cell-associated molecules. Accordingly, in certain embodiments agents useful in the methods described herein include agents that facilitate decreased production and secretion of one or more senescence cell-associated molecules, such as one or more senescence cell-associated polypeptides (e.g., by way of non-limiting example, cytokines, chemokines, growth factors, and proteases). As described in the art and in greater detail herein, the phenotype of a senescence cell, such as the phenotype referred to as senescence associated secretory phenotype (SASP), is typified by secretion of numerous cytokines (e.g., inflammatory cytokines), growth factors, extracellular matrix components (ECM) and ECM-degrading enzymes, and proteases, for example. In certain instances, such as in a subject who has cancer, secretion of these factors may be deleterious, for example, by contributing to an undesirable inflammatory response.

Agents that facilitate decreased production and secretion of one or more senescence cell-associated molecules may be administered prior to, subsequent to, or concurrently with a medical therapy that induces a biological damage response. In a particular embodiment, an agent that facilitates or causes decreased production and secretion of one or more senescence cell-associated molecules may be administered immediately after or shortly after (such as within 24, 48, or 72 hours) administration of radiotherapy or chemotherapy. By way of example, agents include glucocorticoids, such as corticosterone and cortisol, prednisone, androsterone; flavonoids (e.g., apigenin, luteolin, naringenin); tolazamide; chlorpropamide; gliclazide; finasteride; norgestrel-(−)-D; estradiol-17-beta; minoxidil; benfotiamine; calciferol; noscapine, and probucol.

As provided in the present disclosure, the glucocorticoids suppressed some (e.g., IL-6, IL-1α signaling), but not all (e.g., senescence growth arrest), of the factors that comprise the SASP. By way of background, glucocorticoids are a class of steroid hormones that includes cortisol, corticosterone, dexamethasone and related analogs, all of which have wide-ranging tissue-specific effects on metabolism and immune function (see, e.g., Gross and Cidlowski, 2008, *Trends Endocrinol. Metabl.* 19:331-339; Zanchi et al., 2010, *J. Cell. Physiol.* 224:311-315). (see, e.g., Schlossmacher et al., 2011, *J. Endocrinol.* 211:17-25). Glucocorticoids are believed to suppress inflammation by either inducing immune cell apoptosis, or by activating anti-inflammatory cytokines or repressing genes encoding pro-inflammatory cytokines, respectively. The latter activity is mediated by the ubiquitously expressed glucocorticoid receptor (GR), which exists in multiple isoforms and posttranslationally modified states (see, e.g., Zanchi et al., 2010, *J. Cell. Physiol.* 224: 311-315; Oakley and Cidlowski, 2011, *J. Biol. Chem.* 286: 3177-3184). As described herein, glucocorticoids (e.g., corticosterone and cortisol) may be clinically useful for conditions under which the SASP is thought to be harmful. For example, as described in detail herein, DNA damaging radiotherapy and chemotherapies can induce a SASP in vivo (see, e.g., Coppe et al., 2008, *PLoS Biol.* 6:2853-2868), which can have deleterious systemic effects, as well as the ability to stimulate the re-growth of tumor cells that were not eradicated by the anti-cancer therapy. The use of such agents that facilitate or cause decreased production and secretion of one or more senescence cell-associated molecules are useful in the methods described herein for suppressing a biological damage response.

In another particular embodiment, a method is provided for reducing, inhibiting, or preventing occurrence (i.e., reducing the likelihood of occurrence) or reducing severity of a deleterious side effect (which may in certain specific embodiments be associated with or result from a biological damage response) of radiotherapy or chemotherapy by administering to a subject in need thereof an agent described herein, such as an agent that inhibits expression, production, and/or secretion of one or more senescence associated molecules (e.g., a SASP factor or component). By way of example, a deleterious side effect includes but is not limited to nausea, vomiting, peripheral neuropathy, fatigue, anemia, hair loss, pain, infection, mucositis, fluid retention, diarrhea, constipation, nail or skin problems, mouth, gum or throat problems, or any side effect caused by radiotherapy or chemotherapy (see, e.g., National Cancer Institute web site).

Agents for use in the methods described herein include those that prevent (i.e., reduce the likelihood of occurrence) senescence of normal cells in the subject. Such agents may suppress or inhibit or in some manner interfere with a biological damage response include those that inhibit, prevent, or disrupt a cell signaling pathway or that inhibit or reduce, or in some manner interfere with, transcription or translation of a polypeptide or interfere with production of one or more other senescence cell associated molecules that are capable of effecting a damage response. By way of example, useful agents include an agent that in some manner facilitates reduction of IL-1α, which is an upstream regulator of the SASP. IL-1α establishes and maintains the SASP by activating the transcription factor nuclear factor-kappa B (NF-κB) (see, e.g., Orjalo et al., *Proc. Natl. Acad. Sci. USA* 106:17031-36 (2009); Freund et al., *EMBO J.* 30:1536-48 (2011)). As an additional example, also useful is an agent that inhibits expression and/or activity of (a) WNT16B, which regulates p53 activity and the PI3K/AKT pathway; (b) p16, which is a positive upstream regulator of p53; (c) ARF, which is a positive upstream regulator of pRB; (d) p21, a downstream effector of p53; (e) one or more factors that deliver mitogenic signals to oncogene pathways, for example, the RAS-RAF-MEK pathway; (f) one or more factors that stimulate the androgen receptor pathway; or an agent that inhibits production of reactive oxygen species, which can stimulate senescence associated signaling pathways.

As described herein, an agent that suppresses a biological damage response may be administered prior to (before), subsequent to (after), or concurrently with the medical therapy. In certain embodiments, when a biological damage response (including cellular senescence) has occurred, an agent is administered to a subject subsequent to administration of a medical therapy, for example, at least 2, 3, 4, 5, 6, 7, 8, 10, 30, 60, or at least 90 days or at least between 3-10 days, 10-30 days, 30-60 days or at least between 60-90 days after the subject receives the medical therapy. In a particular embodiment, the agent is administered between 2-10 days (i.e., 2, 3, 4, 5, 6, 7, 8, 9, 10) after administration of the medical therapy. Agents useful for administering after administration of the medical therapy include, by way of non-limiting example, agents that selectively destroy or facilitate selective destruction of a senescent cell (e.g., as anti-senescent cell agent). Other agents include those that block or inhibit an activity of a senescence cell associated molecule or that inhibit expression and/or secretion of a senescence cell associated molecule thereby reducing biological damage resulting from the activity of the molecule. With respect to a medical therapy regimen that includes more than one cycle of administration of the medical therapy, the agent may be administered after (subsequent to) one or more cycles of therapy, including after each cycle.

In other embodiments, methods are provided that employ agents capable of preventing or inhibiting cells from initiating a damage response or those that are capable of attenuating (i.e., reducing the severity of) the damage response upon exposure of the cells and tissue to a medical therapy. Accordingly, in one embodiment, an agent that suppresses a biological damage response is administered prior to administration of the medical therapy. In certain embodiments, such an agent is administered for example, at least 1 day, at least 2-6 days, at least 1 week, at least 2 weeks, at least 3 weeks, at least 4-5 weeks, at least 6-8 weeks, or at least 10-12 weeks prior to administration of the therapy. With respect to a medical therapy regimen that includes more than one cycle of administration of the medical therapy, the agent may be administered before (prior to) one or more cycles of therapy, including before each cycle.

Concurrent administration means that the agent is administered within 1-24 hours of administration of the medical therapy. Concurrent therapy may comprise overlapping administration of the medical therapy and the agent. In a particular embodiment, the agent is administered concurrently with a portion of the medical therapy. By way of example, administration of the agent may be administered within 1-24 hours of administration of the medical therapy and the agent is continued to be administered after the course of the medical therapy has been completed. By way of example, the agent is first administered within 1-24 hours of administration of the medical therapy, and administration of the agent is continued for an additional 1-10, 2-10, 3-10, 4-10, 5-10, 6-10, 7-10, 8-10, 9-10 or for longer than ten days (i.e., 1, 2, 3, 4, 5, 6, 7, 8, 9, or at least 10 days). Stated another way, a portion of the agent which is at least part of the total amount of agent to be delivered is administered concurrently (within 1-24 hours) of administration of the medical therapy. In certain embodiments, the agent may be administered for an extended period of time during which cellular senescence (e.g., exemplified by SASP of the cell) is being established. This therapeutic regimen may alter the secretory phenotype of a senescence cell in a manner that significantly reduces the biological damage that would otherwise occur in the absence of administering the agent. With respect to a medical therapy regimen that includes more than one cycle of administration of the medical therapy, the agent may be administered concurrent with one or more cycles of therapy, including concurrent administration with the medical therapy administration of each cycle.

Also contemplated herein are methods for enhancing the effectiveness of a medical therapy by administering at least two agents (i.e., two or more agents) that suppress a biological damage response that is inducible by a medical therapy. For convenience, the at least two agents are called herein a first agent and a second agent and together may suppress a biological damage response in an additive manner or a synergistic manner.

In another embodiment when at least two agents that suppress a biological damage response inducible by a medical therapy are administered, at least one agent (for convenience called a first agent) is an agent capable of preventing or inhibiting cells from initiating a damage response or is capable of attenuating (i.e., reducing the severity of) the damage response by cells and tissue when exposed to a medical therapy. Such agents include those described herein that prevent (i.e., reduce the likelihood of occurrence) senescence of normal cells in the subject. Accordingly, this agent is administered prior to administration of the medical therapy. At least one additional agent (called herein for convenience a second agent) is an anti-senescent cell agent that selectively destroys one or more senescent cells or that facilitates selective destruction, killing, clearance, or removal of one or more senescent cells that exist as a result of exposure to the medical therapy. The second agent is administered subsequent to administration of the medical therapy that is capable of inducing a biological damage response.

A regimen that includes administration of at least two agents may be used when a subject is in need of several cycles of a medical therapy that is a biologically damaging therapy. In one embodiment, the medical therapy is a cancer therapy, such as radiation or chemotherapy or a combination of radiation and chemotherapy. The first agent is administered prior to administration of the medical therapy at a time sufficient to permit the agent to suppress the biological damage response, for example, at least 1 day, at least 2-6 days, at least 1 week, at least 2 weeks, at least 3 weeks, at least 4-5 weeks, at least 6-8 weeks, or at least 10-12 weeks prior to administration of the therapy. The second agent is administered at least 3, 4, 5, 6, 7, 8, 10, 30, 60, or at least 90 days after the subject receives the medical therapy, for example, at a time after which cellular senescence has been induced and established. The time points at which each of the first and second agents is administered will depend on the type of therapy and the length of time between each cycle of therapy. In certain particular embodiments, first agent is administered at least 1 day, at least 2-6 days, or at least 1 week prior to administration of the medical therapy, and the second agent is administered at least 3, 4, 5, 6, 7, 8, 9, or 10 days after the subject receives the medical therapy depending on the time interval (also called the gap) between medical therapy cycles.

Biological Damage Response

A biological damage response that is inducible (i.e., that is activated, promoted, or stimulated) by a medical therapy includes a cellular, tissue-related, and/or systemic response of the subject that is induced upon exposure of the treated subject to the therapy. The biological damage response that is inducible by the medical therapies described herein includes, but is not limited to, cellular senescence, a DNA damage response (also called herein and in the art, DDR), a tumor-promoting response, and combinations thereof.

A biological damaging response inducible by senescence-inducing medical therapies can cause epigenomic disruption or genomic damage. Eroded telomeres generate a persistent DDR, which initiates and maintains the senescence growth arrest. Many senescent cells also harbor genomic damage at nontelomeric sites, which can generate the persistent DDR signaling needed for the senescence growth arrest. A biological damaging response may comprise cellular senescence in the absence of detectable DDR signaling (see, e.g., Rodier et al., *J. Cell Biol.* 192:547-56 (2011), and references cited therein). Additionally, ectopic expression of the cyclin-dependent kinase inhibitors (CDKis) that normally enforce the senescence growth arrest, notably p21WAF1 and p16INK4a, may cause senescence without an obvious DDR.

In certain embodiments, normal cells and or in addition to cells the medical therapy is intended to target (e.g., tumor cells) harmed or damaged by the medical therapy. For example, affected normal cells comprise the microenvironment around, adjacent to, or encompassing the cells and tissue that are the target(s) of the medical therapy. For example, with respect to treating a cancer, medical therapies that comprise radiation or a chemotherapy target the tumor cells; however, benign cells of the microenvironment surrounding or adjacent to the tumor (which may be either solid or liquid) may exhibit a medical therapy-induced damage response upon exposure to the therapy.

Cellular senescence is a stable and essentially permanent arrest of cell proliferation, which is accompanied by extensive changes in gene expression. Many type of cells, both normal cells and tumor cells, undergo senescence in response to stress. As described in the art, the phenotype of a senescence cell, such as the phenotype referred to as senescence associated secretory phenotype (SASP), is typified by secretion of numerous cytokines (e.g., inflammatory cytokines), growth factors, extracellular matrix components (ECM) and ECM-degrading enzymes, and proteases, for example. While proliferative arrest poses a formidable barrier to tumor progression (see, e.g., Campisi, *Curr. Opin. Genet. Dev.* 21:107-12 (2011); Campisi, *Trends Cell Biol.* 11:S27-31 (2001); Prieur et al., *Curr. Opin. Cell Biol.* 20:150-55 (2008)), and molecules secreted by senescent cells can stimulate tissue repair (see, e.g., Adams, *Molec. Cell* 36:2-14 (2009); Rodier et al., *J. Cell Biol.* 192:547-56 (2011)), senescent cells also secrete molecules that can cause inflammation (see, e.g., Freund et al., *Trends Mol. Med.* 16:238-46 (2010); Davalos et al., *Cancer Metastasis Rev.* 29:273-83 (2010)). Low-level, chronic inflammation is a hallmark of aging tissues, and inflammation is a major cause of, or contributor to, virtually every major age-related pathology, including cancer (Ferrucci et al., 2004, *Aging Clin. Exp. Res.* 16:240-243; Franceschi et al., 2007, Mech. Ageing Dev. 128:192-105; Chung et al., 2009, *Ageing Res. Rev.* 8:18-30; Davalos et al., 2010, *Cancer Metastasis Rev.* 29:273-283; Freund et al., 2010, *Trends Molec. Med.* 16:238-248). Thus, senescent cells, which increase with age and at sites of age-related pathology, might stimulate local chronic inflammation and tissue remodeling, thereby fueling both the degenerative diseases of aging as well as age-related cancer.

A senescent cell may exhibit any one or more of the following characteristics. (1) Senescence growth arrest is essentially permanent and cannot be reversed by known physiological stimuli. (2) Senescent cells increase in size, sometimes enlarging more than twofold relative to the size of nonsenescent counterparts. (3) Senescent cells express a senescence-associated β-galactosidase (SA-β-gal), which partly reflects the increase in lysosomal mass. (4) Most senescent cells express p16INK4a, which is not commonly expressed by quiescent or terminally differentiated cells. (5) Cells that senesce with persistent DDR signaling harbor persistent nuclear foci, termed DNA segments with chromatin alterations reinforcing senescence (DNA-SCARS). These foci contain activated DDR proteins and are distinguishable from transient damage foci. DNA-SCARS include dysfunctional telomeres or telomere dysfunction-induced foci (TIF). (6) Senescent cells express and may secrete molecules called herein senescent cell-associated molecules, which in certain instances may be observed in the presence of persistent DDR signaling.

Senescent cell-associated molecules include growth factors, proteases, cytokines (e.g., inflammatory cytokines), chemokines, cell-related metabolites, reactive oxygen species (e.g., $H_2O_2$), and other molecules that stimulate inflammation and/or other biological effects or reactions that may promote or exacerbate the underlying disease of the subject. Senescent cell-associated molecules include those that are described in the art as comprising the senescence-associated secretory phenotype (SASP), senescent-messaging secretome, and DNA damage secretory program (DDSP). These groupings of senescent cell associated molecules, as described in the art, contain molecules in common and are not intended to describe three separate distinct groupings of molecules. Senescent cell-associated molecules include certain expressed and secreted growth factors, proteases, cytokines, and other factors that may have potent autocrine and paracrine activities. Without wishing to be bound by theory, the negative effects of senescent cells are believed to be the result of, at least in part, the secretion of pro-inflammatory cytokines, chemokines, growth factors, and proteases that comprise the SASP of a senescent cell (see, e.g., Coppe et al., *PLoS Biol.* 6:2853-68 (2008)). Senescent cell-associated molecules that comprise the SASP can disrupt normal tissue structure and function and stimulate malignant phenotypes in pre-malignant or non-aggressive cancer cells (see, e.g., Coppe et al., supra; Coppe et al. *J. Biol. Chem.* 281:29568-74 (2006); Coppe et al. *PLoS One* 5:39188 (2010); Krtolica et al. *Proc. Natl. Acad. Sci. U.S.A.* 98:12072-77 (2001); Parrinello et al., *J. Cell Sci.* 118:485-96 (2005)). ECM associated factors include inflammatory proteins and mediators of ECM remodeling and which are strongly induced in senescent cells (see, e.g., Kuilman et al., *Nature Reviews* 9:81-94 (2009)). The factors that may have a paracrine effect on cells targeted by medical therapies, such as tumor cells, include extracellular proteins that have elevated expression in a cell after exposure to medical therapies that are genotoxic therapies (see, e.g., Sun et al., *Nature Medicine,* 18:1359-1368 (2012)). See also, e.g., Campisi, 2003, *Nature Rev. Cancer* 3:339-349 Coppé et al., 2010, *Annu. Rev. Pathol.* 5:99-118 Williams, 1957, *Evolution* 11:398-411 Collado et al., 2010, *Nature Rev. Cancer* 10:51-57 Beausejour et al., 2006, *Nature* 443:404-405 Krizhanovsky et al., 2008, *Cell* 134:657-667 Jun et al., 2010, *Nature Cell Biol.* 12:676-685 Parrinello et al., 2005, *J. Cell Sci.* 118:485-496 Acosta et al., 2008, *Cell* 133:1006-1018; Kuilman et al., 2008, *Cell* 133:1019-1031 Laberge et al., 2012, *Cancer Microenivron.* 5:39-44.

Senescence cell-associated molecules include secreted factors which may make up the pro-inflammatory phenotype of a senescent cell (e.g., SASP). These factors include, without limitation, GM-CSF, GROα, GROα,β,γ, IGFBP-7, IL-1α, IL-6, IL-7, IL-8, MCP-1, MCP-2, MIP-1α, MMP-1, MMP-10, MMP-3, Amphiregulin, ENA-78, Eotaxin-3, GCP-2, GITR, HGF, ICAM-1, IGFBP-2, IGFBP-4, IGFBP-5, IGFBP-6, IL-13, IL-1β, MCP-4, MIF, MIP-3α, MMP-12, MMP-13, MMP-14, NAP2, Oncostatin M, osteoprotegerin, PIGF, RANTES, sgp130, TIMP-2, TRAIL-R3, Acrp30, angiogenin, Axl, bFGF, BLC, BTC, CTACK, EGF-R, Fas, FGF-7, G-CSF, GDNF, HCC-4, I-309, IFN-γ, IGFBP-1, IGFBP-3, IL-1 R1, IL-11, IL-15, IL-2R-α, IL-6 R, I-TAC, Leptin, LIF, MMP-2, MSP-a, PAI-1, PAI-2, PDGF-BB, SCF, SDF-1, sTNF RI, sTNF RII, Thrombopoietin, TIMP-1, tPA, uPA, uPAR, VEGF, MCP-3, IGF-1, TGF-β3, MIP-1-delta, IL-4, FGF-7, PDGF-BB, IL-16, BMP-4, MDC, MCP-4, IL-10, TIMP-1, Flt-3 Ligand, ICAM-1, Axl, CNTF, INF-γ, EGF, BMP-6. Additional identified factors, which include those sometimes referred to in the art as senescence messaging secretome (SMS) factors, some of which are included in the listing of SASP polypeptides, include without limitation, IGF1, IGF2, and IGF2R, IGFBP3, IDFBP5, IGFBP7, PAI1, TGF-β, WNT2, IL-1α, IL-6, IL-8, and CXCR2-binding chemokines. Cell-associated molecules also include without limitation the factors described in Sun et al., *Nature Medicine,* supra, and include, for example, products of the genes, MMP1, WNT16B, SFRP2, MMP12, SPINK1, MMP10, ENPP5, EREG, BMP6, ANGPTL4, CSGALNACT, CCL26, AREG, ANGPT1, CCK, THBD, CXCL14, NOV, GAL, NPPC, FAM150B, CST1, GDNF, MUCL1, NPTX2, TMEM155, EDN1, PSG9, ADAMTS3, CD24, PPBP, CXCL3, WP3, CST2, PSG8, PCOLCE2, PSG7, TNFSF15, C17orf67, CALCA, FGF18, IL8, BMP2, MATN3, TFP1, SERPINI 1, TNFRSF25, and IL23A. Senescent cell-associated proteins also include cell surface proteins (or receptors) that are expressed on senescent cells, which include proteins that are present at a detectably lower amount or are not present on the cell surface of a non-senescent cell.

Agents that Suppress a Biological Damage Response

Agents that suppress a biological damage response include agents that reduce or inhibit the damage response to the extent that a person skilled in the art recognizes that the suppression is statistically or clinically significant. Agents capable of suppressing a biological damage response include small molecules, polypeptides, peptides, peptibodies, antibodies, antigen binding fragments (i.e., peptides and polypeptides comprising at least one complementary determining region (CDR)), recombinant viral vector, or a nucleic acid.

A therapeutic agent that "selectively" destroys or facilitates "selective" destruction of a senescent cell is an agent that preferentially (or to a greater degree) destroys or facilitates destruction or facilitates clearance or removal of a senescent cell. In other words, the therapeutic agent destroys or facilitates destruction of a senescent cell in a biologically, clinically, and/or statistically significant manner compared with its capability to destroy or facilitate destruction of a non-senescent cell. By way of non-limiting example, the therapeutic agent may directly or indirectly kill a senescent cell by disrupting the integrity of the cell membrane; inhibiting one or more metabolic processes in the cell; enhancing or stimulating a signaling pathway that leads to apoptosis or necrosis of the senescent cell; disrupt transcription or translation of genes or proteins, respectively, necessary for cell survival; or binding to the senescent cell to facilitate clearance or removal of the cell, for example, clearance by immune cells, or any combination thereof.

Also as described herein, agents that inhibit expression, secretion, or a biological activity of senescence cell associated molecule (e.g., a cytokine chemokine, growth factor, an extracellular matrix component (ECM) and ECM-degrading enzyme, and a protease) are useful in the methods described herein. In certain embodiments, the agents inhibit (reduce, decrease, prevent) production and secretion of one or more of the SASP factors (or components) described herein and known in the art. In certain embodiments, an agent that suppresses a biological damage response is one that inhibits (i.e., reduces, suppresses, prevents, blocks) production and/or secretion of at least any one or more of IL-6, IL-8, GM-CSF, MCP3, MCP2, IGF1, PDGF-BB, EGF, and BMP-4. In certain other embodiments, the agent inhibits production and/or secretion of at least any 2, 3, 4, 5, 6, 7, 8, or all of IL-6, IL-8, GM-CSF, MCP3, MCP2, IGF1, PDGF-BB, EGF, and BMP-4.

Agents of interest include those that are activated or that are pro-drugs which are converted to the active form by enzymes that are expressed at a higher level in senescent cells than in non-senescent cells. Other agents of interest include those that bind to proteins on the cell surface of a cell that are present exclusively or at a greater level on senescent cells compared with non-senescent cells. Examples of such proteins include mutant beta actin; beta-actin (ACTB) protein; drug resistance-related protein LRP; major vault protein (MVP); thyroid hormone binding protein precursor; prolyl 4-hydroxylase, beta subunit precursor (P4HB); chain A, human protein disulfide isomerase (PDI); electron-transfer-flavoprotein, beta polypeptide (ETFP); ATP synthase, H+ transporting, mitochondrial F complex, alpha subunit precursor; cathepsin B; and unnamed protein products, GI: 35655, GI: 158257194; and GI 158259937 (see, e.g., Patent Application Publication No. WO 2009/085216, Table 1, which is incorporated herein by reference in its entirety). In certain embodiments, a therapeutic agent that specifically binds to a senescent cell has at least 2, 4, 8, 10, 50, 100, or 1000 fold greater affinity for a senescent cell than for a non-senescent cell, or in certain embodiments, the agent does not detectably bind to a non-senescent cell. Peptides that specifically bind to senescent cells include 12-amino acid peptides described in PCT Patent Application Publication No. 2009/085216. A protein present at a greater level on a senescent cell than on a non-senescent cell may be a protein that is typically an intracellular protein and not detectable on the cell surface of a non-senescent cell. Other agents that suppress a biological damage response that comprises cellular senescence include those activated by a metabolic process that occurs more frequently or at a higher rate in senescent cells than in non-senescent cells.

Agents that suppress a biological damage response comprising cellular senescence include agents that directly or indirectly inhibit secretion and/or expression of a gene product that is important for senescence or that inhibit a biological activity of the gene product. Examples of these gene products are provided in the Table below; see also Sun, et al., supra.

| GENE SYMBOL | GENE PRODUCT DESCRIPTION | GenBank # | PubMed# | logFC |
|---|---|---|---|---|
| CLCA2 | CLCA family member 2, chloride channel regulator | BF003534 | 10362588, 10437792 | 4.79 |
| CLCA2 | CLCA family member 2, chloride channel regulator | NM_006536 | 10362588, 10437792 | 4.51 |
| IL33 | interleukin 53 | AB024518 | 10866975, 12477932 | 4.24 |
| CLCA2 | CLCA family member 2, chloride channel regulator | AF043977 | 10362588, 10437792 | 4.22 |
| CLCA2 | CLCA family member 2, chloride channel regulator | NM_006536 | 10362588, 10437792 | 3.87 |
| RP4-E92D3.1 | hypothetical protein LOC728621 | AW364693 | 16710787 | 3.75 |
| SYNPO2 | synaptopodin 2 | AI634580 | 6593514, 11076863 | 3.74 |
| GLS | glutaminase | AF097493 | 3531404, 6682827, 6 | 3.53 |
| ABI3BP | ABI gene family, member 3 (NESH) binding protein | NM_024801 | 11501947, 12477932, | 3.52 |
| BCHE | butyrylcholinesterase | NM_000055 | 1769657, 1769658, 2 | 3.51 |
| LOC727770 | similar to ankyrin repeat domain 20 family, member A1 | AI359676 | | 3.51 |
| DSAP | ovary-specific acidic protein | AF329088 | 12477932 | 3.44 |
| PLAT | plasminogen activator, tissue | NM_000930 | 1301152, 1310033, 1 | 3.42 |
| IL1A | interleukin 1, alpha | M15329 | 1543758, 1584804, 1 | 3.42 |
| IFIT2 | interferon-induced protein with tetratricopeptide repeats 2 | AA131041 | 1877167, 2454816, 3 | 3.39 |
| CDH10 | cadherin 10, type 2 (T2-cadherin) | NM_006727 | 2059658, 10386816 | 3.37 |
| IL1B | interleukin 1, beta | NM_000576 | 1548758, 1753956, 1 | 3.33 |
| SPATA18 | spermanogenesis associated 18 homolog (rat) | AI559300 | 12477932, 14702039 | 3.31 |
| | | AI422414 | | 3.29 |
| IL1B | interleukin 1, beta | M15330 | 1548758, 1753956, 1 | 3.29 |
| PAPPA | pregnancy-associated plasma protein A, pappalysin 1 | AI110886 | 1721035, 2412961, 2 | 3.25 |
| GLS | glutaminase | NM_014905 | 3531404, 6682827, 8 | 3.23 |
| ABI3BP | AB1 gene family, member 3 (NESH) binding protein | AB056106 | 11501947, 12477932 | 3.2 |
| SYNPO2 | synaptopodin 2 | AW009747 | 8593614, 11076863 | 3.16 |
| PAPPA | pregnancy-associated plasma protein A, pappalysin 1 | BF107618 | 1721035, 2422961, 2 | 3.14 |
| C11orf87 | chromosome 11 open reading frame 87 | AA633992 | 12477932 | 3.12 |
| PAPPA | pregnancy-associated plasma protein A, pappalysin 1 | BF107618 | 1721035, 2422961, 2 | 3.11 |
| SLC16A4 | solute carrier family 16, member 4 (monocarboxylic acid transporter 5) | NM_004696 | 8125298, 9373149, 9 | 3.1 |
| SCN2A | sodium channel, voltage-gated, type II, alpha subunit | BF432956 | 1317301, 1325650, 1 | 3.09 |
| RNF128 | ring finger protein 128 | NM_024539 | 12477932, 12705856 | 3.07 |
| AKR1C3 | aldo-keto reductase family 1, member C3 (3-alpha hydroxysteroid dehydrogenase, type II) | AB018580 | 7625489, 7650035, 7 | 3.03 |
| IL13RA2 | interleukin 13 receptor, alpha 2 | NM_000640 | 8663118, 9083087, 9 | 2.99 |
| GDF15 | growth differentiation factor 15 | AP503934 | 8125298, 9325641, 9 | 2.93 |
| SULF2 | sulfatase 2 | AL133001 | 10574462, 11549316, | 2.92 |
| KRT34 | keratin 34 | NM_021013 | 2431943, 7686952, 9 | 2.89 |
| FBXO32 | F-box protein 32 | BF244402 | 11679633, 11717410 | 2.89 |
| | | AA594609 | | 2.88 |
| | | BC043411 | | 2.88 |
| ESM1 | erdothelial cell-specific molecule 1 | NM_007036 | 8702785, 11025405 | 2.85 |
| PAPPA | pregnancy-associated plasma protein A, pappalysin 1 | AA148534 | 1711035, 2427961, 2 | 2.81 |
| MEG3 | maternally expressed 3 (non-protein coding) | AI291123 | 8619474, 9110174, 1 | 2.8 |
| C15orf48 | chromosome 15 opening reading frame 48 | AF228422 | 12209954, 12477932 | 2.79 |
| | | AK022198 | | 2.77 |
| USP53 | ubiquitin specific peptidase 53 | H25097 | 10718198, 12477932 | 2.75 |
| SDPR | serum deprivation response (phosphatidylserine binding protein) | BF982174 | 2390065, 8012384, 8 | 2.71 |
| MAP2 | microtubule-associated protein 2 | BF342661 | 1494913, 1708129, 2 | 2.69 |
| RDH10 | retinol dehydrogenase 10 (all-trans) | AW150720 | 12407145, 12477932 | 2.68 |
| BMP2 | bone morphogenetic protein 2 | AA583044 | 1487246, 2004778, 2 | 2.64 |
| CRYAB | crystallin, alpha B | AF007162 | 838078, 1407707, 15 | 2.64 |
| PAPPA | pregnancy-associated plasma protein A, pappalysin 1 | BG434272 | 1721035, 2422961, 2 | 2.64 |
| USP53 | ubiquitin specific peptidase 53 | AW188464 | 10718198, 12477932 | 2.63 |
| KRTAP1-5 | keratin associated protein 1-5 | AJ406928 | 11279113, 12228244 | 2.63 |
| H3D11B1 | hydroxysteroid (11-beta) dehydrogenase 1 | NM_005525 | 1885595, 3034894, 7 | 2.62 |
| GLS | glutaminase | AB020645 | 8531404, 6682827, 6 | 2.6 |
| ARRDC4 | arrestin domain containing 4 | AV701177 | 12477932, 14702039 | 2.59 |
| CCFL1 | chemokine (C-C motif) receptor-like 1 | NM_016557 | 8125298, 9373149, 94 | 2.58 |

| GENE SYMBOL | GENE PRODUCT DESCRIPTION | GenBank # | PubMed# | logFC |
|---|---|---|---|---|
| MAMDC2 | MAM domain containing 2 | AI862120 | 11076863, 11256614 | 2.54 |
| RTN1 | resolution 1 | NM_021136 | 7515034, 7685762, 72 | 2.52 |
| PAPPA | pregnancy-associated plasma protein A, pappalysin 1 | BG620958 | 1725035, 242961, 24 | 2.49 |
| FBXO32 | F-box protein 32 | BF244402 | 11679633, 11717410 | 2.48 |

Agents that may be used in the methods described herein include, but are not limited to, small organic molecules that suppress a biological damage response, including suppressing cellular senescence. Agents also include small molecules that destroy or facilitate destruction or removal or clearance of a senescent cell. A small molecule compound of interest may be derivatized, either randomly or by SAR, to obtain compounds with improved activity. Small organic molecules typically have molecular weights less than $10^5$ daltons, less than $10^4$ daltons, or less than $10^3$ daltons.

An agent useful in the methods described herein for enhancing the effectiveness of a medical therapy includes an antibody, or antigen-binding fragment. An antigen-binding fragment may be a fragment prepared from a whole antibody. An antigen-binding fragment also includes a peptide or polypeptide that comprises at least one complementary determining region (CDR). Useful antibodies and antigen-binding fragments include those that specifically bind to a cognate antigen that is overly expressed, selectively expressed, or only expressed by senescent cell compared with a non-senescent, normal cell. The antibody may be an internalising antibody or antigen-binding fragment that is internalized by the senescent cell via interaction with its cognate antigen. An internalizing antibody or antigen-binding fragment may be useful for delivering a cytotoxic agent to the senescent cell.

Binding properties of an antibody to its cognate antigen may generally be determined and assessed using immunodetection methods including, for example, an enzyme-linked immunosorbent assay (ELISA), immunoprecipitation, immunoblotting, countercurrent immunoelectrophoresis, radioimmunoassays, dot blot assays, inhibition or competition assays, and the like, which may be readily performed by those having ordinary skill in the art (see, e.g., Harlow et al., *Antibodies: A Laboratory Manual*, Cold Spring Harbor Laboratory (1988)). As used herein, an antibody is said to be "immunospecific," "specific for" or to "specifically bind" to a cognate antigen if it reacts at a detectable level with the antigen or immunogen. Affinities of antibodies and antigen binding fragments thereof can be readily determined using conventional techniques, for example, those described by Scatchard et al. (*Ann. N.Y. Acad. Sci. USA* 51:660 (1949)) and by surface plasmon resonance (SPR; BIAcore™, Biosensor, Piscataway, N.J.).

The antibodies may be polyclonal or monoclonal, prepared by immunization of animals and subsequent isolation of the antibody, or cloned from specific B cells according to methods and techniques routinely practiced in the art and described herein. A variable region or one or more complementarity determining regions (CDRs) may be identified and isolated from antigen-binding fragment or peptide libraries. An antibody, or antigen-binding fragment, may be recombinantly engineered and/or recombinantly produced.

An antibody may belong to any immunoglobulin class, for example IgG, IgE, IgM, IgD, or IgA and may be obtained from or derived from an animal, for example, fowl (e.g., chicken) and mammals, which include but are not limited to a mouse, rat, hamster, rabbit, or other rodent, a cow, horse, sheep, goat, camel, human, or other primate. For use in human subjects, antibodies and antigen-binding fragments are typically human, humanized, or chimeric to reduce an immunogenic response by the subject to non-human peptides and polypeptide sequences.

The antibody may be a monoclonal antibody that is a human antibody, humanized antibody, chimeric antibody, bispecific antibody, or an antigen-binding fragment (e.g., F(ab')$_2$, Fab, Fab', Fv, and Fd) prepared or derived therefrom. An antigen-binding fragment may also be any synthetic or genetically engineered protein that acts like an antibody in that it binds to a specific antigen to form a complex. For example, antibody fragments include isolated fragments consisting of the light chain variable region, Fv fragments consisting of the variable regions of the heavy and light chains, recombinant single chain polypeptide molecules (scFv proteins), and minimal recognition units consisting of the amino acid residues that mimic the hypervariable region. In certain other embodiments, antibodies are multimeric antibody fragments such as miniantibodies, bispecific and bifunctional antibodies comprising a first Fv specific for an antigen associated with a second Fv having a different antigen specificity, and diabodies and the like. Useful methodologies are described generally, for example in Hayden et al., *Curr Opin. Immunol.* 9:201-12 (1997); Coloma et al., *Nat. Biotechnol.* 15:159-63 (1997); U.S. Pat. No. 5,910,573); Holliger et al., *Cancer Immunol. Immunother.* 45:128-30 (1997); Drakeman et al., *Expert Opin. Investig. Drugs* 6:1169-78 (1997); Koelemij et al., *J. Immunother.* 22:514-24 (1999); Marvin et al., *Acta Pharmacol. Sin.* 26:649-58 (2005); Das et al., *Methods Mol. Med.* 109:329-46 (2005).

A minimal recognition unit or other antigen binding fragment may be identified from a peptide library. Such peptides may be identified and isolated from combinatorial libraries (see, e.g., International Patent Application Nos. PCT/US91/08694 and PCT/US91/04666) and from phage display peptide libraries (see, e.g., Scott et al., *Science* 249:386 (1990); Devlin et al., *Science* 249:404 (1990); Cwirla et al., *Science* 276: 1696-99 (1997); U.S. Pat. No. 5,223,409; U.S. Pat. No. 5,733,731; U.S. Pat. No. 5,498,530; U.S. Pat. No. 5,432,018; U.S. Pat. No. 5,338,665; 1994; U.S. Pat. No. 5,922,545; International Application Publication Nos. WO 96/40987 and WO 98/15833). A peptide that is a minimal recognition unit or a CDR (i.e., any one or more of the three CDRs present in a heavy chain variable region and/or one or more of the three CDRs present in a light chain variable region) may be identified by computer modeling techniques, which can be used for comparing and predicting a peptide sequence that will specifically bind to a polypeptide of interest as described herein (see, e.g., Bradley et al., *Science* 309:1868 (2005); Schueler-Furman et al., *Science* 310:638 (2005)).

Antibodies may generally be prepared by any of a variety of techniques known to persons having ordinary skill in the art. Immunogens used to immunize animals and/or to screen for antibodies of desired specificity include proteins isolated from senescent cells that, for example, are present on the cell surface of a senescent cell in greater quantity or having a different conformation than on a non-senescent cell; and senescent cell extracts, including outer membrane preparations, organelles isolated from senescent cells, and the like. Antibodies may also be identified and isolated from human immunoglobulin phage libraries, from rabbit immunoglobulin phage libraries, from mouse immunoglobulin phage libraries, and/or from chicken immunoglobulin phage libraries (see, e.g., Winter et al., *Annu. Rev. Immunol.* 12:433-55 (1994); Burton et al., *Adv. Immunol.* 57:191-280 (1994); U.S. Pat. No. 5,223,409; Huse et al., *Science* 246:1275-81 (1989); Schlebusch et al., *Hybridoma* 16:47-52 (1997) and references cited therein; Rader et al., *J. Biol. Chem.* 275: 13668-76 (2000); Popkov et al., *J. Mol. Biol.* 325:325-35 (2003); Andris-Widhopf et al., *J. Immunol. Methods* 242: 159-31 (2000)). Antibodies isolated from non-human species or non-human immunoglobulin libraries may be genetically engineered according to methods described herein and known in the art to "humanize" the antibody or fragment thereof.

Useful strategies for designing humanized antibodies may include, for example by way of illustration and not limitation, identification of human variable framework regions that are most homologous to the non-human framework regions of a chimeric antibody (see, e.g., Jones et al., *Nature* 321:522-25 (1986); Riechmann et al., *Nature* 332:323-27 (1988)). A humanized antibody may be designed to include CDR loop conformations and structural determinants of non-human variable regions, for example, by computer modeling, and then comparing the CDR loops and determinants to known human CDR loop structures and determinants (see, e.g., Padlan et al., *FASEB* 9:133-39 (1995); Chothia et al., *Nature,* 342:377-83 (1989)). Computer modeling may also be used to compare human structural templates selected by sequence homology with the non-human variable regions.

Agents such as polypeptides, peptides, peptibodies, antibodies, and antigen binding fragments (i.e., peptides or polypeptides comprising at least one antibody V region) or other agents that specifically to a senescent cell can be linked to (i.e., conjugated to, fused to, or in some manner joined to or attached to) a second agent that selectively destroys or facilitates selective destruction of senescent cells. When delivered to the senescent cell by binding of the agent to the senescent cell, the cytotoxic moiety selectively destroys the senescent cell. If the agent is recombinantly produced, a nucleotide sequence encoding the cytotoxic moiety may be linked in frame to the agent and to one or more regulatory expression sequences to produce a fusion protein comprising the agent and cytotoxic moiety. Such second agents include cytotoxic molecules, including toxins derived from plants and microorganisms, as well as small molecules do not selectively bind to senescent cells in the absence of being linked to the aforementioned antibody, polypeptide, or peptide.

An agent that suppresses a biological damage response includes a peptide-immunoglobulin (Ig) constant region fusion polypeptide, which includes a peptide-IgFc fusion polypeptide (also referred to in the art as a peptibody (see, e.g., U.S. Pat. No. 6,660,843)). The peptide may be any naturally occurring or recombinantly prepared molecule. A peptide-Ig constant region fusion polypeptide, such as a peptide-IgFc fusion polypeptide, comprises a biologically active peptide or polypeptide capable of altering the activity of a protein of interest. The Fc polypeptide may also be a mutein Fc polypeptide. Peptides that alter a biological function of a cell, such as the immunoresponsiveness of an immune cell, may be identified and isolated from combinatorial libraries (see, e.g., International Patent Application Nos. PCT/US91/08694 and PCT/US91/04666) and from phage display peptide libraries (see, e.g., Scott et al., *Science* 249:386 (1990); Devlin et al., *Science* 249:404 (1990); Cwirla et al., *Science* 276: 1696-99 (1997); U.S. Pat. No. 5,223,409; U.S. Pat. No. 5,733,731; U.S. Pat. No. 5,498,530; U.S. Pat. No. 5,432,018; U.S. Pat. No. 5,338,665; 1994; U.S. Pat. No. 5,922,545; International Application Publication Nos. WO 96/40987 and WO 98/15833).

In certain embodiments, an agent that suppresses a biological damage response is a polynucleotide or oligonucleotide that specifically hybridize to a portion of the genome or mRNA of a cell that is a senescent cell or that is in a disease microenvironment and may be induced to senescence by a biologically damaging (i.e., cell damaging) medical therapy. Polynucleotides and oligonucleotides are provided that are complementary to at least a portion of a nucleotide sequence encoding a senescent cellular polypeptide of interest (e.g., a short interfering nucleic acid, an antisense polynucleotide, a ribozyme, or a peptide nucleic acid) and that may be used to alter gene and/or protein expression. As described herein, these polynucleotides that specifically bind to or hybridize to nucleic acid molecules that encode a cellular polypeptide may be prepared using the nucleotide sequences available in the art. In another embodiment, nucleic acid molecules such as aptamers that are not sequence-specific may also be used to alter gene and/or protein expression.

Antisense polynucleotides bind in a sequence-specific manner to nucleic acids such as mRNA or DNA. Identification of oligonucleotides and ribozymes for use as antisense agents and identification of DNA encoding the genes for targeted delivery involve methods well known in the art. For example, the desirable properties, lengths, and other characteristics of such oligonucleotides are well known. Antisense technology can be used to control gene expression through interference with binding of polymerases, transcription factors, or other regulatory molecules (see Gee et al., In Huber and Carr, *Molecular and Immunologic Approaches*, Futura Publishing Co. (Mt. Kisco, N.Y.; 1994)).

Short interfering RNAs may be used for modulating (decreasing or inhibiting) the expression of a gene encoding a senescent cell-associated polypeptide. For example, small nucleic acid molecules, such as short interfering RNA (siRNA), micro-RNA (miRNA), and short hairpin RNA (shRNA) molecules may be used according to the methods described herein to modulate the expression of a cellular polypeptide of interest. A siRNA polynucleotide preferably comprises a double-stranded RNA (dsRNA) but may comprise a single-stranded RNA (see, e.g., Martinez et al. *Cell* 110:563-74 (2002)). A siRNA polynucleotide may comprise other naturally occurring, recombinant, or synthetic single-stranded or double-stranded polymers of nucleotides (ribonucleotides or deoxyribonucleotides or a combination of both) and/or nucleotide analogues as provided herein and known and used by persons skilled in the art.

In a particular embodiment, the polynucleotide or oligonucleotide may be delivered by a recombinant vector in which the polynucleotide or oligonucleotide of interest has been incorporated. In other embodiments, the recombinant viral vector may be a recombinant expression vector into which a polynucleotide sequence that encodes an antibody, an antigen-binding fragment, polypeptide or peptide that is an agent of interest is inserted such that the encoding sequence is operatively linked with one or more regulatory control sequences to drive expression of the polypeptide, antibody, an antigen-binding fragment, or peptide of interest. The recombinant vector or the recombinant expression vector may be a viral recombinant vector or a viral recombinant expression vector. Exemplary viral vectors include, without limitation, a lentiviral vector genome, poxvirus vector genome, vaccinia virus vector genome, adenovirus vector genome, adenovirus-associated virus vector genome, herpes virus vector genome, and alpha virus vector genome. Viral vectors may be live, attenuated, replication conditional or replication deficient, and typically is a non-pathogenic (defective), replication competent viral vector. Procedures and techniques for designing and producing such viral vectors are well known to and routinely practiced by persons skilled in the art.

Agents useful in the methods described herein may be identified or screened or characterized by techniques and procedures described herein and in the art. Agents that suppress a biological damage response, including those that suppress cellular senescence, may be identified by in vitro assays that employ a cell line, such as a tumor cell line. The cultured cells can be exposed to a medical therapy and a candidate agent, concurrently or in any order. Such assays may be performed in a matrix (or array) which may include a high throughput screening format. High throughput formats typically comprise automated screening of a large number of candidate agents, which may be available from synthetic or natural product libraries. The candidate agents to be screened may be organized in a high throughput screening format such as using microfluidics-based devices, or a 96-well plate format, or other regular two dimensional array, such as a 384-well, 48-well or 24-well plate format, or an array of test tubes. The format is therefore amenable to automation. An automated apparatus that is under the control of a computer or other programmable controller may be used for one or more steps of the methods described herein. A controller may monitor the results of each step of the method and may automatically alter the testing paradigm in response to those results.

Animal models may also be used to identify or characterize agents that suppress a biological response, including those that suppress cellular senescence. By way of example, non-human animals, particularly genetically modified non-human animals that comprise a transgene expressed under the control of a senescent cell-specific promoter may be used. By operably (i.e., operatively) linking a senescent cell-specific promoter of a transgene to a nucleic acid sequence encoding a polypeptide of interest (e.g., a detectable label or cytotoxicity-activating molecule), senescent cells within an animal can be monitored in a controlled and user-determined fashion (see Examples herein). An exemplary transgene comprises (1) a senescent cell-specific promoter operatively linked to a polynucleotide encoding (a) at least one detectable label, (b) a cytotoxic agent, (c) a cytotoxicity-activating molecule, (d) an RNA, or (e) any combination of (a), (b), (c) and (d); and exhibits a tumor. An exemplary animal model includes a transgene comprising (a) a p16$^{Ink4a}$ promoter operatively linked to a polynucleotide sequence encoding a FKBP-caspase fusion polypeptide (p16-FKBP-caspase transgene) and to a polynucleotide sequence encoding a green fluorescent protein (see, e.g., Baker et al., Nature 479:232-36 (2011), which is incorporated herein by reference in its entirety); or (b) a p16$^{Ink4a}$ promoter operatively linked to a polynucleotide sequence encoding a fusion polypeptide comprising a luciferase, a red fluorescent protein, and a truncated herpes simplex virus thymidine kinase (tTK) (p16-3MR transgene), which may be called herein a trimodal fusion protein (3MR). In certain transgenic animals, the luciferase is a renilla luciferase and red fluorescent protein is a monomeric red fluorescent protein.

Any of a number of cytotoxicity-activating molecules may be operably linked to a senescent cell-specific promoter to produce a suitable transgene for use in the animal model. Following its expression in a senescent cell-specific fashion, the cytotoxicity-activating molecule is one that is capable of inducing the controllable killing of the senescent cells in which it is expressed upon administration of an activating agent to the transgenic animal. Illustrative examples of cytotoxicity-activating molecules include herpes simplex virus (HSV) thymidine kinase (TK) polypeptides and FK506 binding protein (FKBP) (or variant thereof)-caspase fusion polypeptide. By way of an additional example, the cytotoxicity-activating molecule encoded by the transgene is a herpes simplex virus (HSV) thymidine kinase (TK) polypeptide (including truncated TK polypeptides) and the activating agent is the pro-drug ganciclovir, which is converted to a toxic moiety that is lethal to the cell in which it is expressed.

Effectiveness of an agent to suppress a biological damage response can be evaluated in such an animal model in which the agent's capability to suppress cellular senescence can be determined. An agent that suppresses cellular senescence may as a consequence inhibit tumor proliferation in the animal model. Tumor proliferation may be determined by tumor size, which can be measured in various ways familiar to a person skilled in the tumor animal model art, such as by palpation or measurement of the volume or area of a tumor (which may be performed postmortem), location(s) of the tumor (e.g., to determine if tumor cells have metastasized from the primary tumor site (i.e., the site where the tumor cells initially colonize). The effect of the therapeutic agent on tumor proliferation may also be evaluated by examining differentiation of the tumor cells.

Senescent cells and senescent cell associated molecules can be detected by techniques and procedures described in the art. For example, senescent cells, including senescent cells obtained from tissues can be analyzed by histochemistry or immunohistochemistry techniques that detect the senescence marker, SA-beta gal (SA-Bgal) (see, e.g., Dimri et al., Proc. Natl. Acad. Sci. USA 92: 9363-9367 (1995). The presence of the senescent cell-associated polypeptide p16 can be determined by any one of numerous immunochemistry methods practiced in the art, such as immunoblotting analysis. Expression of nucleic acids encoding senescent cell associated polypeptides, including p16 mRNA, in a cell can be measured by a variety of techniques practiced in the art including quantitative PCR. The presence and level of senescence cell associated polypeptides (e.g., polypeptides of the SASP) can be determined by using automated and high throughput assays, such as an automated Luminex array assay described in the art (see, e.g., Coppe et al., PLoS Biol 6: 2853-68 (2008)). For monitoring a biological damage response that comprises a DNA damage response, the various DNA damage response indicators can be detected, for example, according to the method of Rodier et al., Nature Cell Biol 11: 973-979 (2009)).

The present disclosure also provides in vitro methods of identifying and characterizing an agent that selectively inhibits senescence associated secretory phenotype (SASP), the method comprising: contacting (i.e., mixing, combining or in some manner promoting interaction between) senescent cells and quiescent (non-senescent) cells with one or more test agents (i.e., candidate agents); determining the level of production of one or more components characteristic of SASP by the senescent cells and by the quiescent cells. Each of the steps of the methods described herein are performed under conditions and for a time sufficient appropriate for each step. Such conditions and time are discussed herein and in the exemplary methods provided in the examples, and which may be readily determined by persons skilled in the art.

For example, the level of SASP molecules, such as cytokines (e.g., inflammatory cytokines), growth factors, extracellular matrix components (ECM) and ECM-degrading enzymes, and proteases secreted by each of the senescent cells and the quiescent cells is determined and compared. A test agent that reduces production of one or more of the SASP components without causing gross cellular toxicity and without inducing SASP in the quiescent cells is an agent that selectively inhibits the senescence associated secretory phenotype. By selecting test agents without gross cellular toxicity, compounds that lowered SASP components via cell death may be excluded. Various methods of measuring cellular toxicity (or cell viability) are known in the art, and include, for example, methods for assessing cell membrane integrity (trypan blue or propidium iodide), lactate dehydrogenase assay, MTT or MTS assay, ATP assay, sulforhodamine B assay, and WST assay. In certain embodiments, gross cellular toxicity or cell viability may be measured by detecting ATP levels.

In certain embodiments the selecting a test agent step comprises: selecting a test agent that reduces the production of one or more of the SASP components without gross cellular toxicity and without inducing SASP in the quiescent cells, and without reversing the senescence growth arrest, as a candidate agent that selectively inhibits the senescence associate secretory phenotype.

In certain embodiments, the one or more senescence associated components characteristic of the SASP is a secreted senescence associated molecule. In certain embodiments, the one or more molecules characteristic of the SASP include any one or more of the SASP factors described herein and know in the art. In certain embodiments, an agent of interest used in the methods described herein for suppressing a biological damage response is one that inhibits (i.e., reduces, suppresses, prevents, blocks) production and/or secretion of any one or more of IL-6, IL-8, GM-CSF, MCP3, MCP2, IGF1, PDGF-BB, EGF, and BMP-4. In certain other embodiments, the agent of interest inhibits production and/or secretion of at least any 2, 3, 4, 5, 6, 7, 8, or all of IL-6, IL-8, GM-CSF, MCP3, MCP2, IGF1, PDGF-BB, EGF, and BMP-4. In certain embodiments, the agent of interest inhibits production and/or secretion of one of more components characteristic of SASP, wherein the one of more components characteristic of SASP comprise IL-6.

Production of components characteristic of SASP may be measured by a variety of methods. In certain embodiments, the components characteristic of SASP may be measured in medium in which the cells have been cultured. The medium may be conditioned medium, where following treatment of cells with a test agent, cells are washed and incubated in serum-free medium without the presence of the test agent for a period of time to generate conditioned medium. The presence and level of senescence cell associated molecules (e.g., polypeptides of the SASP) can be determined by using automated and high throughput assays, such as an automated Luminex array assay described in the art (see, e.g., Coppe et al., *PLoS Biol* 6: 2853-68 (2008)). In certain embodiments, components characteristic of SASP are measured using an immunoassay, including, for example, Western blot, ELISA, antibody array, later flow immunoassay, magnetic immunoassay, radioimmunoassay, FACS, and a Surround Optical Fiber Immunoassay (SOFIA).

In certain embodiments, the method of identifying or characterizing a compound that selectively inhibits SASP is a high throughput screening method. High throughput screening, typically automated screening, of a large number of candidate therapeutic agents from synthetic or natural product libraries may be used to identify therapeutic agents. The agents may be approved or pre-clinical compounds. The candidate therapeutic agents to be screened may be organized in a high throughput screening format such as using microfluidics-based devices, or a 96-well plate format, or other regular two dimensional array, such as a 1536 well, 384-well, 48-well or 24-well plate format, or an array of test tubes. The format is therefore amenable to automation. An automated apparatus that is under the control of a computer or other programmable controller may be used for one or more steps of the methods described herein. A controller may monitor the results of each step of the method and may automatically alter the testing paradigm in response to those results. It is apparent to one of skill in the art that a variety of screening formats may be employed, e.g., different test agents may be placed in different vessels or wells, or a plurality of test agents are polled in a single well or vessel, or a combination thereof.

In certain embodiments, senescent cells and quiescent (i.e., non-senescent) cells used in the methods of identifying a compound that selectively inhibits SASP disclosed herein comprise fibroblasts. In a specific embodiment, the cells comprise human fibroblasts. In certain embodiments, methods of identifying a compound that selectively inhibits SASP as described herein may comprise performing and/or repeating the method using one or more fibroblast cell lines and/or primary fibroblasts from the same or different species. In certain other embodiments, the methods of identifying a compound that selectively inhibits SASP as described herein may be performed and/or repeated using two, three, four or more fibroblast cell lines and/or fibroblast primary sources from the same or different species.

For maintaining viability of cells, including fibroblast and tumor cells, the cells are cultured in media and under conditions practiced in the art for proper maintenance of cells in culture, including media (with or without antibiotics) that contains buffers and nutrients (e.g., glucose, amino acids (e.g., glutamine), salts, minerals (e.g., selenium)) and also may contain other additives or supplements (e.g., fetal bovine serum or an alternative formulation that does not require a serum supplement; transferrin; insulin; putrescine; progesterone) that are required or are beneficial for in vitro culture of cells and that are well known to a person skilled in the art (see, for example, GIBCO media, INVITROGEN Life Technologies, Carlsbad, Calif.). Similar to standard cell culture methods and practices, the cell cultures described herein are maintained in tissue culture incubators designed for such use so that the levels of carbon dioxide (typically 5%), humidity, and temperature can be controlled. The cell culture system may also comprise addition of exogenous (i.e., not produced by the cultured cells themselves) cell growth factors, which may be provided, for example, in the media or in a substrate or surface coating. Growth characteristics of the cells for use in the methods described herein, may be optimized by altering the composition or type of media, adjusting the amount of one or more nutrients and/or serum, which are procedure with which a skilled artisan is familiar. Persons skilled in the tissue culture art also recognize that conditions employed for routine maintenance of a cell culture (i.e., media, additives, nutrients) may need to be adjusted appropriately for certain manipulations of the cells such as ensuring appropriate confluency and growth properties of cells for the techniques described herein including high throughput screening.

In certain embodiments, senescent cells used in the methods of identifying or characterizing a compound that selectively inhibits SASP disclosed herein are induced to senescence by exposure to radiation (e.g., X-irradiation), exposure to a chemotherapeutic (e.g., doxorubicin), or transfection with a nucleic acid construct that expresses one or more proteins that induce senescence, such as oncogenic proteins (e.g., MAPK-6, RAS, MYC, ERK, TRK, MINT). In certain embodiments, the senescent cells comprise cells transfected with a construct that expresses MAPK-6 or RAS.

In certain embodiments, the method further comprises testing the ability of the test agent to reduce/suppress/or inhibit the ability of treated senescent cells to stimulate tumor invasion. Tumor cell invasion is one of the hallmarks of metastatic phenotype. The effect of a test agent may be evaluated by its ability to suppress a deleterious property of SASP, the ability of SASP to stimulate tumor invasion. Various tumor invasion assays are known in the art, and include, for example, the Boyden chamber assay and modifications thereof (see, e.g., Albini et al., 1987, Cancer Res. 47:3239; Shaw, 2005, *Methods Mol. Biol.* 294:97-105; Nicolson, 1982, *J. Histochem. Cytochem.* 30:214-220; Rapesh, 1989, *Invasion & Metastasis* 9:192-208).

A person skilled in the art will readily appreciate that the methods of characterizing and identifying the agents of interest described here may employ equipment, computers (and computer readable medium), and the like that are routinely used for performing steps of the method (e.g., washing, adding reagents and the like) and processing the data. Analytical tools, such as statistical analyses, are also routinely used by the skilled person.

Diseases and Medical Therapies

Diseases and Subjects in Need of Treatment

A subject (i.e., patient) in need of the therapeutic methods described herein is a human or non-human animal. The subject in need of medical therapies with enhanced efficacy may exhibit symptoms or sequelae of a disease described herein or may be at risk of developing the disease. Non-human animals that may be treated include mammals, for example, non-human primates (e.g., monkey, chimpanzee, gorilla, and the like), rodents (e.g., rats, mice, gerbils, hamsters, ferrets, rabbits), lagomorphs, swine (e.g., pig, miniature pig), equine, canine, feline, bovine, and other domestic, farm, and zoo animals.

A subject who may receive an agent that suppresses a biological damage response includes a subject who has a cancer or who is at risk of developing cancer. Subjects who have cancer also include a subject who is in remission (also called cancer remission herein), whether partial or complete. Remission refers to a decrease in or disappearance of signs and symptoms of cancer. In partial remission, some but not all, signs and symptoms of cancer have disappeared. In complete remission, all signs and symptoms of cancer have disappeared and if cancer cells remain, they are not detectable. Subjects who are in remission, either partial or complete, and who have a risk of cancer recurrence may benefit from the methods described herein.

Patients who are at risk of developing a cancer include those who have one or more genetic mutations that increase the likelihood that the subject will develop the cancer. By way of example, human genes BRCA1 and BRCA2 belong to a class of genes known as tumor suppressors. Mutation(s) of these genes has been linked to hereditary breast and ovarian cancer. BRCA1 mutations may also increase a woman's risk of developing colon, uterine, cervical, and pancreatic cancer. Certain mutations in BRCA2 also increase the risk of pancreatic cancer as well as stomach cancer, gallbladder and bile duct cancer, and melanoma. Men with certain BRCA1 mutations and/or BRCA2 mutations also have an increased risk of breast cancer and, and, possibly, of pancreatic cancer, testicular cancer, and early-onset prostate cancer. Subjects at risk of developing a cancer also include those who have xeroderma pigmentosum that results from mutations in XPD helicase, which is required for nucleotide excision repair.

As used herein and in the art, the terms cancer or tumor are clinically descriptive terms which encompass diseases typically characterized by cells that exhibit abnormal cellular proliferation. The term cancer is generally used to describe a malignant tumor or the disease state arising from the tumor. Alternatively, an abnormal growth may be referred to in the art as a neoplasm. The term tumor, such as in reference to a tissue, generally refers to any abnormal tissue growth that is characterized, at least in part, by excessive and abnormal cellular proliferation. A tumor may be metastatic and capable of spreading beyond its anatomical site of origin and initial colonization to other areas throughout the body of the subject. A cancer may comprise a solid tumor or may comprise a liquid tumor (e.g., a leukemia).

The methods described herein may be useful for enhancing the effectiveness of a medical therapy that is a cancer therapy in a subject who has any one of the types of tumors described in the medical art. Types of cancers (tumors) include the following: adrenocortical carcinoma, childhood adrenocortical carcinoma, aids-related cancers, anal cancer, appendix cancer, basal cell carcinoma, childhood basal cell carcinoma, bladder cancer, childhood bladder cancer, bone cancer, brain tumor, childhood astrocytomas, childhood brain stem glioma, childhood central nervous system atypical teratoid/rhabdoid tumor, childhood central nervous system embryonal tumors, childhood central nervous system germ cell tumors, childhood craniopharyngioma brain tumor, childhood ependymoma brain tumor, breast cancer, childhood bronchial tumors, carcinoid tumor, childhood carcinoid tumor, gastrointestinal carcinoid tumor, carcinoma of unknown primary, childhood carcinoma of unknown primary, childhood cardiac (heart) tumors, cervical cancer, childhood cervical cancer, childhood chordoma, chronic myeloproliferative disorders, colon cancer, colorectal cancer, childhood colorectal cancer, extrahepatic bile duct cancer, ductal carcinoma in situ (dcis), endometrial cancer, esophageal cancer, childhood esophageal cancer, childhood esthesioneuroblastoma, eye cancer, malignant fibrous histiocytoma of bone, gallbladder cancer, gastric (stomach) cancer, childhood gastric (stomach) cancer, gastrointestinal stromal tumors (gist), childhood gastrointestinal stromal tumors (gist), childhood extracranial germ cell tumor, extragonadal germ cell tumor, gestational trophoblastic tumor, glioma, head and neck cancer, childhood head and neck cancer, hepatocellular (liver) cancer, hypopharyngeal cancer, kidney cancer, renal cell kidney cancer, Wilms tumor, childhood kidney tumors, Langerhans cell histiocytosis, laryngeal cancer, childhood laryngeal cancer, leukemia, acute lymphoblastic leukemia (all), acute myeloid leukemia (aml), chronic lymphocytic leukemia (cll), chronic myelogenous leukemia (cml), hairy cell leukemia, lip cancer, liver cancer (primary), childhood liver cancer (primary), lobular carcinoma in situ (lcis), lung cancer, non-small cell lung cancer, small cell lung cancer, lymphoma, aids-related lymphoma, burkitt lymphoma, cutaneous t-cell lymphoma, Hodgkin lymphoma, non-Hodgkin lymphoma, primary central nervous system lymphoma (cns), melanoma, childhood melanoma, intraocular (eye) melanoma, Merkel cell carcinoma, malignant mesothelioma, childhood malignant mesothelioma, metastatic squamous neck cancer with occult primary, midline tract carcinoma involving NUT gene, mouth cancer, childhood multiple endocrine neoplasia syndromes, mycosis fungoides, myelodysplastic syndromes, myelodysplastic neoplasms, myeloproliferative neoplasms, multiple myeloma, nasal cavity cancer, nasopharyngeal cancer, childhood nasopharyngeal cancer, neuroblastoma, oral cancer, childhood oral cancer, oropharyngeal cancer, ovarian cancer, childhood ovarian cancer, epithelial ovarian cancer, low malignant potential tumor ovarian cancer, pancreatic cancer, childhood pancreatic cancer, pancreatic neuroendocrine tumors (islet cell tumors), childhood papillomatosis, paraganglioma, paranasal sinus cancer, parathyroid cancer, penile cancer, pharyngeal cancer, pheochromocytoma, pituitary tumor, plasma cell neoplasm, childhood pleuropulmonary blastoma, prostate cancer, rectal cancer, renal pelvis transitional cell cancer, retinoblastoma, salivary gland cancer, childhood salivary gland cancer, ewing sarcoma family of tumors, Kaposi Sarcoma, osteosarcoma, rhabdomyosarcoma, childhood rhabdomyosarcoma, soft tissue sarcoma, uterine sarcoma, sézary syndrome, childhood skin cancer, nonmelanoma skin cancer, small intestine cancer, squamous cell carcinoma, childhood squamous cell carcinoma, testicular cancer, childhood testicular cancer, throat cancer, thymoma and thymic carcinoma, childhood thymoma and thymic carcinoma, thyroid cancer, childhood thyroid cancer, ureter transitional cell cancer, urethral cancer, endometrial uterine cancer, vaginal cancer, vulvar cancer, Waldenström Macroglobulinemia.

Cancers that are liquid tumors are classified in the art as those that occur in blood, bone marrow, and lymph nodes and include generally, leukemias (myeloid and lymphocytic), lymphomas (e.g., Hodgkin lymphoma), and melanoma (including multiple myeloma). Leukemias include for example, acute lymphoblastic leukemia (ALL), acute myeloid leukemia (AML), chronic lymphocytic leukemia (CLL), chronic myelogenous leukemia (CML), and hairy cell leukemia. Cancers that are solid tumors and occur in greater frequency in humans include, for example, melanoma, prostate cancer, testicular cancer, breast cancer, brain cancer, pancreatic cancer, colon cancer, thyroid cancer, stomach cancer, lung cancer, ovarian cancer, Kaposi's sarcoma, skin cancer (including squamous cell skin cancer), renal cancer, head and neck cancers, throat cancer, squamous carcinomas that form on the moist mucosal linings of the nose, mouth, throat, etc.), bladder cancer, osteosarcoma (bone cancer), cervical cancer, endometrial cancer, esophageal cancer, liver cancer, and kidney cancer. The methods described herein are also useful for enhancing the effectiveness of a medical therapy that is a cancer therapy to prevent (i.e., reduce the likelihood of occurrence), inhibit, retard or slow progression of metastatic cancer.

Methods for enhancing the effectiveness of a medical therapy may also be administered to a subject who is HIV infected, including patients who have developed AIDS. Also as described herein, a subject who has diabetes and receives insulin or a patient who has a condition that is treatable by administering angiotensin as a medical therapy may benefit by receiving an agent that suppresses a biological damage response.

Medical Therapies

Medical therapies that induce, cause, or promote a biological damage response include genotoxic (e.g., DNA damaging) and cytotoxic therapies. Examples of such medical therapies include most therapies used for treating cancers, such as radiation and a wide range of chemicals (i.e., chemotherapies). Radiation and chemotherapies are cytotoxic agents that selectively target cancer cells (i.e., tumor cells) by exploiting differential characteristics of the tumor cell compared with a normal cell. By way of example, differential characteristics and properties of tumor cells include high proliferation rates, hypoxia, aberrant metabolism, less effective repair capacity, and genomic instability.

Radiation therapy comprises use of high-energy radiation to shrink tumors and to kill cancer cells by damaging their DNA. Radiation includes X-rays, gamma rays, and charged particles. The radiation may be delivered by a machine outside the body (e.g., external-beam radiation therapy) or the radioactive material placed in the body near cancer cells (i.e., internal radiation therapy, also called brachytherapy, which may be used, for example, in treating breast cancer and prostate cancer). Radiation therapy also includes systemic radiation therapy that uses radioactive substances, such as radioactive iodine (e.g., for treating thyroid cancer), that is administered systemically (for example, parenterally or orally).

Radiation therapy may be given with the intent to cure a cancer, for example, by eliminating a tumor or preventing cancer recurrence, or both. In such instances, radiation therapy may be used alone or in combination with surgery, chemotherapy, or with both surgery and chemotherapy. Radiation therapy may also be administered to have a palliative effect, for example to relieve symptoms (e.g., to shrink tumors of the brain, shrink tumors pressing on the spine or in bone, shrink tumors near the esophagus that interfere with ability to swallow). The appropriate radioactive therapy regimen for the type of cancer, location of a tumor, and for the particular subject (i.e., dependent on age, general health status, etc.) is readily determined by a person skilled in the art. See Lawrence et al., editors. *Cancer: Principles and Practice of Oncology.* 8$^{th}$ ed. Philadelphia: Lippincott Williams and Wilkins, 2008.

As described herein, a medical therapy that is capable of inducing a biologically damaging response includes a chemotherapy (which includes a combination chemotherapy), and which may be referred to as a chemotherapy, chemotherapeutic, or chemotherapeutic drug. Many chemotherapeutics are compounds referred to as small organic molecules. Chemotherapies are widely used for treatment of cancers. As understood by a person skilled in the art, a chemotherapy may also refer to a combination of two or more chemotherapeutic molecules that are administered coordinately and which may be referred to as combination chemotherapy. Numerous chemotherapeutic drugs are used in the oncology art and include, without limitation, alkylating agents; antimetabolites; anthracyclines, plant alkaloids; and topoisomerase inhibitors. Alkylating agents include by way of example, cisplatin, carboplatin, oxalaplatin, cyclophosphamide, mechlorethamine, chlorambucil, ifosfamide. Exemplary antimetabolites include nucleosides antagonists, such as purines (for example, azathioprine, mercaptopurine) and pyrimidines. Other examples of nucleoside antagonists include 5-fluorouracil, 6-mercaptopurine, arabinosylcytosine, capecitabine, clofarabine, cytarabine, dacarbazine, fludarabine, gemcitabine and nelarabine. Vinca alkaloids, include for example, vincristine, vinblastine, vinorelbine, vindesine; taxane and its analogs and derivatives; and podophyllotoxin. Exemplary topoisomerase inhibitors are type I topoisomerase inhibitors such as the camptothecins, for example, irinotecan and topotecan. Other topoisomerase inhibitors are type II topoisomerase inhibitors, for example, amascrine, etoposide, etoposide phosphate, and teniposide, which are semisynthetic derivatives of eipoodophyllotoxins. Cytotoxic antibiotics that are chemotherapeutic agents include without limitation doxorubicin, daunorubicin, valrubicin, idarubicin, epirubicin, bleomycin, plicamycin, and mitomycin. Combination chemotherapies are often referred to by an acronym with which a person skilled in the art will be familiar and may comprise two or more of the chemotherapeutic drugs described above and in the art (e.g., CHOP, ABVD, BEACOPP, CAV, COPP, EPOCH, MACOP-B, MOPP, R-CHOP, and Stanford V regimens).

Certain chemotherapies are also used for treating other conditions, such as immunological diseases including autoimmune diseases (for example, ankylosing spondylitis, multiple sclerosis, Crohn's disease, psoriasis, psoriatic arthritis, rheumatoid arthritis, and scleroderma).

Other medical therapies that are biologically damaging include antiviral therapies, for example, high active antiretroviral therapies (HAART) used for treatment of HIV/AIDS. A HAART regimen may combine three or more different drugs, such as two nucleoside reverse transcriptase inhibitors (NRTIs) and a protease inhibitor (PI); two NRTIs and a non-nucleoside reverse transcriptase inhibitor (NNRTI); or other combinations.

Other medical therapies that may induce a biologically damaging response also include hormone therapies, which are generally not genotoxic therapies. By way of example, an angiotensin, Angiotensin II (Ang II) has been reported to promotes vascular inflammation by inducing premature senescence of vascular smooth muscle cells both in vitro and in vivo (see, e.g., Kunieda et al., *Circulation* 114:953-60 (2006)). Angiotensin is a peptide hormone that causes vasoconstriction and a subsequent increase in blood pressure. Clinical studies have been performed to determine if administering angiotensin to patient with sarcoma would have an anti-tumor effect by constricting blood vessels to the tumor. Insulin has also been described as a hormone that induces cellular senescence.

Medical therapies also include high dose chemotherapies or high dose radiation therapy that is administered to a subject who has a disease, such as cancer, and who is to receive a stem cell transplant (either autologous or allogeneic). By way of example, stem cell replacement therapy has been used for treating aplastic anemia, Hodgkin disease, non-Hodgkin lymphoma, testicular cancer, and leukemias (including acute myelogenous leukemia (AML), acute lymphoblastoic leukemia (ALL), chronic lymphocytic leukemia (CLL), chronic myelogenous leukemia (CML), therapy-related myelodysplasia (t-MDS) and therapy-related acute myeloid leukemia (t-AML)), and myelodysplastic syndrome.

The term "medical therapy" will be understood to include other terms commonly used in the art, such as medical treatment, therapeutic(s), and the like. Medical therapy includes a single active ingredient or component, one or more active ingredients or components, or multiple active ingredients or components that are administered to a subject in need to treat or to prevent (i.e., reduce the likelihood of occurrence or recurrence of) a disease or disorder. As described herein, medical therapies that are chemotherapies, such as cancer therapies, may include a single chemotherapeutic agent or may include combinations of two or more chemotherapeutic drugs (also called combination chemotherapy). By way of an additional example, as described herein, HAART is typically a combination or cocktail of three different viral agents.

Assessing Effectiveness of Medical Therapy

As described herein, by suppressing the biological damage response that is inducible by the medical therapy, the suppressive agents administered to a subject in need thereof provide enhancement (i.e., improvement) of the effectiveness (i.e., efficacy) of the medical therapy. Enhancing the effectiveness of a medical therapy results in an improvement or increase of the therapeutic and/or prophylactic benefit compared with the benefit observed in the absence of administering the agent. Accordingly, enhancing the effectiveness of the medical therapy may comprise attenuating (i.e., reducing, decreasing, preventing, inhibiting, suppressing) the deleterious biological and physiological effects of the medical therapy. By increasing the effectiveness of a medical therapy, the lifetime exposure to the therapy may be decreased, and consequently, biological damage is decreased.

The effectiveness of a medical therapy administered to a subject (i.e., patient) who also receives an agent that suppresses a biological damage response can readily be determined by a person skilled in the medical and clinical arts. One or any combination of diagnostic methods, including physical examination, assessment and monitoring of clinical symptoms, and performance of analytical tests and methods described herein, may be used for monitoring the health status of the subject.

Therapeutic and/or prophylactic benefit for subjects to whom the agents are administered, includes, for example, an improved clinical outcome, wherein the object is to prevent or slow or retard (lessen) an undesired physiological change associated with the disease, or to prevent or slow or retard (lessen) the expansion or severity of such disease. As discussed herein, enhancing the effectiveness of a medical therapy may include beneficial or desired clinical results that comprise, but are not limited to, abatement, lessening, or alleviation of symptoms that result from or are associated with the disease to be treated; decreased occurrence of symptoms; improved quality of life; longer disease-free status (i.e., decreasing the likelihood or the propensity that a subject will present symptoms on the basis of which a diagnosis of a disease is made); diminishment of extent of disease; stabilized (i.e., not worsening) state of disease; delay or slowing of disease progression; amelioration or palliation of the disease state; and remission (whether partial or total), whether detectable or undetectable; and/or overall survival. Enhancing the effectiveness of the medical therapy may also mean prolonging survival when compared to expected survival if a subject were not receiving the agent that suppresses a biological damage response.

In certain embodiments, when the medical therapy is a cancer therapy, enhancing the effectiveness of the therapy by the agent results in an improvement or increase of the therapeutic and/or prophylactic benefit compared with the benefit observed in the absence of administering the agent. For example, enhancing a medical therapy that is a cancer therapy includes any one or more of reducing the size of the tumor(s), inhibiting tumor progression, inhibiting tumor growth, delaying tumor colonization, and/or inhibiting, preventing, or delaying metastasis of a tumor. Enhancing the effectiveness of the therapy may include preventing, slowing, or decreasing development of resistance of the cancer (i.e., tumor or tumors) to the medical therapy, thereby allowing additional cycles of therapy and/or decreasing the time interval between cycles of therapy.

In addition to the benefits for patients with cancer discussed above, for subjects who have a cancer for which a medical therapy includes high dose chemotherapy and/or high dose radiation followed by autologous or allogenic stem cell replacement therapy, an improved clinical outcome in a subject who receives an agent that suppresses a biological damage response may be assessed by the time (i.e., number of days) for white blood cell recovery. For subjects who receive an allogenic stem cell transplant, improvement in graft versus tumor effect and absence or reduced graft versus host disease compared with subjects who do not receive the agent can indicate enhanced effectiveness of the high dose chemotherapy or high dose radiation.

When the medical therapy is an anti-viral therapy, and similarly as for radiation and chemotherapies for cancer, by suppressing the biological damage response, development of resistance to an anti-viral therapy may be reduced, the dose of the medical therapy may be reduced, or the time interval between administration of two doses may be increased, thereby reducing the lifetime exposure to the therapy. Improved clinical outcome is indicated, for example, by decreasing the time required for complete or partial eradication of the infection; prolonging disease-free status and/or overall survival; maintaining or improving immunological status; or reducing or lessening severity of one or more symptoms of the viral invention. For a person who is infected with HIV, in addition to the above improved clinical outcomes, a more effective anti-viral therapy including HAART may provide stability (i.e., decreasing the rate of decline) or improvement in T cell count; delay or reduce likelihood of occurrence of diseases associated with severe immunosuppression, such as Kaposi's sarcoma, AIDS related lymphoma, and opportunistic infections (e.g., candidiasis, cryptococcal meningitis, toxoplasmosis; coccidiomycosis; progressive multifocal leukoencephalopathy; HIV-related encephalopathy; shingles; crytosporidiosis; infections caused by CMV, *Mycobacterium* including tuberculosis, Herpes simplex virus, human papilloma virus, hepatitis virus B, hepatitis C).

Clinical benefit and improvement or a subject who has diabetes and receives insulin as the medical therapy and who receives an agent that suppresses a biological damage response, may be evaluated by stability of glucose levels. For example, an increase in the length of time between doses of insulin or a decrease in the dose of insulin required to maintain proper glucose levels in patients who receive an agent that suppresses a biological response indicates improved effectiveness of the insulin.

Pharmaceutical Compositions

Also provided herein are pharmaceutical compositions comprising any one or more of the agents that suppress a biological damage response. A pharmaceutical composition may be a sterile aqueous or non-aqueous solution, suspension or emulsion, which additionally comprises a physiologically acceptable excipient (pharmaceutically acceptable or suitable excipient or carrier) (i.e., a non-toxic material that does not interfere with the activity of the active ingredient). The excipients described herein are merely exemplary and are in no way limiting. An effective amount or therapeutically effective amount refers to an amount of an agent or a composition comprising one or more agents administered to a subject, either as a single dose or as part of a series of doses, which is effective to produce a desired therapeutic effect.

Subjects may generally be monitored for therapeutic effectiveness using assays suitable for the condition being treated or prevented, which assays will be familiar to those having ordinary skill in the art and are described herein. The level of an agent that is administered to a subject may be monitored by determining the level of the agent in a biological fluid, for example, in the blood, blood fraction (e.g., serum), and/or in the urine, and/or other biological sample from the subject. Any method practiced in the art to detect the agent may be used to measure the level of agent during the course of a therapeutic regimen.

The dose of an agent described herein for enhancing the effectiveness of a medical therapy may depend upon the subject's condition, that is, stage of the disease, severity of symptoms caused by the disease, general health status, as well as age, gender, and weight, and other factors apparent to a person skilled in the medical art. Pharmaceutical compositions may be administered in a manner appropriate to the disease to be treated as determined by persons skilled in the medical arts. An appropriate dose and a suitable duration and frequency of administration will be determined by such factors as the condition of the patient, the type and severity of the patient's disease, the particular form of the active ingredient, and the method of administration. Optimal doses of an agent may generally be determined using experimental models and/or clinical trials. The optimal dose may depend upon the body mass, weight, or blood volume of the subject. The use of the minimum dose that is sufficient to provide effective therapy is usually preferred. Design and execution of pre-clinical and clinical studies for an agent (including when administered for prophylactic benefit) described herein are well within the skill of a person skilled in the relevant art. The optimal dose of an agent may depend upon the body mass, weight, or blood volume of the subject. For example, an amount between 0.01 mg/kg and 1000 mg/kg (e.g., about 0.1 to 1 mg/kg, about 1 to 10 mg/kg, about 10-50 mg/kg, about 50-100 mg/kg, about 100-500 mg/kg, or about 500-1000 mg/kg) body weight.

The pharmaceutical compositions may be administered to a subject in need by any one of several routes that effectively deliver an effective amount of the agent. Such administrative routes include, for example, oral, topical, parenteral, enteral, rectal, intranasal, buccal, sublingual, intramuscular, transdermal, vaginal, rectal, or by intracranial injection, or any combination thereof. Such compositions may be in the form of a solid, liquid, or gas (aerosol).

Pharmaceutical acceptable excipients are well known in the pharmaceutical art and described, for example, in Rowe et al., Handbook of Pharmaceutical Excipients: A Comprehensive Guide to Uses, Properties, and Safety, $5^{th}$ Ed., 2006, and in *Remington: The Science and Practice of Pharmacy* (Gennaro, $21^{st}$ Ed. Mack Pub. Co., Easton, Pa. (2005)). Exemplary pharmaceutically acceptable excipients include sterile saline and phosphate buffered saline at physiological pH. Preservatives, stabilizers, dyes, buffers, and the like may be provided in the pharmaceutical composition. In addition, antioxidants and suspending agents may also be used. In general, the type of excipient is selected based on the mode of administration, as well as the chemical composition of the active ingredient(s). Alternatively, compositions described herein may be formulated as a lyophilizate, or the agent may be encapsulated within liposomes using technology known in the art. Pharmaceutical compositions may be formulated for any appropriate manner of administration described herein and in the art.

A pharmaceutical composition (e.g., for oral administration or delivery by injection) may be in the form of a liquid. A liquid pharmaceutical composition may include, for example, one or more of the following: a sterile diluent such as water for injection, saline solution, preferably physiological saline, Ringer's solution, isotonic sodium chloride, fixed oils that may serve as the solvent or suspending medium, polyethylene glycols, glycerin, propylene glycol or other solvents; antibacterial agents; antioxidants; chelating agents; buffers and agents for the adjustment of tonicity such as sodium chloride or dextrose. A parenteral preparation can be enclosed in ampoules, disposable syringes or multiple dose vials made of glass or plastic. The use of physiological saline is preferred, and an injectable pharmaceutical composition is preferably sterile.

For oral formulations, at least one of the agents described herein can be used alone or in combination with appropriate additives to make tablets, powders, granules or capsules, and if desired, with diluents, buffering agents, moistening agents, preservatives, coloring agents, and flavoring agents. The agents may be formulated with a buffering agent to provide for protection of the agent from low pH of the gastric environment and/or an enteric coating. An agent included in the compositions may be formulated for oral delivery with a flavoring agent, e.g., in a liquid, solid or semi-solid formulation and/or with an enteric coating.

A composition comprising any one of the agents described herein may be formulated for sustained or slow release. Such compositions may generally be prepared using well known technology and administered by, for example, oral, rectal or subcutaneous implantation, or by implantation at the desired target site. Sustained-release formulations may contain the agent dispersed in a carrier matrix and/or contained within a reservoir surrounded by a rate controlling membrane. Excipients for use within such formulations are biocompatible, and may also be biodegradable; preferably the formulation provides a relatively constant level of active component release. The amount of active agent contained within a sustained release formulation depends upon the site of implantation, the rate and expected duration of release, and the nature of the condition to be treated or prevented.

Kits with unit doses of one or more of the agents described herein, usually in oral or injectable doses, are provided. Such kits may include a container containing the unit dose, an informational package insert describing the use and attendant benefits of the drugs in treating pathological condition of interest, and optionally an appliance or device for delivery of the composition.

EXAMPLES

Example 1

Preparation of p16-3MR Transgenic Mice

To examine the role of senescent cells in cancer, in the risk of developing cancer or in side effects arising after cancer treatment, a transgenic mouse comprising a $p16^{Ink4a}$ promoter operatively linked to a trimodal fusion protein was generated to allow for detection of senescent cells and for selective clearance of senescent cells in those transgenic mice.

Figure 5A:
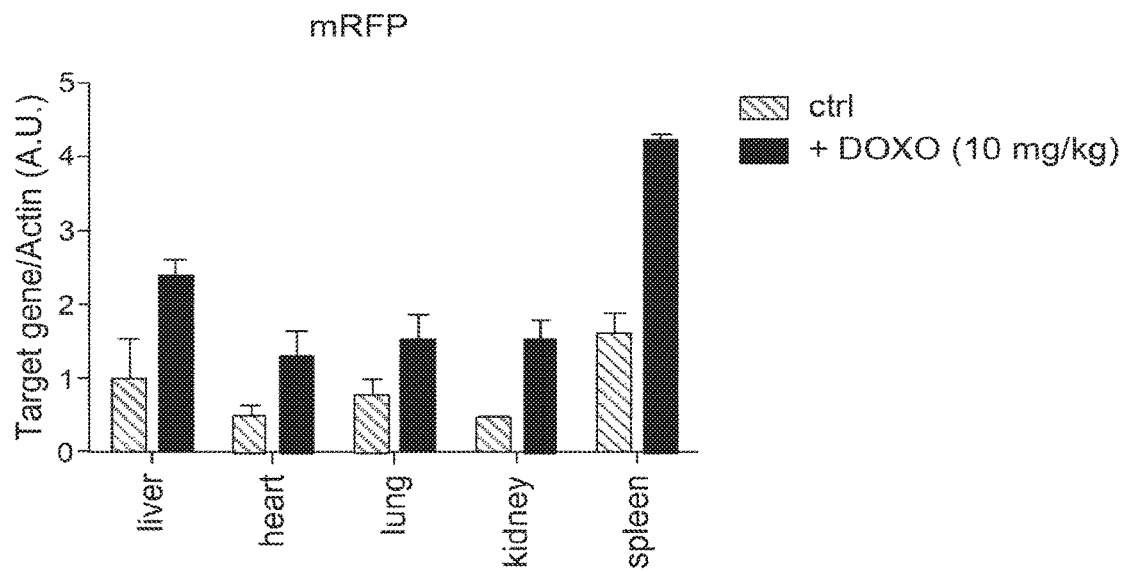
FIGS. 5A-5B show that treatment with doxorubicin induces persistent senescent cells in p16-3MR transgenic mice. The transgenic p16-3MR mice were mock treated with vehicle (Ctrl) or treated with 10 mg/kg of doxorubicin (DOXO). Various tissues were isolated (liver, heart, lung, kidney, and spleen) and measured for abundance of mRNAs encoding mRFP (FIG. 5A) and p16INK4a (FIG. 5B) (normalized to actin).
Figure 5B:
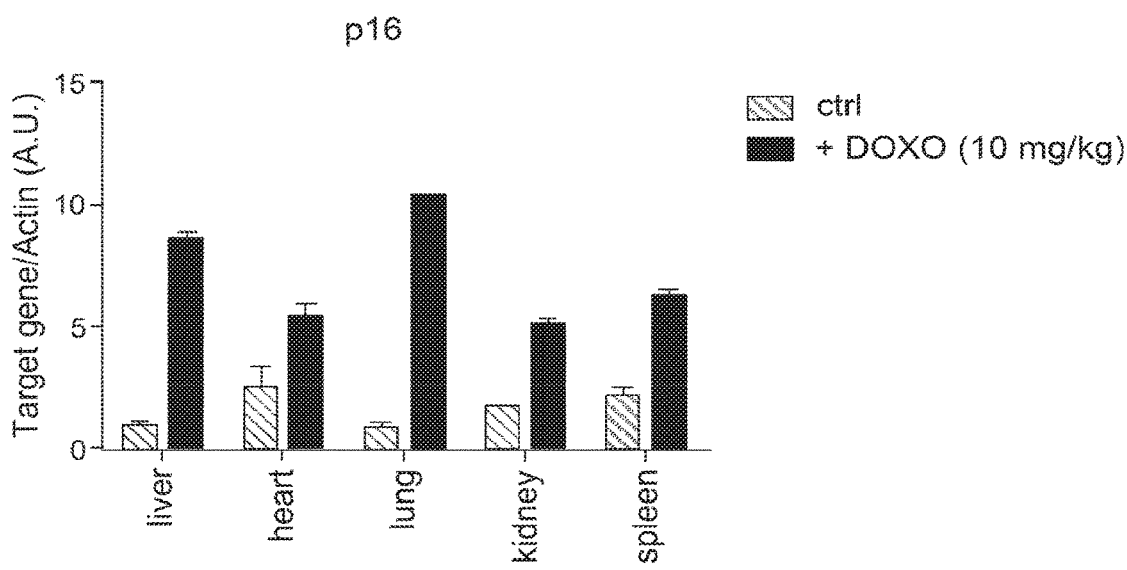

The promoter, $p16^{Ink4a}$, which is transcriptionally active in senescent cells but not in non-senescent cells (see, e.g., Wang et al., *J. Biol. Chem.* 276:48655-61 (2001); Baker et al., *Nature*, supra) was engineered into a nucleic acid construct. A fragment of the $p16^{Ink4a}$ gene promoter (see FIGS. 5 and 6 providing an exemplary vector and exemplary promoter sequence) was introduced upstream of a nucleotide sequence encoding a trimodal reporter fusion protein. The trimodal reporter protein is termed 3MR and consists of *renilla* luciferase (rLUC), monomeric red fluorescent protein (mRFP) and a truncated herpes simplex virus thymidine kinase (tTK) (see, e.g., Ray et al., *Cancer Res.* 64:1323-30 (2004)). Thus, the expression of 3MR is driven by the $p16^{Ink4a}$ promoter in senescent cells only. The polypeptide sequences and the encoding polynucleotides for each of the three proteins are known in the art and are available in public databases, such as GenBank. The detectable markers, rLUC and mRFP permitted detection of senescent cells by bioluminescence and fluorescence, respectively. The expression of tTK permitted selective killing of senescent cells by exposure to the pro-drug ganciclovir (GCV), which is converted to a cytotoxic moiety by tTK. Transgenic founder animals, which have a C57B16 background, were established and bred using known procedures for introducing transgenes into animals (see, e.g., Baker et al., *Nature*, supra). The transgenic mice are called p16-3MR herein.

Example 2

Senescent Cells can be Detected and Cleared in Transgenic p16-3MR Mice

Senescent cells can be detected using a variety of biomarkers, including the strongly upregulated p16-INK4a tumor suppressor protein (Campisi et al., *Nature Rev. Molec. Cell Biol.* 8:729-40 (2007)). Using such markers, it was shown that both normal and tumor cells undergo senescence, in mice and humans, after exposure to ionizing radiation or DNA-damaging chemotherapy (Coppe et al., *PLoS Biol.* 6:2853-68 (2008); Schmitt et al., *Cell* 109:335-46 (2002); to Poele et al., *Canc. Res.* 62:1876-83 (2002); Le et al., *Aging Cell* 9:398-409 (2010)). For example, p16-3MR transgenic mice will accumulate senescent cells when exposed to genotoxins (e.g., ionizing radiation, DNA damaging chemicals), epigenomic toxins (e.g., compounds that perturb histone modifications or DNA methylation), strong mitogenic signals (e.g., activated oncogenes, elevated levels of growth factors, certain hormones). But, as noted herein, one advantage of the p16-3MR transgenic mice is that they express tTK, which allows for selective killing of senescent cells by administering pro-drug ganciclovir (GCV) to the mice since GCV is converted into a cytotoxin by tTK. Therefore, the clearance of senescent cells in p16-3MR transgenic mice exposed to radiation was examined after GCV treatment.

Briefly, a group of p16-3MR transgenic mice were exposed to whole body ionizing radiation (7 Gy X-ray) and a control group of p16-3MR transgenic mice were mock-irradiated. After three months, the mice were treated with GCV (25 mg/kg) or vehicle only, and then at least two weeks later bioluminescence in tissues was examined after administering the rLUC substrate.

Figure 1A:
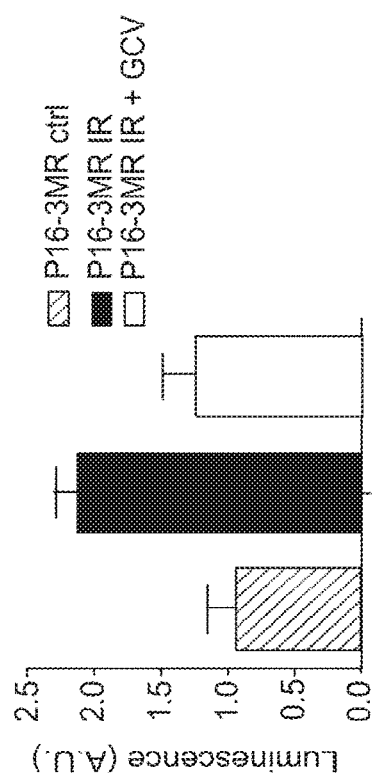

In several tissues, irradiated mice (IR) showed a greater than 2-fold higher bioluminescence than unirradiated mice (Ctrl), indicating that rLUC is expressed three months after radiation exposure and, therefore, the presence of senescent cells is persisting (see FIG. 1A, showing bioluminescence results in lung tissue). Moreover, mice treated with GCV exhibited rLUC expression levels comparable to unirradiated mice, indicating that GCV resulted in elimination of senescent cells (FIG. 1A).

As is known in the literature, senescent cells also secret molecules that can cause inflammation (Freund et al., *Trends Mol. Med.* 16:238-46 (2010)), which, if chronic, will fuel various pathologies, including cancer (Davalos et al., *Cancer Metastasis Rev.* 29:273-83 (2010))—this is often referred to as senescence-associated secretory phenotype (SASP). For example, IL-6 (interleukin-6) and MMP-3

(matrix metalloproteinase-3) are two prominent SASP components. Hence, RNA expression levels of various biomarkers associated with SASP were examined, including p16INK4a (p16), IL-6 and MMP-3. In addition, the level of the mRFP reporter was measured. FIG. 1B shows that GCV returned p16INK4a (p16), IL-6, MMP-3 and mRFP expression levels to those found in the unirradiated control mice. Furthermore, GCV notably had no detectable effect on expression levels when given to wild-type, non-transgenic C57B16 mice (data not shown).

Example 3

Cellular Senescence Increases the Likelihood of Cancer and Metastasis

To examine the role of senescence in contributing to, inducing or increasing the likelihood of tumor formation or growth and metastasis, tumor engraftment was monitored in p16-3MR transgenic mice that were either depleted of senescent cells and in mice that had senescent cells (naturally developed or induced).

Briefly, $10^6$ B16 mouse melanoma cells, a highly aggressive cell line that is syngeneic with p16-3MR transgenic mice (C57B16 background), that express firefly luciferase (fLUC, to enable their detection by bioluminescence) were injected into the tail vein of the p16-3MR transgenic mice approximately three months after being either mock irradiated or irradiated, as described in Example 2. Irradiated mice were treated daily with GCV (25 mg/kg) or vehicle only for 7 days, and then 3 days following the last GCV dose, B16 mouse melanoma cells were injected into the mice. B16 mouse melanoma cells first colonize the lung, where they form primary tumors approximately two weeks after injection, and thereafter metastasize to distal tissues to form secondary tumors in, for example, the pancreas, liver and visceral fat. The bioluminescence markers, fLUC and rLUC are distinguishable because the enzymes use different substrates.

Figures 2A, 2B, 2C:
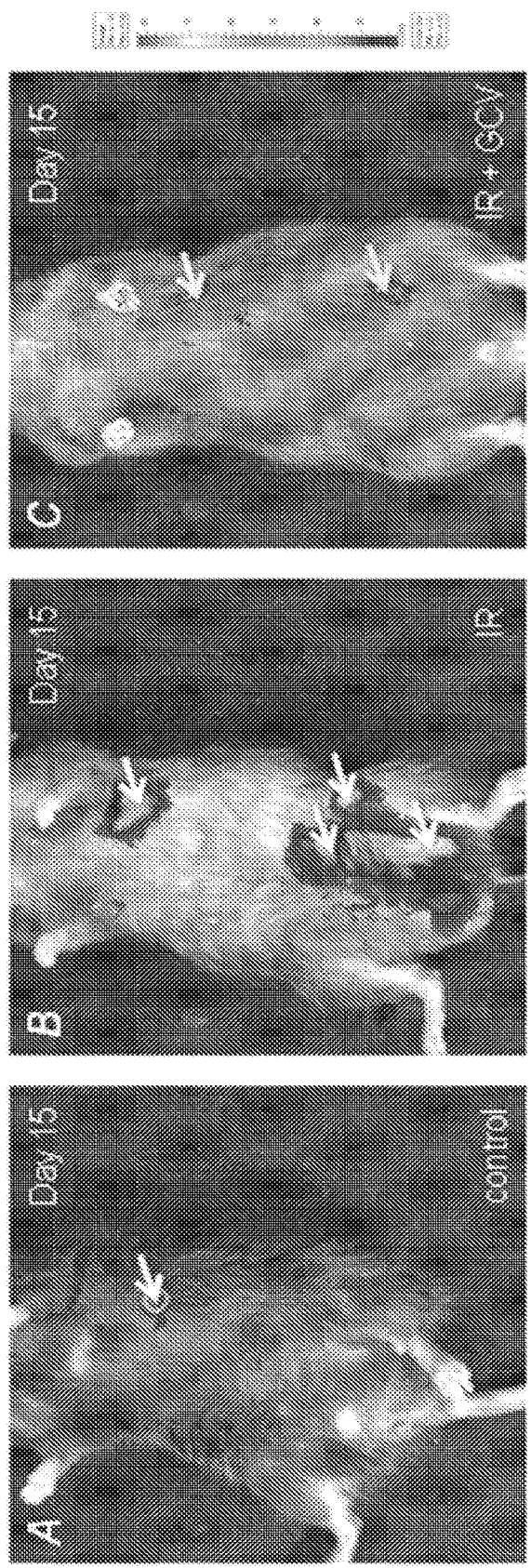
FIGS. 2A-2C show senescent cells induced in p16-3MR transgenic mice by irradiation promote primary and metastatic tumor growth. The transgenic p16-3MR mice were mock-irradiated (Ctrl) or irradiated (IR). Three months later, the irradiated mice were treated with vehicle (IR) or GCV (IR+GCV), then injected with fLUC-expressing B16 melanoma cells into the tail veins. Fifteen days later, bioluminescence of the B16 melanoma cells was measured.
Figure 3:
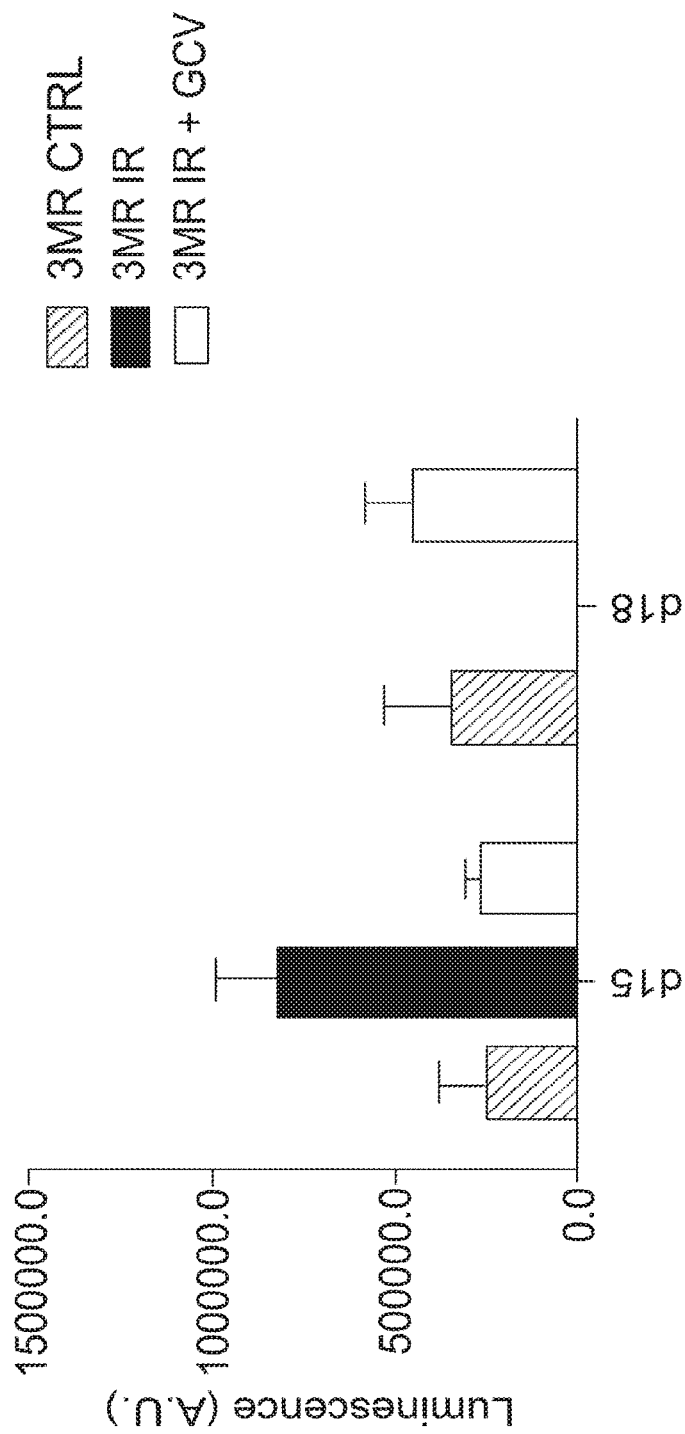
FIG. 3 shows full body luminescence measurements of the B16 melanoma cells from the mice in FIGS. 2A-2C. Irradiated mice were moribund at day 15-16 and were sacrificed.

As shown in FIG. 2, tumor progression occurred much faster in the irradiated mice as compared to the mock-irradiated mice. Fifteen days after the injection, mock-irradiated (Ctrl) mice had some relatively small lung nodules (see FIG. 2A). In contrast, irradiated mice had significantly more primary tumors and, additionally, the animals harbored a large number of metastatic tumors (see FIG. 2B) these animals were moribund between days 15 and 16 after injection. Strikingly, irradiated mice in which senescent cells were cleared after GCV treatment showed much smaller primary tumors and many fewer metastases (see FIG. 2C). B16 mouse melanoma cells were detected in the mice ~15-18 days post-injection by measuring fLUC bioluminescence. Irradiated mice were moribund at days 15-16 post-injection and sacrificed. Fifteen days after the injection, mock-irradiated (Ctrl) mice and irradiated mice in which senescent cells were cleared after GCV treatment both had relatively low levels of B16 cells as detected by luminescence (see FIG. 3). Irradiated mice had significantly larger numbers of B16 cells as detected by luminescence (see FIG. 3). On day 18, irradiated mice in which senescent cells were cleared after GCV treatment still showed relatively low levels of B16 cells as did the mock-irradiated control (Ctrl) mice (see FIG. 3).

Figures 4A, 4B, 4C:
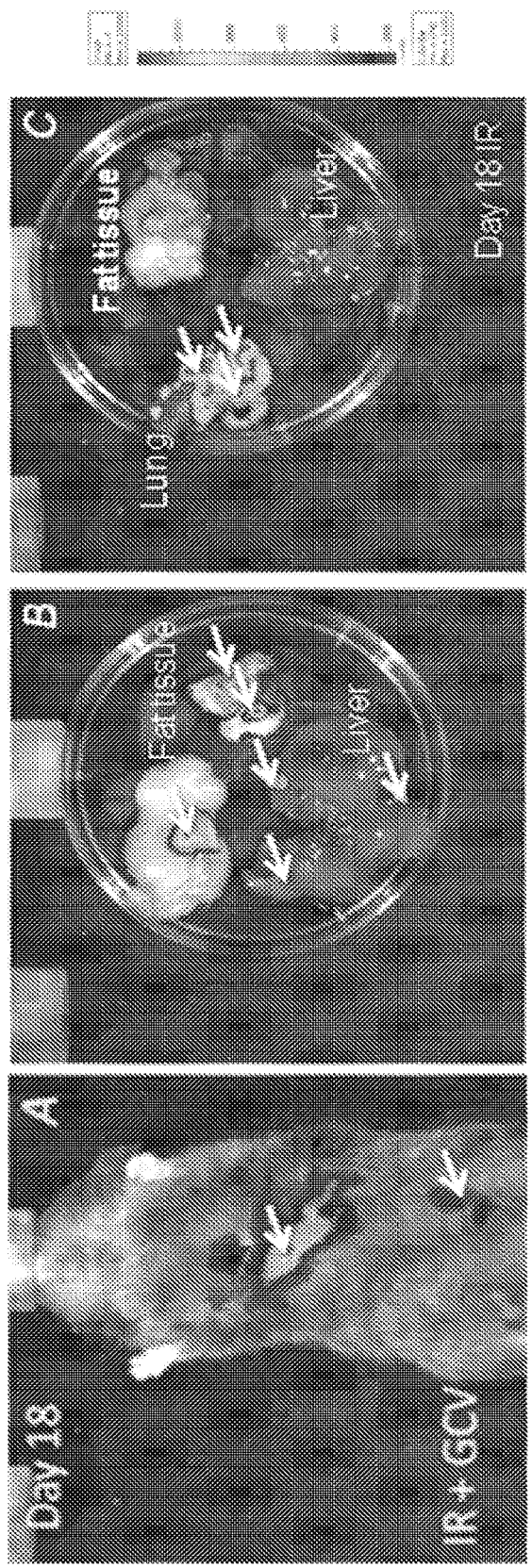
FIGS. 4A-4C show that elimination of senescent cells suppresses the development of metastases. The p16-3MR transgenic mice of FIG. 2 were followed for an additional three days (i.e., day 18). The irradiated mice treated with GCV (in which senescent cells were eliminated) eventually developed primary tumors in the lungs (FIG. 4A). But, despite the presence of primary tumors in the lung, the fat and liver tissues remained relatively metastasis free (FIG. 4C). In contrast, irradiated mice not treated with GCV (which retain senescent cells) showed metastatic tumors in the liver and fat tissue (FIG. 4B).

Eighteen days after injecting the B16 melanoma cells, large primary lung tumors were evident in the irradiated mice that received GCV treatment (see FIG. 4A). But, despite the presence of tumors in the lungs, the distal organs remained almost devoid of metastases (see FIG. 4A; see also FIG. 4C showing liver and fat tissue). This was in sharp contrast to irradiated mice not treated with GCV, in which the liver and fat harbored multiple metastatic tumors (see FIG. 4B), which were already present by day 15. Luminescent metastatic nodules were also counted in control, irradiated, and irradiated+GCV treated mice as provided in Table 2. As nodules are difficult to count in fat tissue, metastatic cells were represented as an estimated % of total area of fat.

TABLE 2

Detection of metastatic B16 melanoma cells 18 days after injection

| | Control mice | Irradiated mice | Irradiated + GCV |
|---|---|---|---|
| Lung | Too numerous to count (TNTC) | TNTC | TNTC |
| Liver | 6.25 ± 1.7 nodules | 14.5 ± 2.8 nodules | 7 ± 3.6 nodules |
| Fat | 50% | 100% | 25% |

Similar results were observed when the senescent cell accumulation was induced with the chemotherapeutic agent, doxorubicin. Using p16-3MR mice, treatment doxorubicin (10 mg/kg) induced the persistent presence of senescent cells in tissues, similar to the effects of radiation. Various tissues were isolated (liver, heart, lung, kidney, and spleen) and measured for abundance of mRNAs encoding mRFP and p16INK4a as markers for senescent cells (see FIGS. 5A and 5B, respectively). Doxorubicin-treated mice consistently expressed higher levels of mRFP and p16INK4a in all tissues compared to untreated control mice.

Also similar to the effects of radiation, doxorubicin treatment stimulated the growth of B16 melanoma cells that were injected subcutaneously. Again, similar to radiation-treated mice, GCV (which eliminates senescent cells in p16-3MR mice) substantially reduced the size of B16 melanoma tumors in mice pre-treated with doxorubicin. Briefly, p16-3MR transgenic mice were treated with vehicle (ctrl) or 10 mg/kg doxorubicin. Seven days after doxorubicin treatment, mice were treated daily with GCV (25 mg/kg) for 7 days or vehicle only. 3 days after the last GCV treatment, $4 \times 10^5$ B16 mouse melanoma cells were injected subcutaneously into the p16-3MR transgenic mice, and mice were sacrificed after 12 days for analysis.

Figure 6:
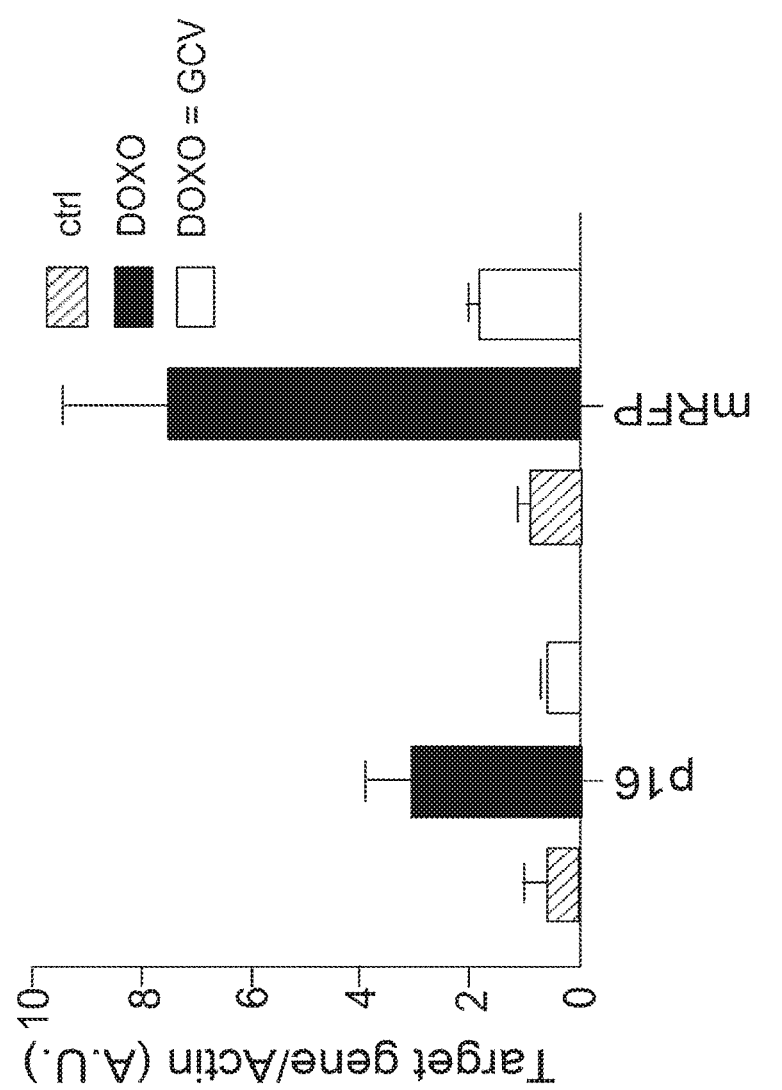
FIG. 6 shows that doxorubicin induces persistent senescent cells in p16-3MR transgenic mice and that GCV treatment leads to depletion of senescent cells and reducing the level of SASP biomarkers, p16INK4 and mRFP. Skin biopsies were isolated and measured for abundance of p16INK4 and mRFP (normalized to actin). Results are shown in arbitrary units (AU) after setting Ctrl levels at 1.

Skin biopsies were collected and measured for abundance of senescent cell biomarkers (p16INK4a and mRFP mRNAs). As shown in FIG. 6, skin biopsies from doxorubicin treated mice showed increased senescence as compared to skin biopsies from untreated control mice, as measured by p16INK4a and mRFP expression. In contrast, doxorubicin-treated mice in which senescent cells were cleared by GCV treatment showed low levels of p16INK4a and mRFP expression.

Figure 7:
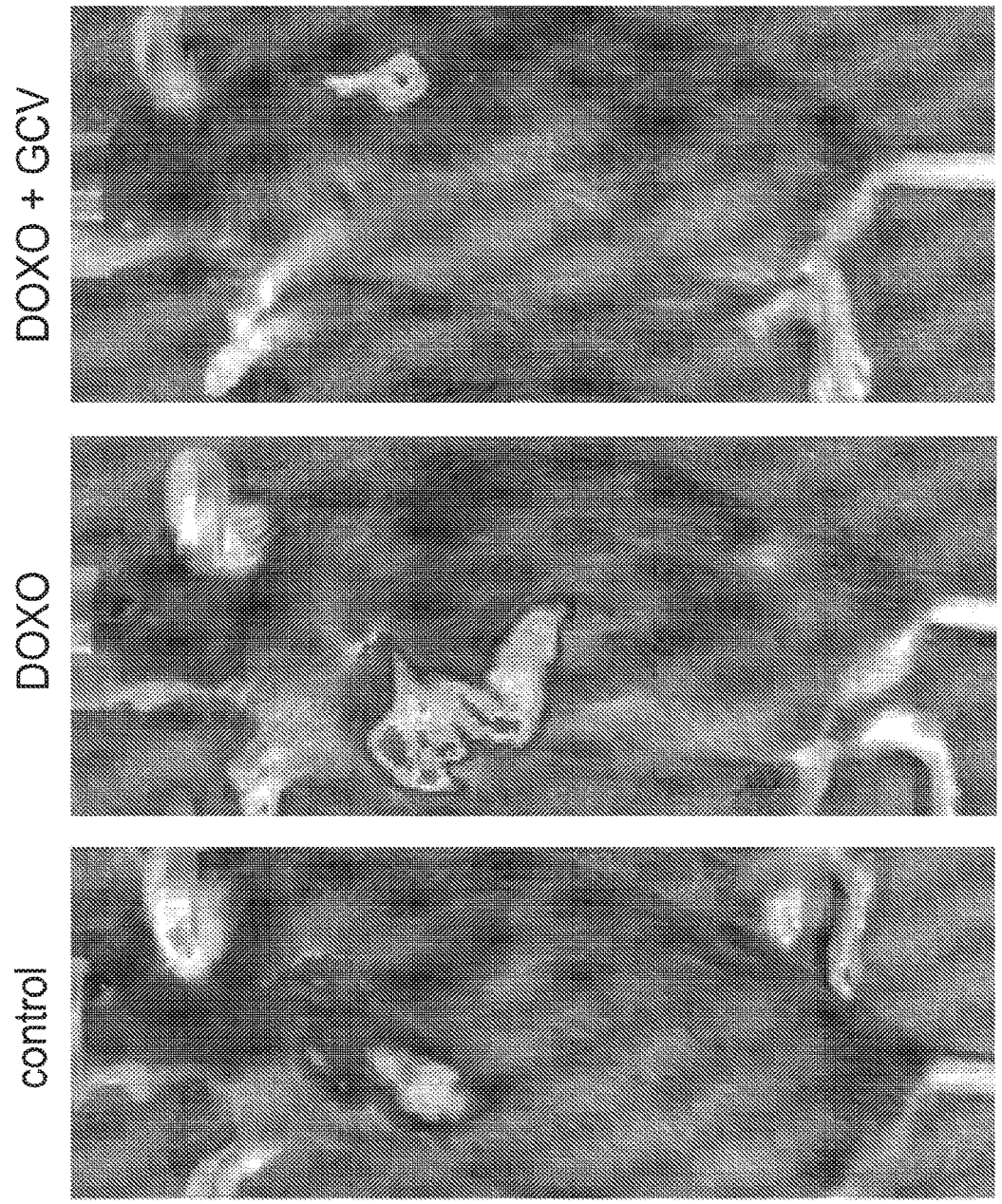
FIG. 7 shows senescent cells induced in p16-3MR transgenic mice by doxorubicin treatment promoted primary tumor growth. The transgenic p16-3MR mice were vehicle-treated (Ctrl) or treated with doxorubicin (10 mg/kg). 7 days later, the doxorubicin treated mice were mock treated with vehicle (DOXO) or GCV (DOXO+GCV), then injected subcutaneously with fLUC-expressing B16 melanoma cells. Twelve days later, bioluminescence of the B16 melanoma cells was measured.
Figure 8:
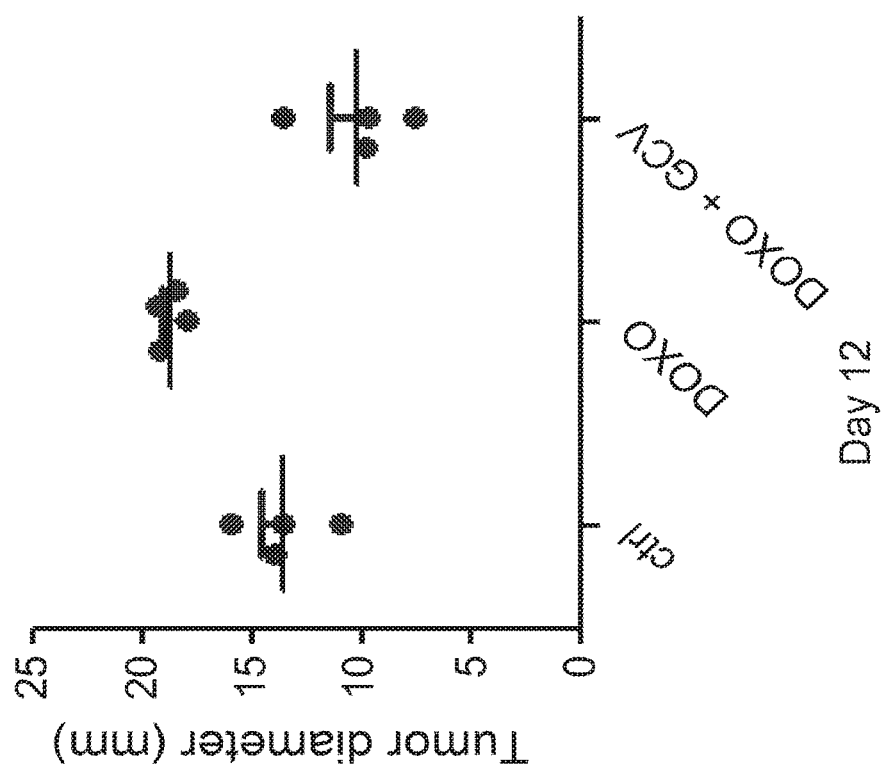
FIG. 8 shows that clearance of senescent cells in doxorubicin treated p16-3MR transgenic mice reduced tumor size. The transgenic p16-3MR mice were vehicle-treated (Ctrl) or treated with doxorubicin (10 mg/kg). 7 days later, the doxorubicin treated mice were mock treated with vehicle (DOXO) or GCV (DOXO+GCV), then injected subcutaneously with fLUC-expressing B16 melanoma cells. Twelve days later, primary tumor diameter was measured.

Tumor growth was increased in doxorubicin-treated mice as compared to vehicle-treated control mice (see FIG. 7). In contrast, doxorubicin-treated mice in which senescent cells were cleared after GCV treatment showed much smaller primary tumors (see FIG. 7). Tumor diameters were also measured and also confirmed that doxorubicin-treated mice in which senescent cells were eliminated by GCV treatment had smaller tumor sizes, and doxorubicin-treated mice had increased tumor sizes (see FIG. 8).

Overall, an increase in senescent cell population induced by radiation or doxorubicin correlated with a greatly increased primary tumor size and with metastases (radiation only), but this was largely abrogated when senescent cells were depleted in mice treated with GCV. In other words, these results show that the persistent presence of senescent cells after exposure to a senescence causing stress can promote the growth of primary tumors and will advance the development of metastases. Thus, senescence cell clearance or depletion can delay, prevent, or reduce the risk or likelihood of tumor formation or metastasis.

Example 4

Senescent Cell Clearance Reduces Likelihood of K-Ras Mediated Tumorigenesis

To examine the role of senescence in contributing to, inducing or increasing the likelihood of K-Ras mediated lung tumor formation or growth and metastasis, tumor formation was monitored in INK-ATTAC transgenic mice that were either depleted of senescent cells or have senescent cells (naturally developed or induced).

Briefly, INK-ATTAC (p16$^{Ink4a}$ apoptosis through targeted activation of caspase) transgenic mice have an FK506-binding protein (FKBP)-caspase 8 (Casp8) fusion polypeptide under the control of the p16$^{Ink4a}$ promoter (see FIG. 10 providing a vector sequence for the transgene and FIG. 11 providing sequences for components of the transgene including the promoter sequence). In the presence of AP20187, a synthetic drug that induces dimerization of a membrane bound myristoylated FKBP-Casp8 fusion protein, senescent cells specifically expressing the FKBP-Casp8 fusion protein via the p16$^{Ink4a}$ promoter undergo programmed cell death (apoptosis) (see, e.g., Baker, Nature, supra, FIG. 1 therein). Two founder lines (INK-ATTAC$^3$ and INK-ATTAC$^5$) were each bred with the K-rasLA1 tumor model. K-rasLA1 mice were first developed by Tyler Jacks at M.I.T. (see Johnson, L. et al., Nature 410:1111-16 (2001). The mice activate a silent K-ras oncogene through a spontaneous recombination event. The mean age of death/sacrifice of K-rasLA1 mice is about 300 days as a result of extensive tumor burden. The most frequent organ site is the lung and varying grades of tumors are present as early as six weeks of age from hyperplasia/dysplasia to carcinomas similar to human non-small cell lung cancer. Metastasis to thoracic lymph nodes, kidney and other visceral organs occurs with low frequency. Other organ sites include the thymus (thymic lymphoma) and skin (papillomas). A companion strain (K-ras$^{LA2}$) carries an allele that recombines to the activated allele (K-Ras$^{G12D}$) 100% of the time.

Figure 9:
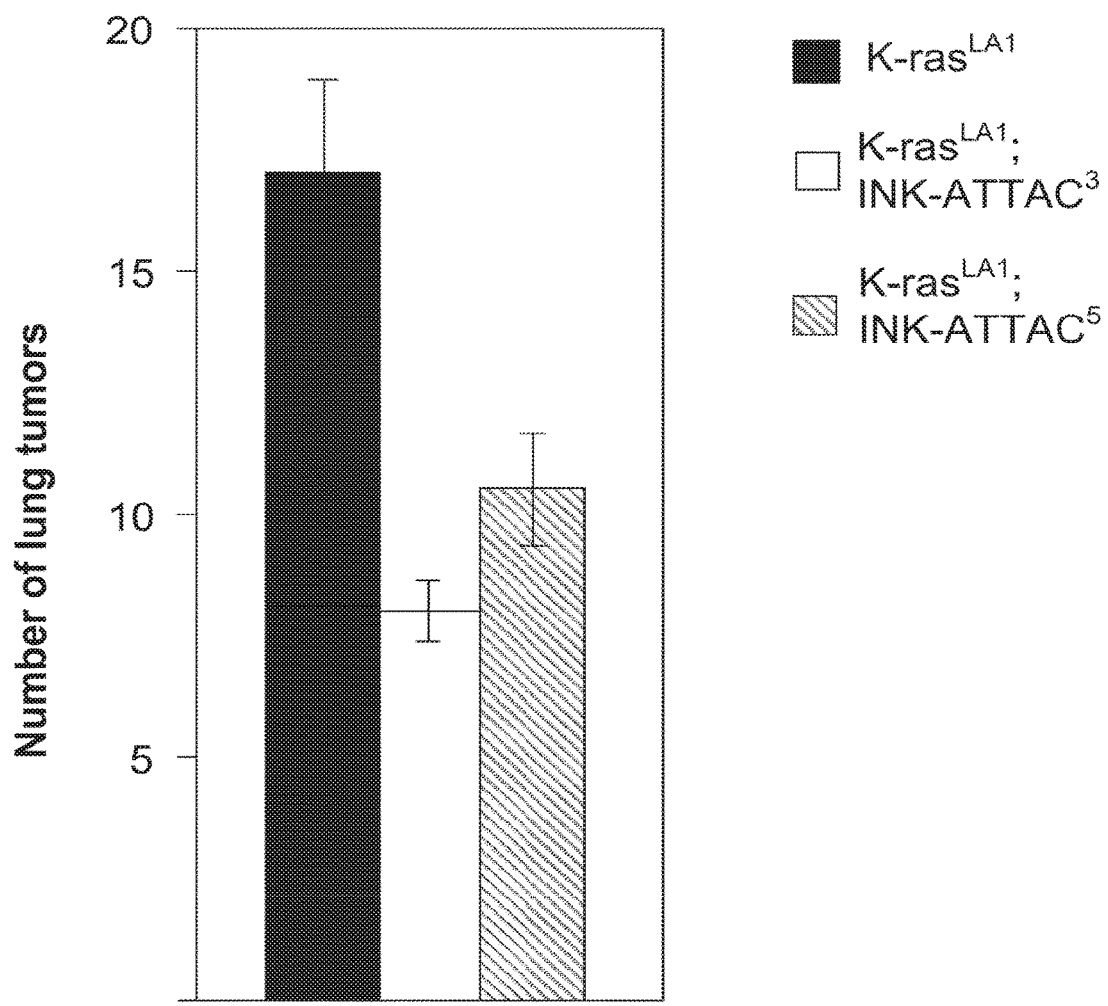
FIG. 9 shows that elimination of senescent cells suppresses the multiplicity of K-Ras induced lung tumors as compared to mice in which senescent cells were not cleared or reduced.

Two INK-ATTAC:K-RasLA1 were produced (one for INK-ATTAC line 3 and one for line 5). Beginning at three weeks of age, one half each cohort was treated with 2 mg AP20187/g body weight and the remaining half with vehicle (PBS). Twenty one days after treatment, the mice were sacrificed and tumor multiplicity in lungs was measured. Tumor numbers were found to be significantly reduced in INK-ATTAC3:K-RasLA1 and INK-ATTAC5:K-RasLA1 transgenic mice that had senescent cells depleted after treatment with AP20187 (see FIG. 9). In addition, metastasis and overall survival will be monitored after tumor induction in the presence or absence of p16-positive cells.

Example 5

Senescent Cell Clearance Reduces Likelihood of Breast Cancer or Skin Carcinogenesis Similar experiments to those of Example 4 can be performed using doxycycline-mediated expression of HER2 (see, e.g., Yeh et al., J. Clin. Investig. 121:866-79 (2011); see also Gunther et al., FASEB 16:283-92 (2002)) to examine the role of senescence in contributing to, inducing or increasing the likelihood of breast cancer. For example, founder INK-ATTAC lines are each bred onto a transgenic mouse MMTV-HER2 or a bi-transgenic mouse MMTV-rtT:TetO-HER2 genetic background, wherein doxycycline can be used to induce breast tumor formation subsequent to a senescence inducing factor (e.g., radiation or chemotherapy) used to induce senescent cell accumulation.

Alternatively, INK-ATTAC transgenic mice can be treated with a senescence inducing factor (e.g., radiation or chemotherapy) and then a carcinogen to examine the role of senescence in contributing to, inducing or increasing the likelihood of skin carcinogenesis (see, e.g., Slaga et al., J. Investig. Dermatol. Symp. Proc. 1:151-6 (1996)).

Example 6

Senescent Cell Reduction Reduces Likelihood of Side Effects from Senescence Inducing Chemotherapy To examine the role of senescence in contributing to, inducing or increasing the likelihood of side effects resulting from, for example, radiation or chemotherapy used to treat cancer that has already developed. Such side effects may include returning or recurring tumor formation or growth and metastasis. Side effects are monitored in p16-3MR transgenic mice that are either depleted of senescent cells or have senescent cells (naturally developed or induced).

Briefly, tumor cell lines are engineered to express firefly luciferase (fLUC) to enable their detection of tumors and metastases by bioluminescence in a living animal. In particular, a B16-fLUC mouse melanoma cell line and an MMTV-PymT:fLUC mammary carcinoma cell line are generated. The tumor cells are injected into the mice (i.e., B16 into a tail vein; and MMTV-PymT into a mammary fat pad) and small primary tumors are allowed to form over a period of one to four weeks. Then doxorubicin at 10 mg/kg or vehicle only is administered two to four times over a period of one week. Three days after the last doxorubicin administration, GCV is administered 5× daily intraperitoneally at 25 mg/kg or vehicle only is administered. Four different treatment groups of mice include (1) no doxorubicin (vehicle), no GCV (vehicle); (2) doxorubicin, no GCV; (3) no doxorubicin, GCV; and (4) doxorubicin, GCV. Bioluminescence in tissues is examined (after administering the rLUC substrate) to monitor tumor formation and mouse survival is also monitored. In addition, mice may be housed in metabolic cages for periods of 5-8 days to monitor food consumption, water consumption, body mass, spontaneous activity and behavior, voluntary exercise, oxygen consumption, and carbon dioxide production.

Example 7

Senescent Cell Reduction Reduces Likelihood of Side Effects from Senescence Inducing Radiotherapy To examine the role of senescence in contributing to, inducing or increasing the likelihood of side effects resulting from, for example, radiation or chemotherapy used to treat cancer that has already developed. Such side effects may include returning or recurring tumor formation or growth and metastasis. Side effects are monitored in p16-3MR transgenic mice that are either depleted of senescent cells or have senescent cells (naturally developed or induced).

Briefly, tumor cell lines are engineered to express firefly luciferase (fLUC) to enable their detection of tumors and metastases by bioluminescence in a living animal. In particular, a B16-fLUC mouse melanoma cell line and an MMTV-PymT:fLUC mammary carcinoma cell line are generated. The tumor cells are injected into the mice (i.e., B16 into a tail vein; and MMTV-PymT into a mammary fat pad) and small primary tumors are allowed to form over a period of one to four weeks. Then groups of animals are exposed to non-lethal ionizing radiation (IR) or sham-irradiated. Three days after the last irradiation exposure, GCV is administered 5× daily intraperitoneally at 25 mg/kg or vehicle only is administered. Four different treatment groups of mice include (1) no IR (sham irradiated), no GCV; (2) IR, no GCV; (3) no IR, GCV; and (4) IR, GCV. Bioluminescence in tissues is examined (after administering the rLUC substrate) to monitor tumor formation and mouse survival is also monitored. In addition, mice may be housed in metabolic cages for periods of 5-8 days to monitor food consumption, water consumption, body mass, spontaneous activity and behavior, voluntary exercise, oxygen consumption, and carbon dioxide production.

Example 8

Screening for and Characterization of Compounds that Selectively Suppress Components of the Senescence-Associated Secretory Phenotype (SASP)

To identify small molecules that potentially suppress the senescence-associated secretory (SASP) phenotype, a screening strategy using normal human fibroblasts that were either quiescent or senescent and a library of compounds that are approved for human use was developed as described in further detail below.
Experimental Procedures:
Cell Cultures and Regents HCA2 human neonatal foreskin, IMR-90 human fetal lung fibroblasts and T47D human breast cancer cells were obtained and cultured in 3% $O_2$ and 10% $CO_2$ as previously described (Coppe et al., 2008, PLoS Biol. 6:2853-2868; Rodier et al., 2009, Nature Cell Biol. 11:973-979; Coppe et al., 2010, PLoS ONE 5:e9188). Cells were induced to senesce by X-irradiation (10 Gy) or lentiviral expression of oncogenic RAS or MAP kinase kinase 6 (MKK6), as described (Coppe et al., 2008, PLoS Biol. 6:2853-2868; Rodier et al., 2009, Nature Cell Biol. 11:973-979; Freund et al., 2011, EMBO J. 30:1536-1548). Pre-senescent and senescent cells had 24-h BrdU labeling indices of >75% and <10% respectively (Rodier et al., 2009, Nature Cell Biol. 11:973-979); <10% and >70% respectively stained positive for senescence-associated beta-galactosidase activity (Dimri et al., 1995, Proc. Natl. Acad. Sci. USA 92:9363-9367) (Biovision senescence detection kit). HEK293FT packaging cells (Invitrogen) were used to generate lentiviruses. Corticosterone, cortisol and RU-486 were obtained from Sigma-Aldrich.
Viral Vectors and Infection Lentiviruses encoding oncogenic RAS and MKK6 were described (Coppe et al., 2008, PLoS Biol. 6:2853-2868; Freund et al., 2011, EMBO J. 30:1536-1548). Lentiviruses encoding shRNAs against GFP (control) and the GR were purchased from Open Biosystems. The lentiviral NF-κB reporter-luciferase construct was purchased from SA Biosciences. Lentiviruses were produced and used as described (Coppe et al., 2008, PLoS Biol. 6:2853-2868; Freund et al., 2011, EMBO J. 30:1536-1548). To limit side effects of infection, viral titers were adjusted to infect 90% of cells, and cultures were subsequently selected in 1 μg/ml puromycin for 3 days.
Initial Drug Screening The initial drug screen was performed in a 96-well format using automated liquid handling with a Biomek FX (Beckman Coulter, CA). Senescent cells were plated 24 hours after X-irradiation at 7,500 cells per well in 96-well plates. Six days after plating the senescent cells, the pre-senescent cells were plated at 7,500 cells per well in 96-well plates. Twenty-four hours after pre-senescent plating, both pre-senescent and senescent cells were washed and incubated in low (0.2%) serum for 48 hours to arrest cell proliferation of the pre-senescent cells. Drugs from the Prestwick Chemical Library, which contains 1120 bio-available compounds in DMSO, were given to the cells at 2.5 μM in media containing 0.2% serum. Forty-eight hours after compound addition, the medium in each well was removed and frozen for assay by ELISA to quantitate the levels of IL-6. The cells, which remained in the wells after the medium was removed, were lysed and ATP levels were measured (ATPlite 1-step assay, Perkin Elmer, MA) to exclude compounds that lowered IL-6 through toxicity (cell death). Experimental wells in each plate were normalized to plate mean or same-plate DMSO controls for the ELISA and ATP assays, respectively.
Subsequent Treatments with Glucocorticoids To validate glucocorticoids as SASP regulators, they were added within 15 min after irradiation (unless otherwise indicated). For cells induced to senesce by MKK6 or RAS overexpression, glucocorticoid treatment started 16 hours after infection. Glucocorticoids were re-added in fresh media every other day. Six days after irradiation or selection, cells were given serum-free DMEM with or without glucocorticoid for 24 hours; the conditioned media were collected and frozen for ELISAs.
Real-Time Quantitative PCR Cells (7,500/well) in 96-well plates were lysed and reverse transcribed using the Cells-To-Ct kit (Ambion). Quantitative PCR was performed using the Roche Universal ProbeLibrary (UPL) and following primer-probe combinations: Tubulin-A (Probe 58; F:5'-CTT CGT CTC CGC CAT CAG-3' (SEQ ID NO:25), R:5'-TTG CCA ATC TGG ACA CCA-3' (SEQ ID NO:26)); IL-6 (Probe 45; F:5'-GCC CAG CTA TGA ACT CCT TCT-3' (SEQ ID NO:27), R:5'-GAA GGC AGC AGG CAA CAC-3' (SEQ ID NO:28)); IL-8 (Probe 72; F:5'-AGA CAG CAG AGC ACA CAA GC-3' (SEQ ID NO:29), R:5'-ATG GTT CCT TCC GGT GGT-3' (SEQ ID NO:30)); MMP-3 (Probe 36; F:5'-CAA AAC ATA TTT CTT TGT AGA GGA CAA-3' (SEQ ID NO:31), R: 5'-TTC AGC TAT TTG CTT GGG AAA-3' (SEQ ID NO:32)); GR (Probe 34; F: 5'-GAA AGC CAC GCT CCC TTC-3' (SEQ ID NO:33), R: 5'-AGA CTT AGG TGA AAC TGG AAT TGC T-3' (SEQ ID NO:34)); IL-1α (Probe 6; F: 5'-GGT TGA GTT TAA GCC AAT CCA-3' (SEQ ID NO:35), R: 5'-TGC TGA CCT AGG CTT GAT GA-3' (SEQ ID NO:36)); IκBα (Probe 86; F: 5'-GGT GCT GAT GTC AAT GCT CA-3' (SEQ ID NO:37), R: 5'-ACA CCA GGT CAG GAT TTT GC-3' (SEQ ID NO:38)).
Western Blotting Cells were lysed in RIPA buffer. Lysates were sonicated (10 sec), followed by centrifugation. Samples were incubated at 70° C. for 10 min, loaded on 4-15% gradient tris-glycine SDS-polyacrylamide gels (Invitrogen) and separated by electrophoresis. Proteins were transferred to PVDF membranes, blocked in TBST 5% milk for 1 hour at room temperature, and probed overnight at 4° C. with primary antibodies in blocking buffer. Membranes were washed in TBST, and incubated with horseradish peroxidase-conjugated secondary antibodies for 1 hour at room temperature. Blots were developed using Western detection substrate (GE Healthcare).

Immunofluorescence

Cells were cultured in 8-well chamber slides, fixed in 4% formaldehyde (Sigma) for 10 min at 4° C. and permeabilized in PBS-0.5% Triton for 10 min in 4° C. Slides were blocked for 30 min in 4% goat serum (Invitrogen). Primary antibodies were diluted in blocking buffer and incubated with cells for 1 hour at room temperature. Cells were washed, incubated with secondary antibodies for 30 min at room temperature, washed and mounted with slow-fade gold (Molecular Probes). Images were acquired using an Olympus BX20 fluorescence microscope with the spotfire software (Diagnostics Instruments) and processed with Photoshop CS (Adobe).

Antibodies

Primary antibodies and dilutions were: anti-GR (SC-8992, Santa Cruz; 1:500), anti-actin (ab6276, Abcam; 1:50000), anti-MCR (SC-11412, Santa Cruz; 1:500), anti-IRAK1 (SC-5288, Santa Cruz; 1:500), anti-IκBα (#9247, Cell Signaling; 1:500), anti-RelA (SC-109, Santa Cruz; 1:500), and anti-53BP1 (A300-272A, Bethyl; 1:500). Secondary antibodies used for western analysis were: goat anti-mouse IgG HRP conjugate (#170-5047, BioRad; 1:5000), and goat anti-rabbit IgG HRP conjugate (#166-2408, BioRad; 1:5000). Secondary antibody used for immunostaining was Alexa Fluor 488 goat anti-rabbit IgG (#A11008, Invitrogen; 1:750).

NF-κB Binding Activity and Transactivation Assays

Nuclear extracts were prepared using the nuclear extract kit (Active Motif), and NF-κB DNA binding was determined using the TransAM NF-κB p65 kit (Active Motif). For transactivation assays, cells infected with the NF-κB reporter-luciferase lentivirus were lysed in buffer (Promega), and luciferase activity was normalized to cell number, as described (Freund et al., 2011, *EMBO J.* 30:1536-1548).

Antibody Arrays

Cultures were washed and incubated in serum-free DMEM for 24 hours and the conditioned media were diluted to equivalent cell numbers using DMEM. Antibody arrays from Raybiotech (AAH-CYT-G1000-8) were used according to the manufacturer's instructions. Arrays were scanned using a GenePix 4200A Professional microarray scanner. Signal intensities were quantitated using LI-COR Odyssey software and normalized to positive controls for each sample, which were then normalized across all samples, as previously described (Freund et al., 2011, EMBO J. 30:1536-1548).

ELISA

Conditioned media were filtered and stored at −80° C. Cell numbers were determined in every experiment. ELISAs were performed using kits and procedures from PerkinElmer (IL-6 AL223F). Data were normalized and expressed as pg/ml/cell/24 h.

Invasion Assay

T47D human breast cancer cells (120,000 cells/well) were plated atop a layer of Matrigel in the upper chambers of Transwells (BD Biosciences). The lower chambers contained conditioned media from pre-senescent or senescent HCA2 fibroblasts treated with corticosterone or cortisol for 10 d. After 18 h, cells that migrated to the underside of the upper chamber filter were stained and counted, as described (Coppe et al., 2008, PLoS Biol. 6:2853-2868; Coppe et al., 2010, PLoS ONE 5:e9188).

Statistical Analysis

Error bars on all graphs represent the standard deviation of at least 3 independent measurements. For the antibody array, statistical significance between distributions of signals was evaluated using a two-tailed Student's t-test and assumption of equal variance with three conditioned medium samples per condition.

Glucocorticoids Suppress Selected Components of the Senescence-Associated Secretory Phenotype To identify small molecules that may be potential SASP modulators, a screening strategy that entailed administering compounds to parallel 96-well plates containing human fibroblasts (strain HCA2) that were either quiescent or senescent was developed. The compounds tested comprised the Prestwick Chemical Library, a collection of approximately 1,120 Federal Drug Administration-approved drugs. The compounds were added to duplicate wells at a single concentration (2.5 µM). After 48 hours, the medium from each well was removed, and the cells were lysed. ELISAs were used to detect the presence of IL-6 in the medium, a major SASP factor, as an indication of whether a compound suppressed or enhanced the SASP. Cell lysates were assayed for ATP as a surrogate for cell number. The results of the ATP assay allowed elimination highly toxic compounds, or compounds that grossly altered cell number.

Of the 1,120 drugs tested, several suppressed IL-6 secretion without altering ATP levels. These drugs, then, were candidates for having the ability to suppress the SASP without causing cell toxicity or reversing the senescence growth arrest. The candidate drugs included the following: corticosterone, cortisol, prednisone, androsterone, tolazamide, chlorpropamide, gliclazide, finasteride, norgestrel-(−)-D, estradiol-17-beta, minoxidil, and benfotiamine. Among these candidates the hormones of the glucocorticoid family, such as corticosterone were the most potent.

Figures 12A, 12B:
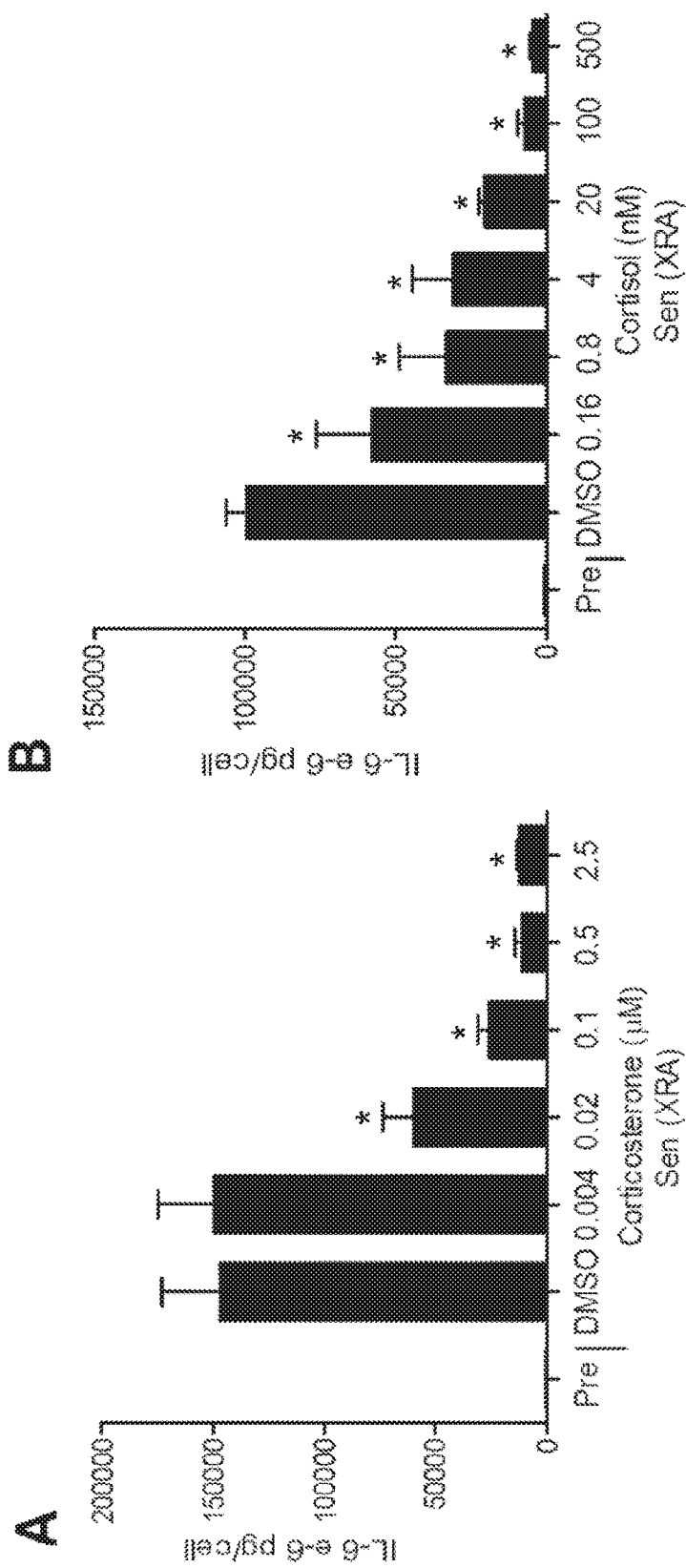
FIGS. 12A-12E show that corticosterone and cortisol partially suppress the SASP.
Figure 16B:
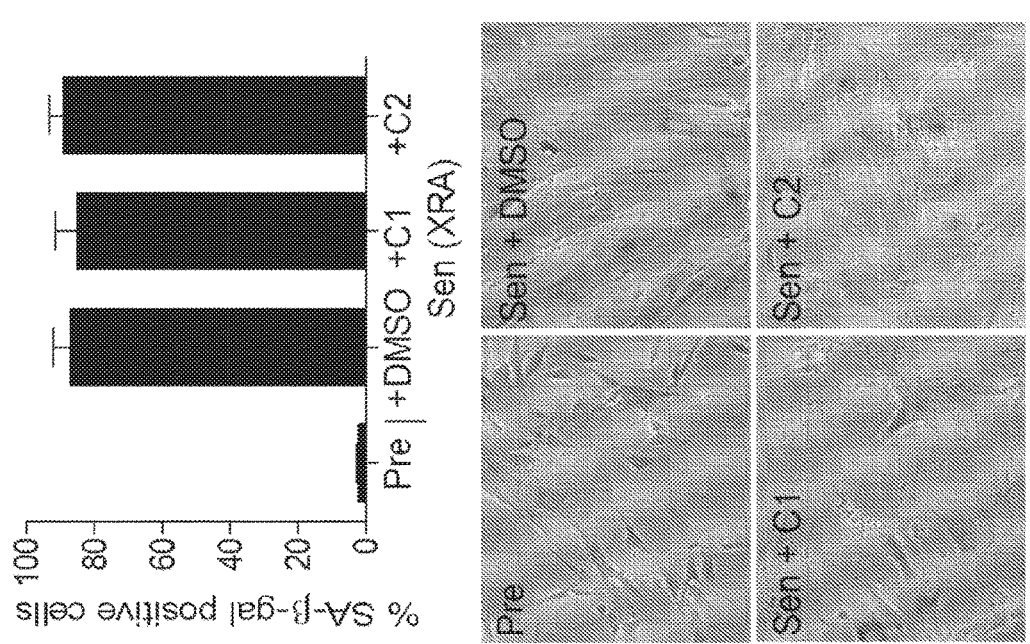
Figure 16A:
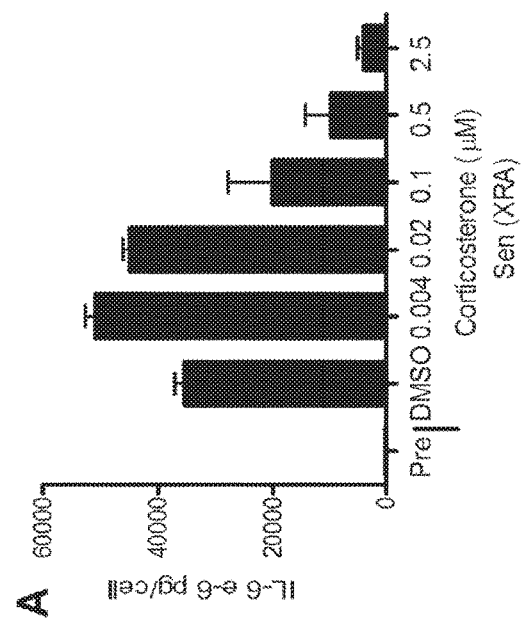

To confirm the ability of corticosterone to suppress senescence-associated IL-6 secretion, fresh HCA2 fibroblast cultures were prepared, and senescence was induced by X-irradiation (10 Gy). Under these conditions, cells undergo growth arrest within 24-48 hours, but require 4-5 days before SASP components are detected in the medium (Coppe et al., 2008, PLoS Biol. 6:2853-2868; Rodier et al., 2009, Nature Cell Biol. 11:973-979; Coppe et al., 2010, PLoS ONE 5:e9188; Freund et al., 2011, EMBO J. 30:1536-1548). Varying concentrations of corticosterone were added immediately after irradiation, and the cells were maintained in the drug for 6 days. On the $6^{th}$ day, the cells were incubated in serum-free medium with or without corticosterone, the conditioned medium was collected 24 h later, and the medium was assayed for IL-6 by ELISA. Corticosterone decreased IL-6 secretion in a dose-dependent manner (FIG. 12A). At 20 nM, corticosterone reduced IL-6 secretion by approximately 50%; maximal suppression (>90%) was achieved at 500 nM. The ability of corticosterone to suppress IL-6 secretion by senescent cells was not peculiar to HCA2 cells. A similar reduction was observed using another human fibroblast strain (IMR-90 from fetal lung) (FIG. 16A).

Corticosterone is the main GR ligand in rodents and other species; however, in humans, the main GR ligand is the closely related glucocorticoid cortisol (Gross and Cidlowski, 2008, Trends Endocrinol. Metab. 19:331-339; Zanchi et al., 2010, J. Cell Physiol. 224:311-315). Therefore, cortisol was tested for the ability to suppress IL-6 secretion by human fibroblasts induced to senesce by X-irradiation. Cortisol decreased IL-6 secretion in a dose-dependent manner, and was more potent than corticosterone (FIG. 12B). Cortisol reduced senescence-associated IL-6 secretion by 50% at sub-nM concentrations (160-800 pM) and >90% at 100 nM.

Figure 12C:
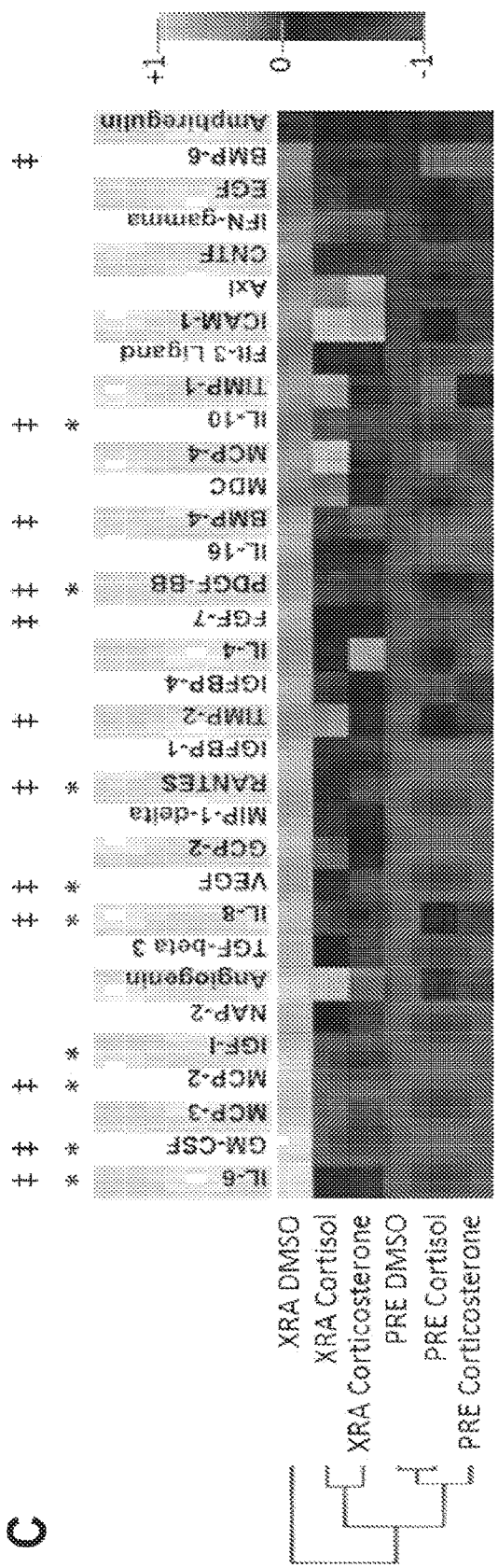

To determine whether or not, or to what extent corticosterone or cortisol suppressed the entire SASP, antibody arrays were used to interrogate the relative secretion of 120 cytokines and growth factors. Presenescent and senescent cells were incubated with 500 nM corticosterone or 100 nM cortisol (FIG. 12C). Both glucocorticoids strongly suppressed the secretion of several pro-inflammatory cytokines and chemokines, including IL-6, IL-8, GM-CSF and MCP-2. In addition, they suppressed the secretion of several growth and angiogenic factors such as VEGF. Neither glucocorticoid suppressed all components of the SASP (FIG. 12C), and thus were selective SASP modulators.

The ability of corticosterone and cortisol to suppress senescence-associated IL-6 secretion was not limited to cells induced to senesce by X-irradiation. Both glucocorticoids were effective in cells induced to senesce by overexpression of oncogenic RAS or MKK6 (mitogen-activated protein kinase kinase 6) (FIG. 12D), which induce a growth arrest, cell enlargement, senescence-associated β-galactosidase (SA-Bgal) expression and a robust SASP (Coppe et al., 2008, PLoS Biol. 6:2853-2868; Freund et al., 2011, EMBO J. 30:1536-1548).

Figures 12D, 12E:
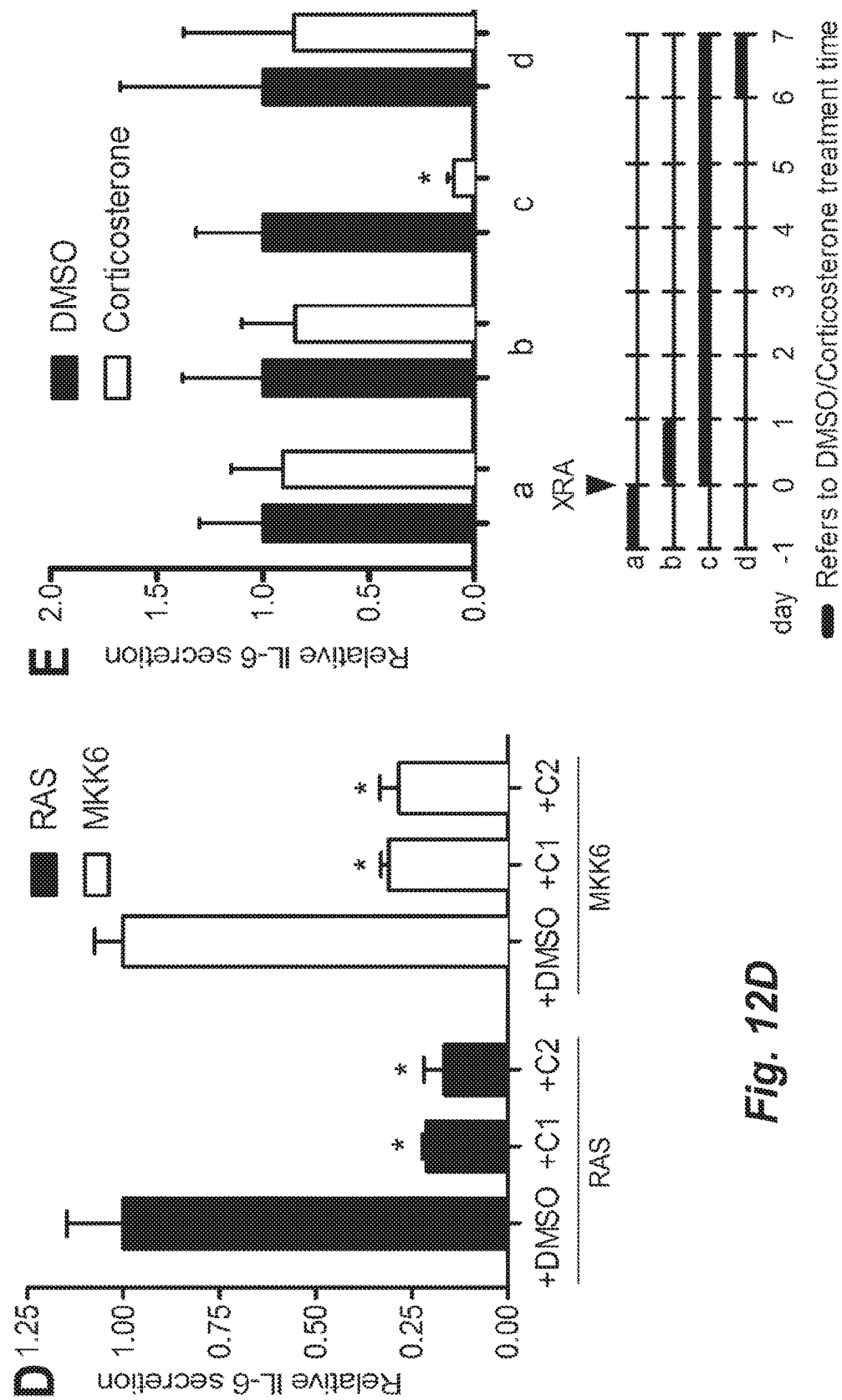

The suppression of IL-6 secretion by glucocorticoids required that the steroids be present for an extended period during which the SASP is being established. In irradiated cells, which induces senescence synchronously, the SASP takes 3-4 days, beginning 1-2 days after irradiation, to become established (Coppe et al., 2008, PLoS Biol. 6:2853-2868; Rodier et al., 2009, Nature Cell Biol. 11:973-979). Pretreating cells with corticosterone prior to inducing senescence by X-irradiation, or treating for only 24 hours immediately following irradiation or after establishment of the SASP (7 days after irradiation), had no effect on IL-6 secretion (FIG. 12E). However, continuous exposure to corticosterone for 7 days after irradiation strongly suppressed IL-6 secretion (FIG. 12E).

In contrast to their effects on the SASP, corticosterone and cortisol had no effect on the fraction of cells that expressed SA-Bgal (FIG. 16B) or the enlarged senescent morphology. Moreover, neither glucocorticoid reversed the senescence growth arrest. Thus, cells made senescent by X-irradiation and treated with corticosterone or cortisol for 7 days maintained their low 24 h BrdU labeling index (FIG. 16C). Furthermore, although the SASP depends on constitutive low level DNA damage response (DDR) signaling (Rodier et al., 2009, Nature Cell Biol. 11:973-979) emanating from persistent DNA damage foci (Rodier et al., 2011, J. Cell Sci. 124:68-81), corticosterone and cortisol had no effect on the number of persistent DNA damage foci in the nuclei of cells induced to senescent by X-irradiation (FIG. 16D; 16E).

These results demonstrate the feasibility of screening for compounds that selectively reduce the secretion of proteins secreted by senescent cells, including the secretion of pro-inflammatory cytokines. The dual approach of assaying cellular ATP levels to detect substantial cell loss or gain coupled to ELISAs for the prototypical SASP protein IL-6 allowed identification of compounds with potential SASP-suppressing activity, but without gross toxicity or, equally importantly, the ability to reverse the senescence growth arrest. Taken together, the data show that corticosterone and cortisol decrease the secretion of prominent SASP factors without affecting other prominent senescent phenotypes, including the growth arrest, and were efficacious whether cells were induced to senesce by ionizing radiation or strong mitogenic signals delivered by oncogenic RAS or MAP kinase kinase 6 overexpression.

Glucocorticoids Mediate Suppression of SASP Through Glucocorticoid Receptor

Because most SASP factors are upregulated at the level of mRNA abundance (Coppe et al., 2008, PLoS Biol. 6:2853-2868; Coppe et al., 2010, PLoS ONE 5:e9188), the effects of the glucocorticoids on the mRNA levels of three important SASP factors (IL-6, IL-8, MMP-3) (FIG. 13A1) were determined. mRNA was extracted from presenescent (Mock) or senescent X-irradiated HCA2 cells treated with DMSO, 500 n corticosterone, or 100 nm cortisol as described herein. All three mRNAs were strongly reduced by corticosterone and cortisol (FIG. 13A1), suggesting that the glucocorticoids act at the level of transcription. In a second experiment, mRNA levels of SASP factors IL-5, IL-6, IL-8, MMP-3, IL-1α, MCP-2, MCP-3, and GM-CSF were determined (see FIG. 13A2).

Figure 13B:
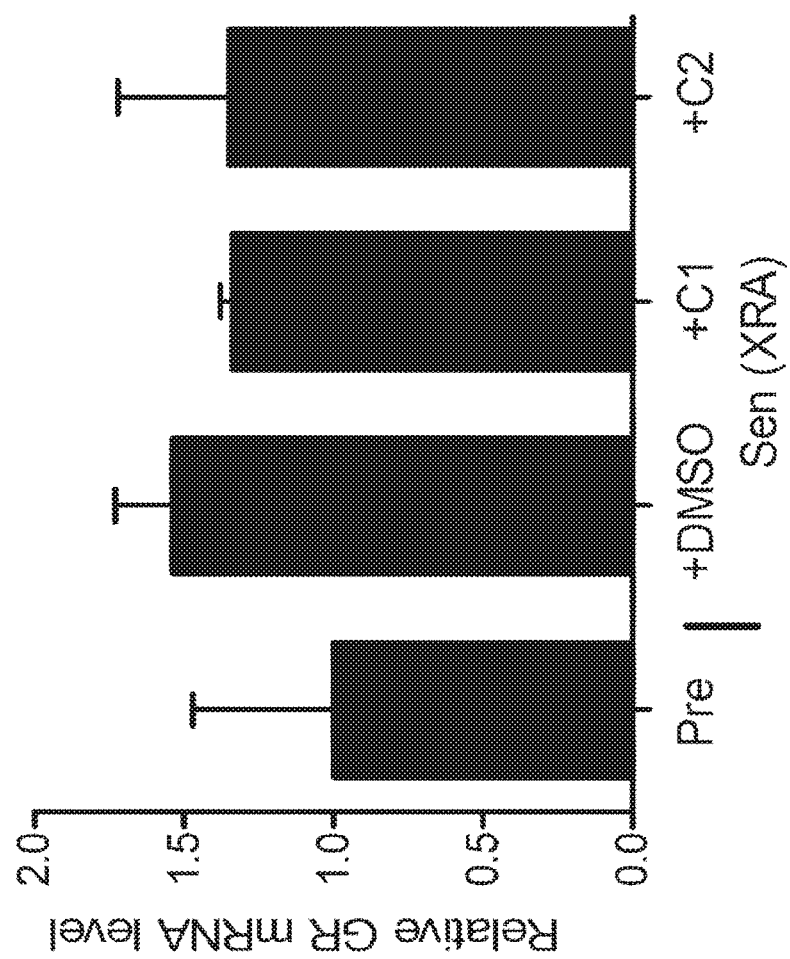
(FIG. 13B) mRNA was extracted from Pre and Sen (XRA) cells treated with DMSO, 500 nM corticosterone (C1), or 100 nM cortisol (C2) as previously described, and transcripts for GR were quantified by PCR (normalized to tubulin). Although GR mRNA levels tended to be slightly elevated in senescent cells, the increase was not statistically significant.
Figure 13C:
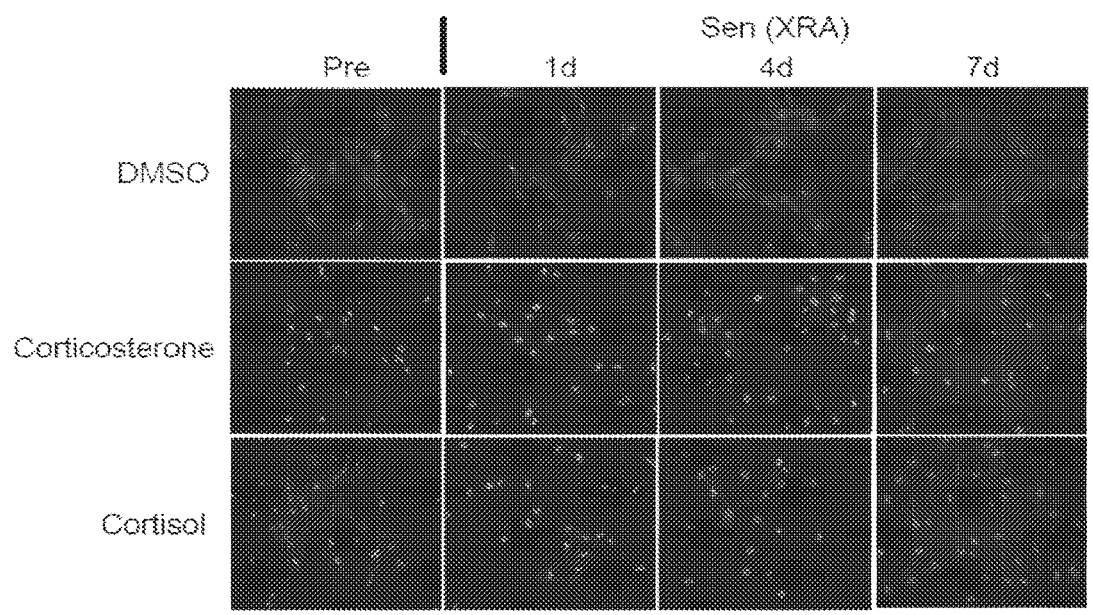
(FIG. 13C) Pre and Sen (XRA) cells treated with DMSO, 500 nM corticosterone, or 100 nM cortisol as previously described were immunostained for GR 1, 4, and 7 days after X-irradiation.

Glucocorticoids are ligands for GR isoforms, which, upon ligand binding, translocate to the nucleus where they alter the transcription of numerous genes; most of the physiological effects of glucocorticoids depend on the GR (Gross and Cidlowski, 2008, Trends Endocrinol. Metab. 19:331-339; Zanchi et al., 2010, J. Cell Physiol. 224:311-315; Oakley and Cidlowski, 2011, J. Biol. Chem. 286:3177-3184). GR expression levels were measured for change as a consequence of senescence or addition of corticosterone or cortisol (FIG. 13B). GR mRNA levels appeared to slightly increase in senescent, relative to presenescent, cells and were unaffected by glucocorticoid addition. The GR was largely cytoplasmic in presenescent cells, and remained cytoplasmic up to 7 days after the cells were induced to senesce by X-irradiation (FIG. 13C). However, the GR translocated into the nucleus in response to either corticosterone or cortisol (FIG. 13C), indicating that both these glucocorticoids can activate the GR. In contrast, the related mineralocorticoid receptor, which also binds cortisol and can physically interact with the GR, remained cytoplasmic after corticosterone or cortisol addition (FIG. 17A). Thus, corticosterone and cortisol each specifically induce GR nuclear localization in senescent HCA2 cells.

Figure 13D:
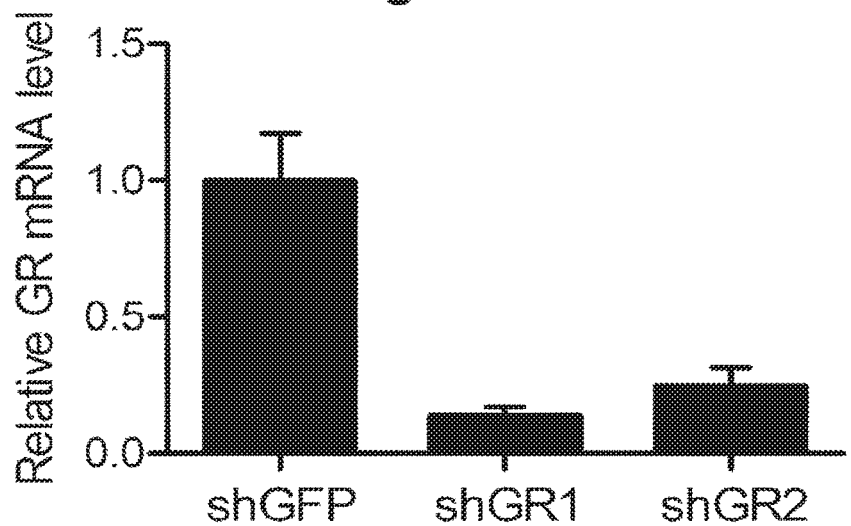
(FIG. 13D) Cells were infected with lentiviruses expressing shRNAs against GFP (control) or GR and selected. Seven days after selection, mRNA was extracted and transcripts for GR were quantified by PCR (normalized to tubulin).
Figure 13E:
(FIG. 13E) Total cell clysates were prepared from the shGFP- and shGR-expressing cells described in (FIG. 13D) and analyzed by western blotting for GR and actin (control).
Figure 13G:
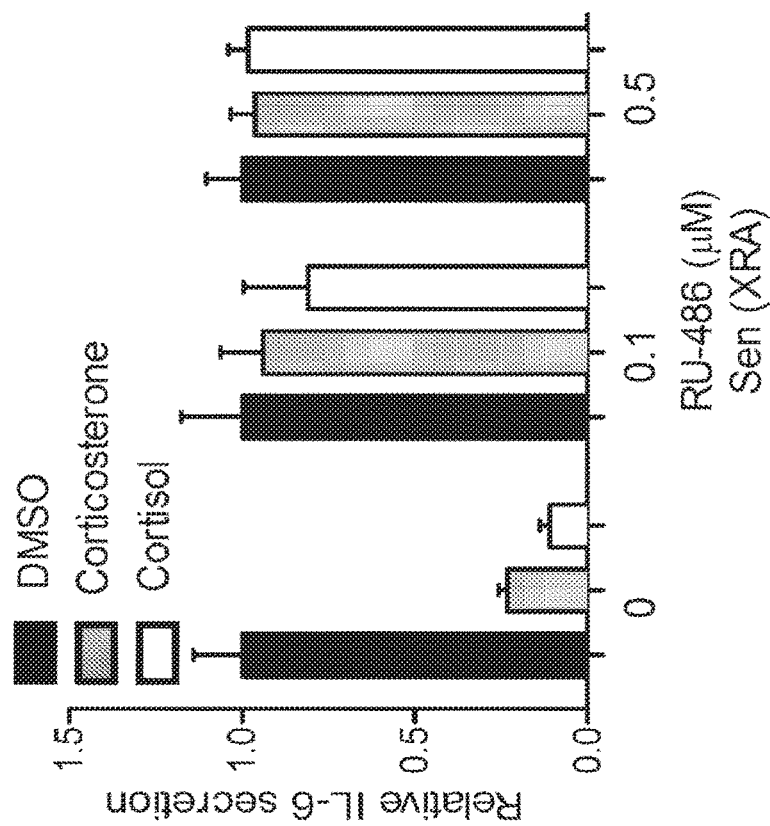
Figure 13F:
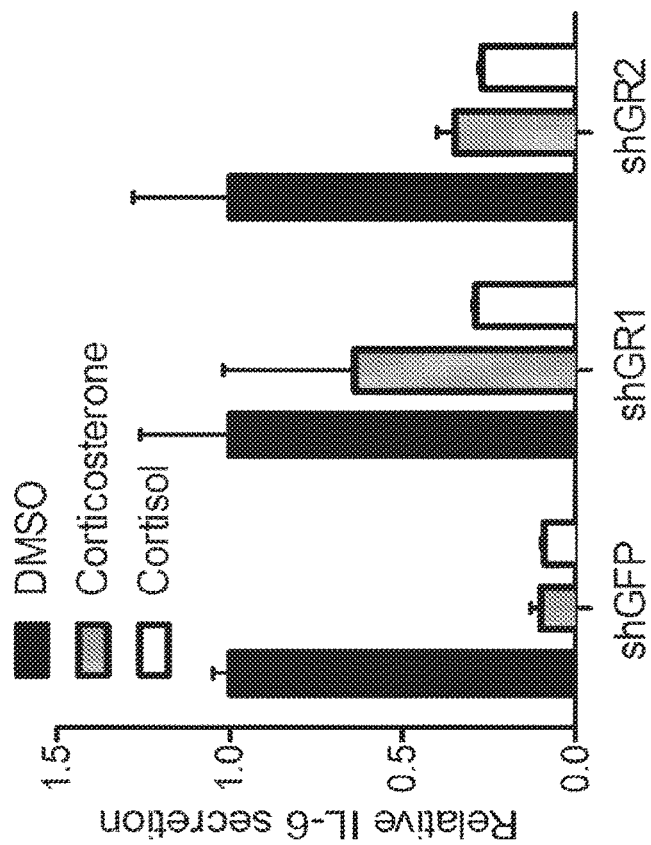
(FIG. 13F) Cells infected with shGFP- or shGR-expressing lentiviruses were X-irradiated and treated immediately thereafter with DMSO, 500 nM corticosterone, or 100 nM cortisol. Conditioned media were collected 7 days later and analyzed by ELISA for IL-6.

To determine whether the ability of corticosterone and cortisol to suppress the expression of selected SASP components was mediated by the GR, RNA interference (RNAi) and lentiviruses that express short hairpin (sh) RNAs designed to deplete cells of the GR were used. Quantitative PCR and western blotting confirmed that two distinct shRNAs reduced GR mRNA and protein levels (FIG. 13D; 13E). GR depletion partially rescued the suppression of IL-6 secretion by corticosterone and cortisol (FIG. 13F). This partial rescue may be due to incomplete GR depletion by the shRNAs (FIG. 13D; 13E). Consistent with these results, co-treatment of senescent cells with corticosterone or cortisol plus the glucocorticoid antagonist RU-486 (Cadepond et al., 1997, Annu. Rev. Med. 48:129-156; Lewis-Tuffin et al., 2007, Molec. Cell Biol. 27:2266-2282) rescued the senescence-associated IL-6 secretion that was suppressed by the glucocorticoids (FIG. 13G). RU-486 blocked this glucocorticoid activity without affecting GR nuclear translocalization (FIG. 17B).

Taken together, these results show that both corticosterone and cortisol induced GR nuclear translocalization in senescent cells, which suppressed IL-1α signaling by inhibiting NF-κB DNA binding and transactivation activity. Moreover, because genetic or pharmacological inhibition (RU-486) of the GR rescued the suppression of senescence-associated IL-6 secretion by glucocorticoids, the results suggest the GR is required for the suppressive effects of glucocorticoids in senescent cells.

Glucocorticoids Suppress the Expression of IL-1α, an Upstream SASP Regulator

It has been previously demonstrated that IL-1α is a critical upstream regulator of the SASP (senescence-associated IL-6/IL-8 cytokine network) (Orjalo et al., 2009, Proc. Natl. Acad. Sci. USA 106:17031-17036). IL-1α establishes and maintains the SASP by activating the transcription factor nuclear factor-kappa B (NF-κB) (Orjalo et al., 2009, Proc. Natl. Acad. Sci. USA 106:17031-17036; Freund et al., 2011, EMBO J. 30:1536-1548), which further stimulates IL-1α transcription, thereby establishing a positive feedback loop (Freund et al., 2010, Trends Molec. Med. 16:238-248). This positive feedback loop leads to increased NF-κB activation and, consequently, the transcription of several SASP factors. Therefore, whether glucocorticoids suppressed the SASP by interfering with IL-1α expression was examined.

Figure 14B:
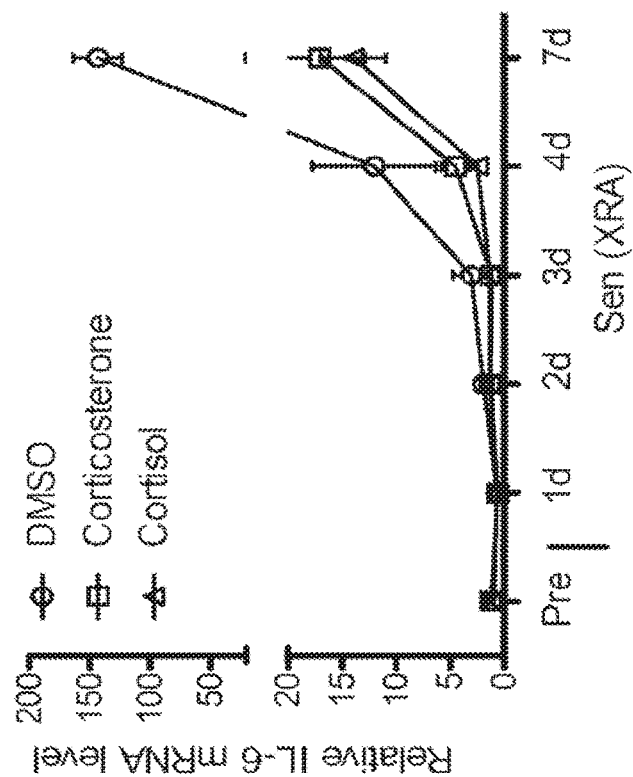
FIGS. 14A-14C show that glucocorticoids repress IL-1α expression.
Figure 14A:
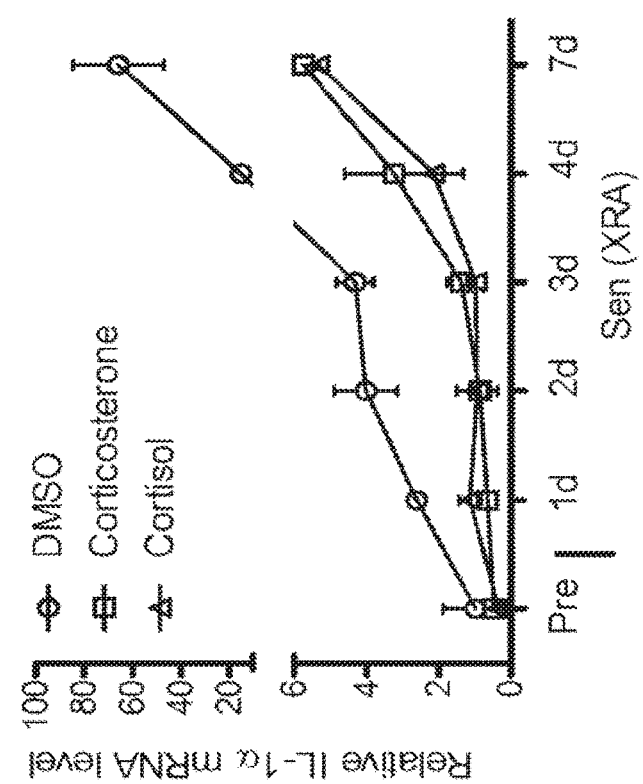

IL-1α mRNA rose rapidly after cells were induced to senesce by X-irradiation (FIG. 14A). When added at the time of irradiation, both corticosterone and cortisol delayed this rise, as well as the later rise in IL-6 mRNA (FIG. 14A; 14B). Further, the glucocorticoids continued to suppress IL-1α and IL-6 mRNA levels (<10% of control) for at least 7 days after irradiation, at which time the SASP is normally fully developed (Coppe et al., 2008, PLoS Biol. 6:2853-2868; Rodier et al., 2009, Nature Cell Biol. 11:973-979).

Figure 14C:
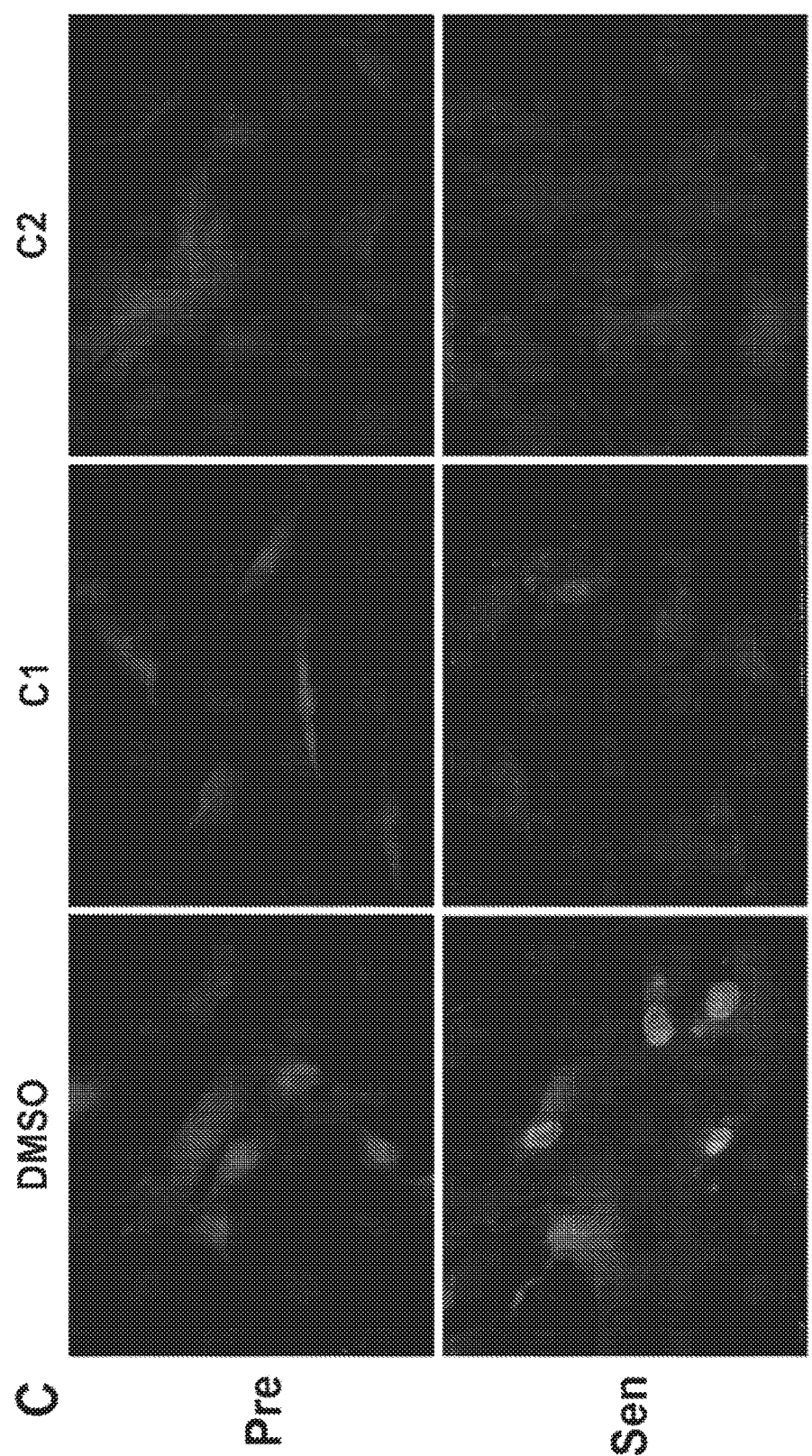

IL-1α localizes to both the plasma membrane and the nucleus (Werman et al., 2004, Proc. Natl. Acad. Sci. USA 101:2434-2439; Orjalo et al., 2009, Proc. Natl. Acad. Sci. USA 106:10731-10736). Consistent with the suppression of IL-1α mRNA levels, corticosterone and cortisol also suppressed expression of IL-1α protein, which was visible as strong nuclear staining in control, but not glucocorticoid-treated, senescent cells (FIG. 14C).

Glucocorticoids Impair the IL-1α/NF-κB Pathway

Figure 15A:
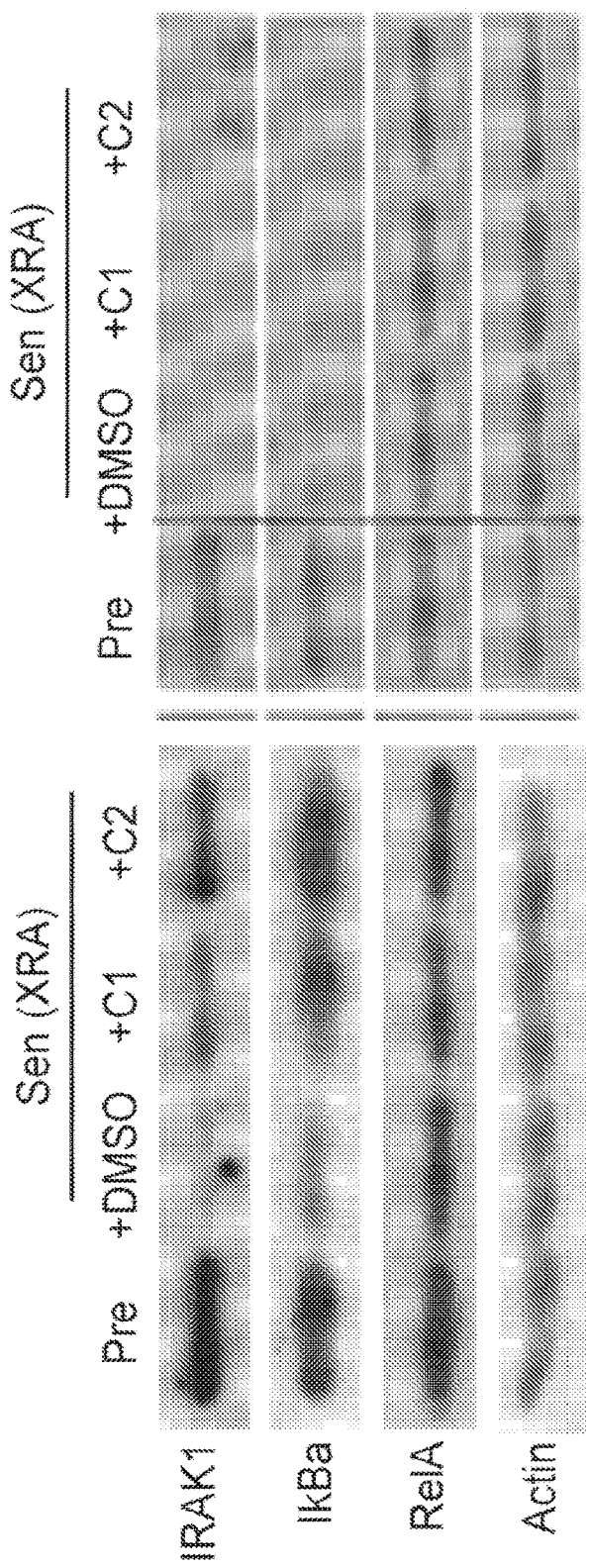
FIGS. 15A-15F show that glucocorticoids impair the IL-1α/NF-κB pathway and suppress the ability of the SASP to induce tumor cell invasion.
Figure 18:
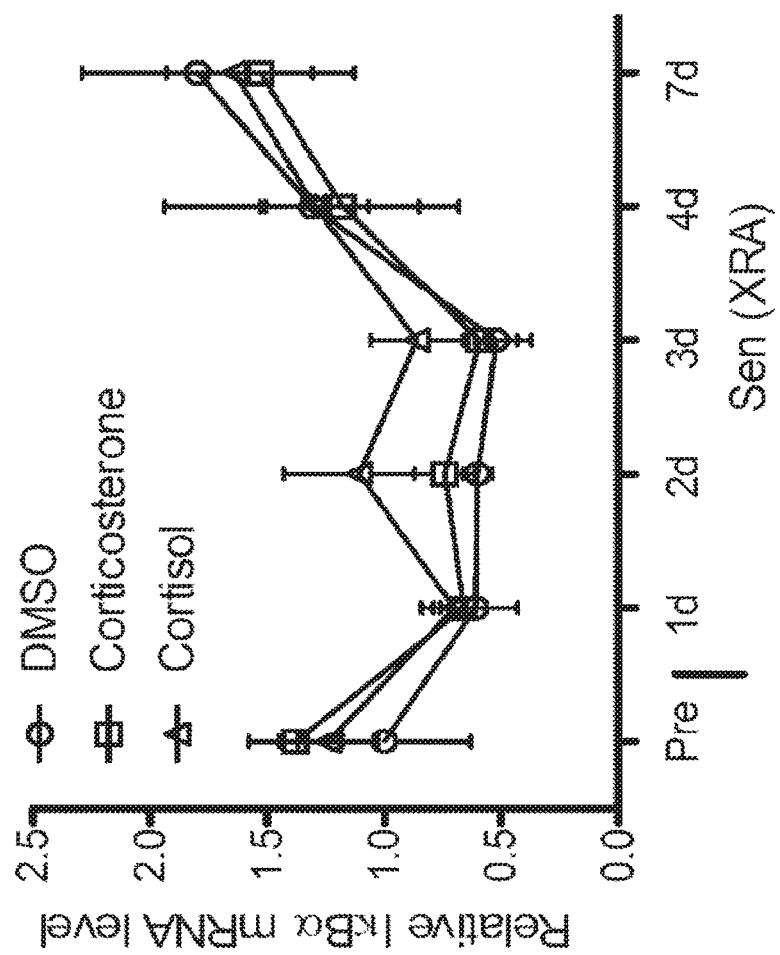
FIG. 18 mRNA extracted from Pre HCA2 cells treated with DMSO, 500 nM corticosterone, or 100 nM cortisol for 24 hours and Sen (XRA) HCA2 cells treated with these compounds for 7 days starting immediately after X-irradiation. mRNA extracts were analyzed for IκBα transcripts by quantitative PCR (normalized to tubulin). The level of IκBα mRNA in DMSO-treated Pre cells was arbitrarily assigned a value of 1.

To determine whether glucocorticoids suppress the SASP by suppressing IL-1α signaling, the abundance of interleukin-1 receptor-associated kinase 1 (IRAK1) and IκBα, an inhibitor of NF-κB were measured. Both these proteins are key components of IL-1α/IL-1 receptor (IL-1R) signaling (Perkins, 2007, Nature Rev. Molec. Cell Biol. 8:49-62; Gottipati et al., 2008, Cell Signal. 20:269-276), and are rapidly degraded after the IL-1R is engaged by IL-1α (Perkins, 2007, Nature Rev. Molec. Cell Biol. 8:49-62; Gottipati et al., 2008, Cell Signal. 20:269-276; Orjalo et al., 2009, Proc. Natl. Acad. Sci. USA 106:17031-17036). IRAK1 and IκBα were much less abundant in senescent, compared to presenescent, cells, indicating active IL-1R signaling in senescent cells (FIG. 15A). The abundance of RelA, an NF-κB subunit, was unchanged. Consistent with the suppression of IL-1α production and blockade of IL-1R signaling, corticosterone and cortisol restored IRAK1 and IκBα proteins to near-presenescent levels (FIG. 15A). Moreover, the glucocorticoids had no effect on IκBα mRNA levels (FIG. 18), suggesting they acted indirectly to reduce protein levels and consistent with their effect on IL-1α mRNA levels.

Figure 15C:
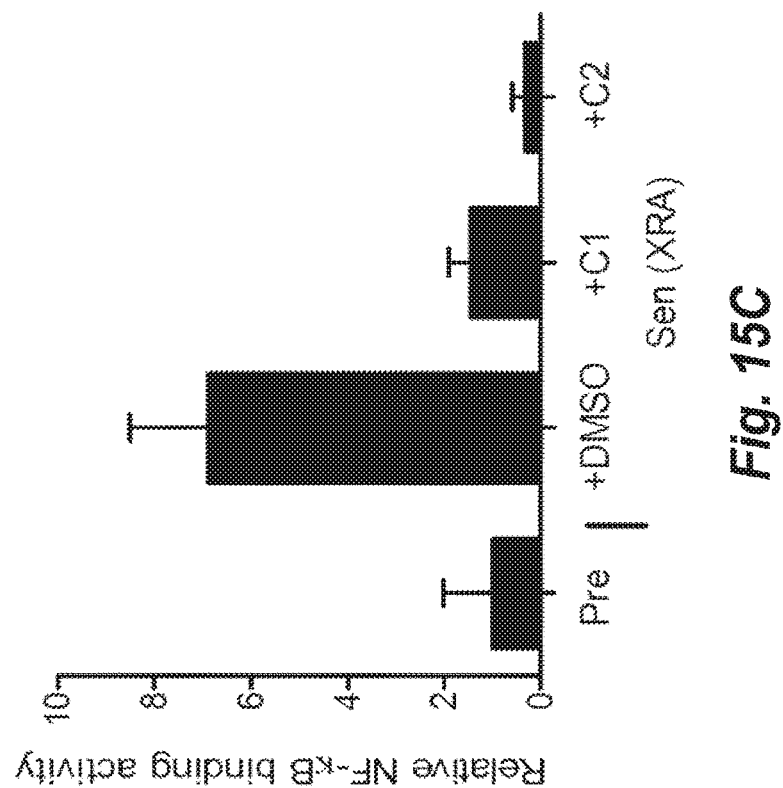
Figure 15B:
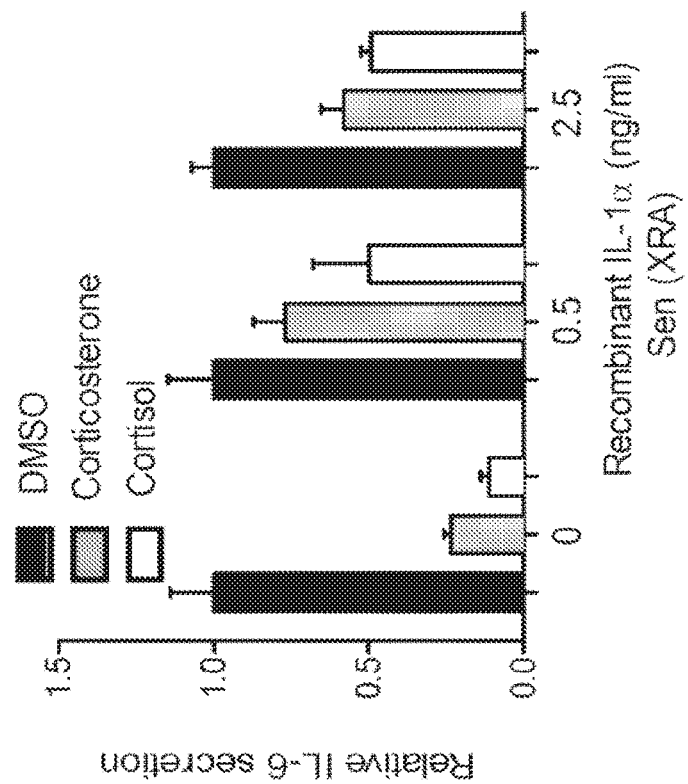
Figures 15D, 15E:
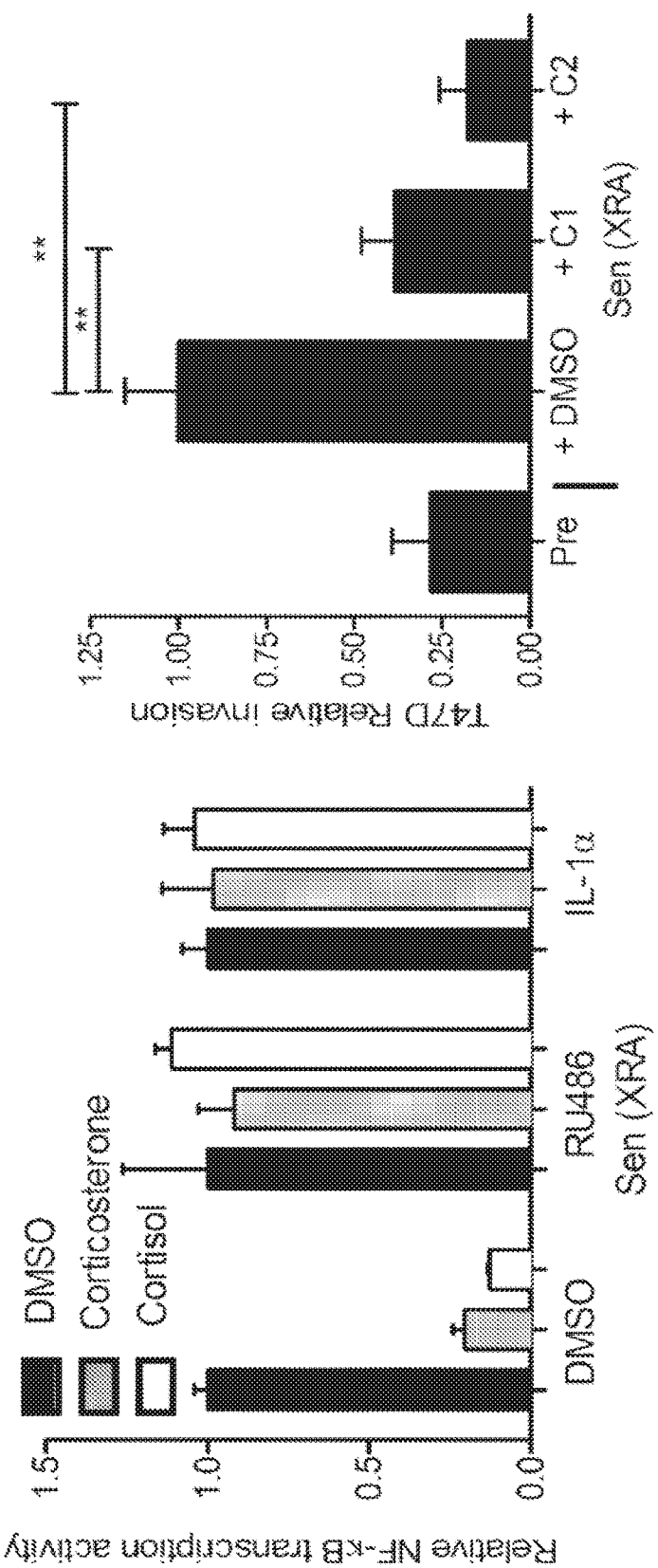
Figure 15F:
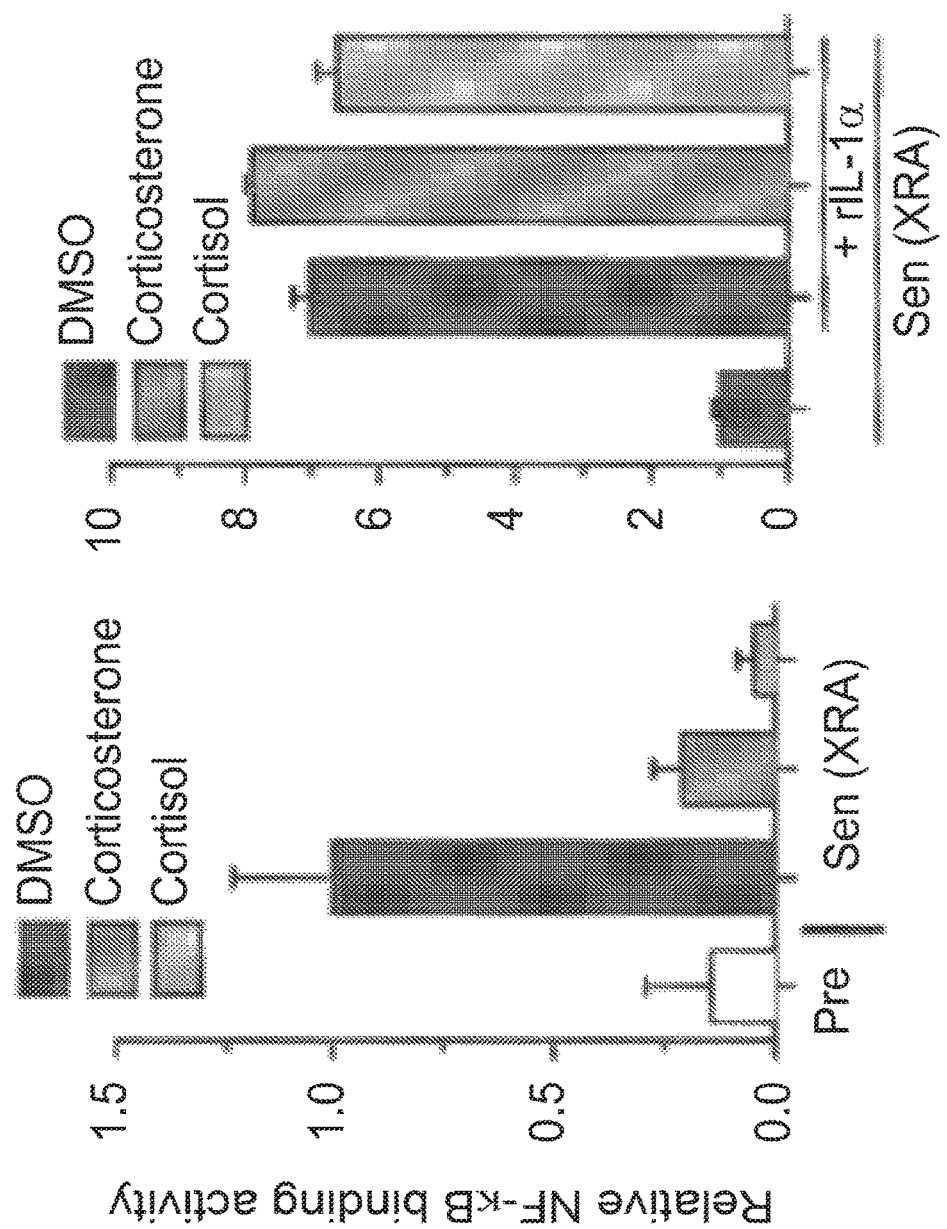

Recombinant IL-1α rescued the suppression of IL-6 secretion by corticosterone and cortisol (FIG. 15B), consistent with the idea that glucocorticoids suppress SASP components such as IL-6 by targeting IL-1α/IL-1R signaling. Because GRs are known to modulate NF-κB activity, one potential mechanism by which glucocorticoids might act in this regard is by inhibiting NF-κB activity. In support of this model, corticosterone and cortisol significantly decreased both NF-κB DNA binding and transactivation activity in senescent cells (FIG. 15C; 15D, 15F). Furthermore, co-treatment of senescent cells with either of the glucocorticoids plus RU-486 (glucocorticoid antagonist) or recombinant IL-1α rescued NF-κB transactivation activity (FIG. 15D). Without wishing to be bound by theory, glucocorticoids, acting via the GR, appear to suppress the SASP at least in part by preventing establishment of the IL-1α/NF-κB positive feedback loop that ultimately drives the expression and secretion of SASP components by impairing IL-1α expression. Once established, however, the feedback loop appears to be unaffected by glucocorticoids. Thus, the transcriptional landscape that allows establishment of the SASP may differ from the transcriptional landscape that maintains it.

Glucocorticoids Suppress the Ability of the SASP to Stimulate Tumor Cell Invasion Senescent cells secrete factors that can stimulate aggressive cancer-associated phenotypes in premalignant or malignant cells (Krtolica et al., 2001, Proc. Natl. Acad. Sci. USA 98:12072-12077; Liu and Hornsby, 2007, Cancer Res. 67:3117-3126; Coppe et al., 2008, PLoS Biol. 6:2853-2868; Bartholomew et al., 2009, Cancer Res. 69:2878-2886; Coppe et al., 2010, PLoS ONE 5:e9188). Therefore, whether glucocorticoids suppressed the ability of the SASP to stimulate non-aggressive human breast cancer cells (T47D) to invade a basement membrane in Boyden chambers was investigated. Conditioned media prepared from presenescent cells stimulated minimal invasion by T47D cells, whereas media from senescent cells stimulated 4-fold more invasion (FIG. 15E), as expected. Both corticosterone and cortisol reduced the ability of senescent conditioned media to stimulate T47D invasiveness to near-presenescent levels. Thus, in addition to suppressing the secretion of multiple SASP factors, the glucocorticoids suppressed an important biological property of the SASP.

Flavonoid Apigenin Suppresses Selected Components of the Senescence-Associated Secretory Phenotype Using the screening protocol described previously for identifying potential SASP modulators from a compound library using HCA2 human fibroblasts that were either quiescent (non-senescent; mock-irradiated) or induced to senescence by X-irradiation, flavonoid was also identified, along with glucocorticoids, as being capable of suppressing IL-6 secretion without altering ATP levels. Apigenin (4',5, 7-trihydroxyflavone) is a naturally occurring plant flavone present in common fruits and vegetables.

Figure 19:
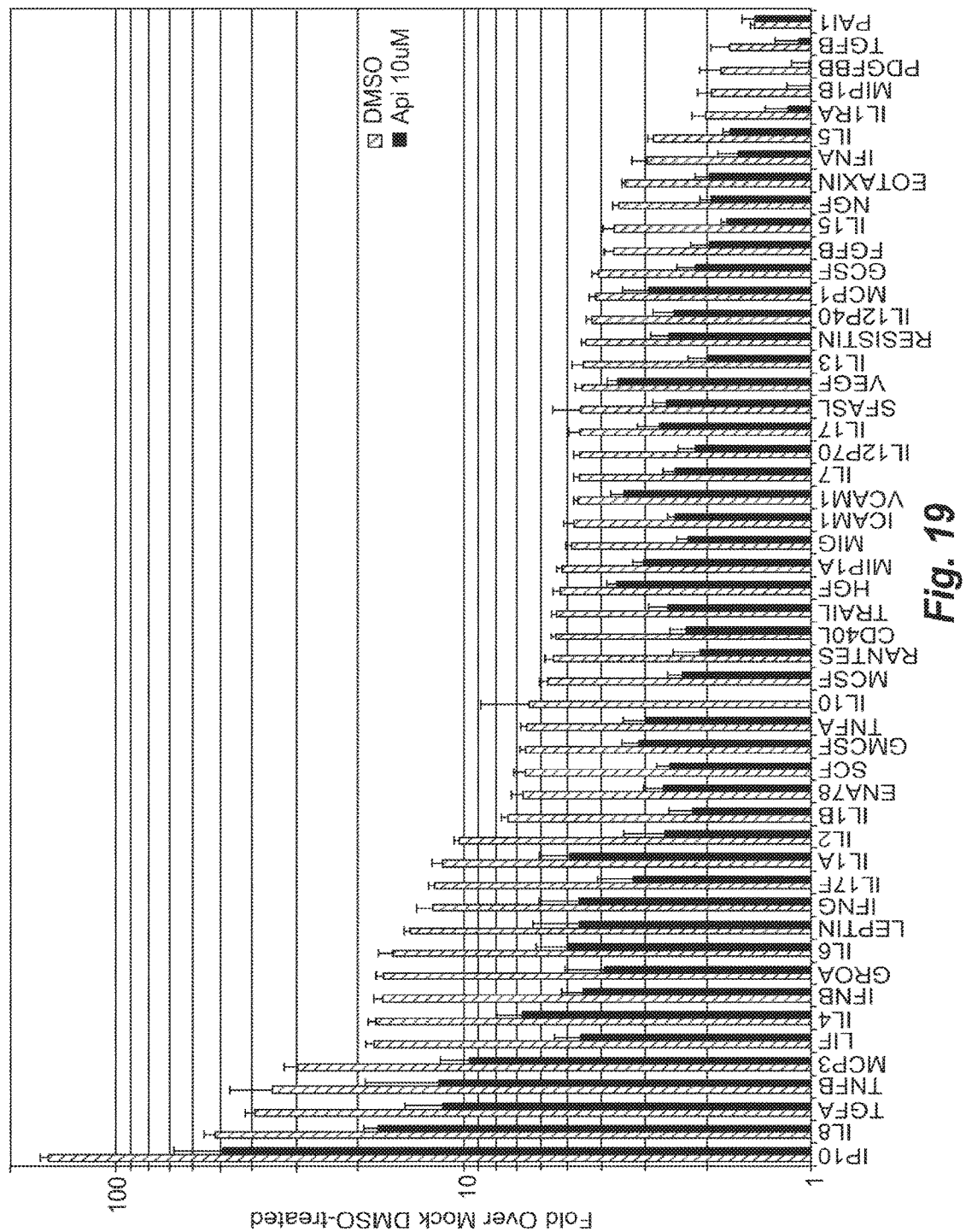
FIG. 19 shows that apigenin treatment partially suppresses SASP. Conditioned media from control (Mock irradiated, DMSO-treated), DMSO-treated (DMSO) or apigenin-treated senescent (Api) cells were analyzed by multiplex ELISA for expression of SASP. Results are shown as fold difference over control (Mock irradiated, DMSO-treated) cells with the vertical axis in log scale.

To determine whether or to what extent apigenin suppressed the entire SASP, multiplex ELISA was used to interrogate the relative secretion of 50 cytokines and growth factors. IMR90 fibroblasts were treated with 10 μM apigenin or DMSO immediately after irradiation and analyzed 6 days later. Cells were washed and incubated in serum-free media without apigenin to generate conditioned media. Conditioned media from non-senescent, apigenin- or DMSO-treated irradiated IMR90 cells and control (mock-irradiated, DMSO-treated) cells were analyzed by ELISA for various SASP factors (FIG. 19). As shown in FIG. 19, apigenin suppressed the secretion of several pro-inflammatory cytokines and chemokines, including, for example, TGFA, MCP3, LIF, IFNβ, IL-6, GROA, and IL-2. Those SASP factors suppressed by less than 2 fold were not considered to be significantly suppressed.

The various embodiments described above can be combined to provide further embodiments. All of the U.S. patents, U.S. patent application publications, U.S. patent applications, foreign patents, foreign patent applications and non-patent publications referred to in this specification and/or listed in the Application Data Sheet are incorporated herein by reference, in their entirety. Aspects of the embodiments can be modified, if necessary to employ concepts of the various patents, applications and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

We claim the following:

1. A method of inhibiting activity of a senescent cell in a cell population, wherein the senescent cell is characterized as expressing senescence-associated beta-galactosidase, the method comprising:
    suppressing expression of senescence-associated secretory phenotype (SASP) by the senescent cell by applying to the cell population an amount of a glucocorticoid that is effective in causing expression of the SASP by the senescent cell to be suppressed; and
    confirming that the amount of the glucocorticoid is effective by measuring expression of SASP by the cell population.

2. The method of claim 1, wherein the amount of the glucocorticoid causes expression of IL-6 by the senescent cell to be suppressed.

3. The method of claim 1, wherein the amount of the glucocorticoid causes expression of IL-6, IL-8, GM-CSF and MCP-2 by the senescent cell to be suppressed.

4. The method of claim 1, wherein the amount of the glucocorticoid causes suppression of VEGF by the senescent cell to be suppressed.

5. The method of claim 1, wherein the fraction of cells expressing senescence-associated beta-galactosidase is not altered in the cell population by the glucocorticoid.

6. The method of claim 1, wherein the glucocorticoid is corticosterone.

7. The method of claim 1, wherein the glucocorticoid is cortisol.

8. The method of claim 1, wherein the senescent cell is contacted with the glucocorticoid in vitro.

9. The method of claim 1, wherein the amount of the glucocorticoid reduces the likelihood of side effects mediated by the senescent cell following senescence inducing radiotherapy or chemotherapy.

10. The method of claim 9, wherein the senescent cell is contacted with the glucocorticoid at least two days prior to administration of the radiotherapy or the chemotherapy.

11. The method of claim 1, wherein the amount of the glucocorticoid improves the effectiveness of chemotherapy.

12. The method of claim 11, wherein the amount of the glucocorticoid reduces the number of metastases of a primary tumor.

13. A method of reducing the likelihood of side effects of radiotherapy or chemotherapy in a subject that has cancer, comprising:
    removing or reducing activity of senescent cells in the subject prior to administration of the radiotherapy or the chemotherapy by administering to the subject an effective amount of a glucocorticoid; and
    confirming that as a consequence of administering the glucocorticoid, the activity of the senescent cells has been reduced by determining expression of senescence-associated secretory phenotype (SASP) by the senescent cells.

14. The method of claim 13, wherein the subject is administered corticosterone or cortisol.

15. The method of claim 13, wherein the removing or reducing activity of the senescent cells causes reduction in the number of metastases of the cancer in the subject.

* * * * *

SEQUENCE LISTING

```
<160> NUMBER OF SEQ ID NOS: 38

<210> SEQ ID NO 1
<211> LENGTH: 9267
<212> TYPE: DNA
<213> ORGANISM: Artificial Sequence
<220> FEATURE:
<223> OTHER INFORMATION: pBLUESCRIPT II KS vector containing a p16Ink4a
      promoter-FKBP-caspase-IRES-GFP nucleic acid construct

<400> SEQUENCE: 1
ctaaattgta agcgttaata ttttgttaaa attcgcgtta aatttttgtt aaatcagctc      60 atttttaac  caataggccg  aaatcggcaa  aatcccttat  aaatcaaaag  aatagaccga    120 gataggggttg agtgttgttc cagtttggaa caagagtcca ctattaaaga acgtggactc    180
caacgtcaaa gggcgaaaaa ccgtctatca gggcgatggc ccactacgtg aaccatcacc    240
ctaatcaagt tttttggggt cgaggtgccg taaagcacta atcggaacc ctaaagggag     300 cccccgattt agagcttgac ggggaaagcc ggcgaacgtg cgagaaagg aagggaagaa    360 agcgaaagga gcgggcgcta gggcgctggc aagtgtagcg gtcacgctgc gcgtaaccac    420
cacacccgcc gcgcttaatg cgccgctaca gggcgcgtcc cattcgccat tcaggctgcg    480
caactgttgg gaagggcgat cggtgcgggc ctcttcgcta ttacgccagc tggcgaaagg    540
gggatgtgct gcaaggcgat taagttgggt aacgccaggt tttcccagt cacgacgttg      600 taaacgacg gccagtgagc gcgcgtaata cgactcacta tagggcgaat tggagctcca    660
ccgcggtggc ggccgctcta gaactagtgg atccgtgtaa agtcactgct tttatagcta    720
catctgcata gatccctgt atgaaagcat gtactacctg gataataata tctgtatttt      780
tctgtagtag gaaatcagtg tagttttaa aaccaaaaag tattgttatt aatctatctt      840
tgatctcaaa caatttcaat gacctagtat agtgatttct acggaaagcc ctgcaattta     900
ctcaaagcag ttttaaata ttgttttaa agtgtgtgtg tgtgtgtgtg tgtgtgtgtg     960
tgtgtgtgtg gtgttaaagt cattttcaaa cccctcacaa tgtcttgaat gtgacatttg    1020
agtcatttat ggtaacttat aactccttg aagaagttat tcagaattga ggttccagac    1080
acacaaatgc acaatacacc atttttcctt ccagttaaca atcagagggc aacacttatt    1140
tttaaaggaa aatcgactcc ataagggact ttataaaggg gtagacataa accagtatca    1200
gggataaact ctccgttccc ctgtttaacc taattttccc agggccatcc tggaatacga    1260
attttctctt gaaatacagt caaagaaaaa gtggtaggct acagagcaga ggaaacactg    1320
gacacagcga cccacccccag agtcacttcc cttaatctaa tgactaggtt ttttctgaaa    1380
gttattttgt tagaacacag gaactttgc gaccacagtg atgctttag agggttgaat    1440 cctcaaaaag aaaattaatc gcaactagta gaagggagat tacttattga ttcttataac    1500
ttctgcagga atacacagtt atgagttagg gcaaagagaa aattgacttt taatattctc    1560
tatcactaac atgagagaac atgtatgtgt tccaaaataa ttttattta ttgaaaaccc    1620 gctatatacc tggattttca cagaatattc attactctcc aaaatggcct tttctaggtg    1680
aattttattt tccttacaga cctcaagaag tttacataat ttacttaaac ctgaggagag    1740
```

```
agaacaaagc ctcagaaaat ttacatagtt tatttaaact aaactcagct tgcttggtag    1800
cagcttctaa tcccagcagt taaagagaca gaagcagggc caacctgggg tataatataa    1860
ggtgagactc tccttcttt ctctctgtct ctgtctgtct ctgtctctgt gtgtgtgtgt    1920
gtgtgtgtgt gtgtgtgtgt gtgtctcctc tctctctctc tctctctctc tctctctctc    1980
tctgtctctc tctccctccc cctccctccc tctccccctc ctctctccct ccctctccct    2040 ccccccccc cacacatttg aattcgtgga gttggtaaat gaggggtcag ttctctgtct    2100
gtctgtagtt ttgtgtccac aggatatgac tgacattctc accacacaca tacaaagtca    2160
aaaatagctg tggccatata agaatatgg ggagagaaaa ttattcaaaa tctgcagaaa    2220
ataatgccag gcctttaatc ctggcaccca ggaggcagaa gggagacaga gttctgagtt    2280
tatgctgagt tccaggagtg gaagaaaggg ccattgcctt tctggtgagg actgtcttt    2340 taaatcctcc cttctgtcca gtactggtaa ctctgcccaa agcgtgttct tcttcctgcc    2400
tcacaagatt gcaaagacgt ttttaacgaa caatttaaac cggtgcaacg tttatgcgca    2460
gcacaccaac tcatttaaac aaacaacagc cccataaaat agaaatactt tataagcaga    2520
ttgccctccg atgacttcac cccgtcactt ttttatagtt gtgtacagaa tcctagcact    2580
gatacagcaa catcagaaat gtttctgcaa atccttcgca aagattcgga tttcatactg    2640
ggcgtggtac cctccaaaat gagttgtttg agctagggtt gttgggatct cagcttggcg    2700
aagttgtagc tctttcttct gaataaaaga tgacacaatt ttctgctaag atgttaaata    2760
ccttaagttt cagtgtagtg atgaaaatta ccctccttcg ttttctaat acctgggtgt    2820 tgcactgggg aggaaggaga gatttcgaga aggactagtt cactttctca gaagacacgt    2880
gtgcacttct ttgctgtgcg ggtccagaag gagcccagcg tgtcaaaggg tgaccaggca    2940
tgggggaggg gtgttagcgt gggtagcagg cggggctgt ccgatccttt agcgctgttt    3000
caacgcccag ctctcctcct gaaccctgca tctcttctgt agtccgggct ccatcccttt    3060
cccctccccc atccggaggt ggggggaaca gcagtgtttt caggggtgtt caattcatgc    3120
tatattcagg gcaaatagcg ccacctatgg cgggctgtgg agccaggtca ggagcagagt    3180
gtggctcccc ccccccccca caccatcctc agaggaagga aggagggacc cactggtcac    3240
acgactgggc gattgggcgg gcactgaatc tccgcgagga aagcgaactc gaggagagcc    3300
atcacgcgta gcatggggag tagcaagagc aagcctaagg accccagcca gcgctctaga    3360
ggcgtccaag tcgaaaccat tagtcccggc gatggcagaa catttcctaa aaggggacaa    3420
acatgtgtcg tccattatac aggcatgttg gaggacggca aaaaggtgga cagtagtaga    3480
gatcgcaata aacctttcaa attcatgttg ggaaaacaag aagtcattag gggatgggag    3540
gagggcgtgg ctcaaatgtc cgtcggccaa cgcgctaagc tcaccatcag ccccgactac    3600
gcatacggcg ctaccggaca tcccggaatt attccccctc acgctacctt ggtgtttgac    3660
gtcgaactgt tgaagctcga gactagagga gtgcaggtgg agactatctc cccaggagac    3720
gggcgcacct tccccaagcg cggccagacc tgcgtggtgc actacaccgg gatgcttgaa    3780
gatggaaaga aagttgattc ctcccgggac agaaacaagc cctttaagtt tatgctaggc    3840
aagcaggagg tgatccgagg ctgggaagaa ggggttgccc agatgagtgt gggtcagaga    3900
gccaaactga ctatatctcc agattatgcc tatggtgcca ctgggcaccc aggcatcatc    3960
ccaccacatg ccactctcgt cttcgatgtg gagcttctaa aactggaaac tagtagtgaa    4020
tcacagactt tggacaaagt ttaccaaatg aaaagcaaac ctcggggata ctgtctgatc    4080
atcaacaatc acaattttgc aaaagcacgg gagaaagtgc ccaaacttca cagcattagg    4140
```

```
gacaggaatg gaacacactt ggatgcaggg gctttgacca cgacctttga agagcttcat    4200
tttgagatca agccccacga tgactgcaca gtagagcaaa tctatgagat tttgaaaatc    4260
taccaactca tggaccacag taacatggac tgcttcatct gctgtatcct ctcccatgga    4320
gacaagggca tcatctatgg cactgatgga caggaggccc ccatctatga gctgacatct    4380
cagttcactg gtttgaagtg cccttccctt gctggaaaac ccaaagtgtt ttttattcag    4440
gcttgtcagg gggataacta ccagaaaggt atacctgttg agactgattc agaggagcaa    4500
ccctatttag aaatggattt atcatcacct caaacgagat atatcccgga tgaggctgac    4560
tttctgctgg ggatgccac tgtgaataac tgtgtttcct accgaaaccc tgcagaggga    4620
acctggtaca tccagtcact ttgccagagc ctgagagagc gatgtcctcg aggcgatgat    4680
attctcacca tcctgactga agtgaactat aagtaagca acaaggatga caagaaaaac    4740
atggggaaac agatgcctca gcctactttc acactaagaa aaaaacttgt cttcccttct    4800
gatgattaca aggatgacga cgataagtga ggatcaacct cgaggaattc acgcgtttaa    4860
ttaactcgag gttttcgagg tcgacggtat cgataagctt gatatcgaat tccgcccctc    4920 tcctccccc cccctaacg ttactggccg aagccgcttg gaataaggcc ggtgtgcgtt    4980
tgtctatatg ttattttcca ccatattgcc gtcttttggc aatgtgaggg cccggaaacc    5040
tggccctgtc ttcttgacga gcattcctag gggtctttcc cctctcgcca aggaatgca    5100 aggtctgttg aatgtcgtga aggaagcagt tcctctggaa gcttcttgaa gacaaacaac    5160
gtctgtagcg accctttgca ggcagcggaa ccccccacct ggcgacaggt gcctctgcgg    5220
ccaaaagcca cgtgtataag atacacctgc aaaggcggca caaccccagt gccacgttgt    5280
gagttggata gttgtggaaa gagtcaaatg gctctcctca agcgtattca acaaggggct    5340
gaaggatgcc cagaaggtac cccattgtat gggatctgat ctggggcctc ggtgcacatg    5400
ctttacatgt gtttagtcga ggttaaaaaa acgtctaggc cccccgaacc acggggacgt    5460
ggttttcctt tgaaaaacac gatgataata tggccacaac catggtgagc aagggcgagg    5520
agctgttcac cggggtggtg cccatcctgg tcgagctgga cggcgacgta acggccaca    5580 agttcagcgt gtccggcgag ggcgagggcg atgccaccta cggcaagctg accctgaagt    5640
tcatctgcac caccggcaag ctgcccgtgc cctggcccac cctcgtgacc accctgacct    5700
acggcgtgca gtgcttcagc cgctaccccg accacatgaa gcagcacgac ttcttcaagt    5760
ccgccatgcc cgaaggctac gtccaggagc gcaccatctt cttcaaggac gacggcaact    5820
acaagacccg cgccgaggtg aagttcgagg gcgacaccct ggtgaaccgc atcgagctga    5880
agggcatcga cttcaaggag gacggcaaca tcctggggca caagctggag tacaactaca    5940
acagccacaa cgtctatatc atggccgaca agcagaagaa cggcatcaag gtgaacttca    6000
agatccgcca caacatcgag gacggcagcg tgcagctcgc cgaccactac cagcagaaca    6060
cccccatcgg cgacggcccc gtgctgctgc ccgacaacca ctacctgagc acccagtccg    6120
ccctgagcaa agaccccaac gagaagcgcg atcacatggt cctgctggag ttcgtgaccg    6180
ccgccgggat cactctcggc atggacgagc tgtacaagta aagcggccgc gatcttttc    6240 cctctgccaa aaattatggg gacatcatga agccccttga gcatctgact tctggctaat    6300
aaaggaaatt tattttcatt gcaatagtgt gttggaattt tttgtgtctc tcactcggaa    6360
ggacatatgg gagggcaaat catttaaaac atcagaatga gtatttggtt tagagtttgg    6420
caacatatgc catatgctgg ctgccatgaa caaaggtggc tataaagagg tcatcagtat    6480
```

-continued

```
atgaaacagc cccctgctgt ccattcctta ttccatagaa aagccttgac ttgaggttag    6540
attttttta tattttgttt tgtgttattt ttttctttaa catccctaaa attttcctta    6600
catgttttac tagccagatt tttcctcctc tcctgactac tcccagtcat agctgtccct    6660
cttctcttat gaagatccct cgacctgcag cccaagcttg gcgtaatcat ggtcatagct    6720
gtttcctgtg tgaaattgtt atccgctcac aattccacac aacatacgag ccggaagcat    6780
aaagtgtaaa gcctggggtg cctaatgagt gagctaactc acattaattg cgttgcgctc    6840
actgcccgct ttccagtcgg gaaacctgtc gtgccagcgg atccgcatct caattagtca    6900
gcaaccatag tcccgcccct aactccgccc atcccgcccc taactccgcc cagttccgcc    6960
cattctccgc cccatggctg actaattttt tttatttatg cagaggccga ggccgcctaa    7020
acggccggcc atcgataccg tcgacctcga ggggggggccc ggtacccagc ttttgttccc    7080
tttagtgagg gttaattgcg cgcttggcgt aatcatggtc atagctgttt cctgtgtgaa    7140
attgttatcc gctcacaatt ccacacaaca tacgagccgg aagcataaag tgtaaagcct    7200
ggggtgccta atgagtgagc taactcacat taattgcgtt gcgctcactg cccgctttcc    7260
agtcgggaaa cctgtcgtgc cagctgcatt aatgaatcgg ccaacgcgcg gggagaggcg    7320
gtttgcgtat tgggcgctct tccgcttcct cgctcactga ctcgctgcgc tcggtcgttc    7380
ggctgcggcg agcggtatca gctcactcaa aggcggtaat acggttatcc acagaatcag    7440
gggataacgc aggaaagaac atgtgagcaa aaggccagca aaaggccagg aaccgtaaaa    7500
aggccgcgtt gctggcgttt ttccataggc tccgcccccc tgacgagcat cacaaaaatc    7560
gacgctcaag tcagaggtgg cgaaacccga caggactata aagataccag gcgtttcccc    7620
ctggaagctc cctcgtgcgc tctcctgttc cgaccctgcc gcttaccgga tacctgtccg    7680
cctttctccc ttcgggaagc gtggcgcttt ctcatagctc acgctgtagg tatctcagtt    7740
cggtgtaggt cgttcgctcc aagctgggct gtgtgcacga accccccgtt cagcccgacc    7800
gctgcgcctt atccggtaac tatcgtcttg agtccaaccc ggtaagacac gacttatcgc    7860
cactggcagc agccactggt aacaggatta gcagagcgag gtatgtaggc ggtgctacag    7920
agttcttgaa gtggtggcct aactacggct acactagaag gacagtattt ggtatctgcg    7980
ctctgctgaa gccagttacc ttcggaaaaa gagttggtag ctcttgatcc ggcaaacaaa    8040
ccaccgctgg tagcggtggt ttttttgttt gcaagcagca gattacgcgc agaaaaaaag    8100
gatctcaaga agatcctttg atcttttcta cggggtctga cgctcagtgg aacgaaaact    8160
cacgttaagg gattttggtc atgagattat caaaaaggat cttcacctag atccttttaa    8220
attaaaaatg aagttttaaa tcaatctaaa gtatatatga gtaaacttgg tctgacagtt    8280
accaatgctt aatcagtgag gcacctatct cagcgatctg tctatttcgt tcatccatag    8340
ttgcctgact ccccgtcgtg tagataacta cgatacggga gggcttacca tctggcccca    8400
gtgctgcaat gataccgcga gacccacgct caccggctcc agatttatca gcaataaacc    8460
agccagccgg aagggccgag cgcagaagtg gtcctgcaac tttatccgcc tccatccagt    8520
ctattaattg ttgccgggaa gctagagtaa gtagttcgcc agttaatagt ttgcgcaacg    8580
ttgttgccat tgctacaggc atcgtggtgt cacgctcgtc gtttggtatg gcttcattca    8640
gctccggttc ccaacgatca aggcgagtta catgatcccc catgttgtgc aaaaaagcgg    8700
ttagctcctt cggtcctccg atcgttgtca gaagtaagtt ggccgcagtg ttatcactca    8760
tggttatggc agcactgcat aattctctta ctgtcatgcc atccgtaaga tgcttttctg    8820
tgactggtga gtactcaacc aagtcattct gagaatagtg tatgcggcga ccgagttgct    8880
```

```
cttgcccggc gtcaatacgg gataataccg cgccacatag cagaacttta aaagtgctca    8940
tcattggaaa acgttcttcg gggcgaaaac tctcaaggat cttaccgctg ttgagatcca    9000
gttcgatgta acccactcgt gcacccaact gatcttcagc atctttact ttcaccagcg     9060 tttctgggtg agcaaaaaca ggaaggcaaa atgccgcaaa aagggaata agggcgacac     9120 ggaaatgttg aatactcata ctcttccttt tcaatatta ttgaagcatt tatcagggtt    9180
attgtctcat gagcggatac atatttgaat gtatttagaa aataaacaa ataggggttc     9240 cgcgcacatt tccccgaaaa gtgccac                                       9267
```

<210> SEQ ID NO 2
<211> LENGTH: 134
<212> TYPE: DNA
<213> ORGANISM: Artificial Sequence
<220> FEATURE:
<223> OTHER INFORMATION: Vector and Construct Component, 5' end

<400> SEQUENCE: 2

```
ctaaattgta agcgttaata ttttgttaaa attcgcgtta aattttgtt aaatcagctc     60 atttttaac caataggccg aaatcggcaa atcccttat aaatcaaaag aatagaccga    120
gatagggttg agtg                                                     134
```

<210> SEQ ID NO 3
<211> LENGTH: 325
<212> TYPE: DNA
<213> ORGANISM: Artificial Sequence
<220> FEATURE:
<223> OTHER INFORMATION: F1 ori

<400> SEQUENCE: 3

```
ttgttccagt ttggaacaag agtccactat taaagaacgt ggactccaac gtcaaagggc     60
gaaaaaccgt ctatcagggc gatggcccac tacgtgaacc atcaccctaa tcaagttttt   120
tggggtcgag gtgccgtaaa gcactaaatc ggaaccctaa agggagcccc cgatttagag   180
cttgacgggg aaagccggcg aacgtggcga gaaaggaagg gaagaaagcg aaaggagcgg   240
gcgctagggc gctggcaagt gtagcggtca cgctgcgcgt aaccaccaca cccgccgcgc   300
ttaatgcgcc gctacagggc gcgtc                                        325
```

<210> SEQ ID NO 4
<211> LENGTH: 139
<212> TYPE: DNA
<213> ORGANISM: Artificial Sequence
<220> FEATURE:
<223> OTHER INFORMATION: LacZ alpha

<400> SEQUENCE: 4

```
ccattcgcca ttcaggctgc gcaactgttg ggaagggcga tcggtgcggg cctcttcgct     60
attacgccag ctggcgaaag ggggatgtgc tgcaaggcga ttaagttggg taacgccagg   120
gttttcccag tcacgacgt                                                139
```

<210> SEQ ID NO 5
<211> LENGTH: 26
<212> TYPE: DNA
<213> ORGANISM: Artificial Sequence
<220> FEATURE:
<223> OTHER INFORMATION: M13 fwd

<400> SEQUENCE: 5

-continued

```
tgtaaaacga cggccagtga gcgcgc                                          26
```

<210> SEQ ID NO 6
<211> LENGTH: 65
<212> TYPE: DNA
<213> ORGANISM: Artificial Sequence
<220> FEATURE:
<223> OTHER INFORMATION: T7

<400> SEQUENCE: 6

```
gtaatacgac tcactatagg gcgaattgga gctccaccgc ggtggcggcc gctctagaac     60
tagtg                                                                65
```

<210> SEQ ID NO 7
<211> LENGTH: 5
<212> TYPE: DNA
<213> ORGANISM: Artificial Sequence
<220> FEATURE:
<223> OTHER INFORMATION: BAMH1, p16 promoter

<400> SEQUENCE: 7

```
gatcc                                                                 5
```

<210> SEQ ID NO 8
<211> LENGTH: 13
<212> TYPE: DNA
<213> ORGANISM: Artificial Sequence
<220> FEATURE:
<223> OTHER INFORMATION: forprimer3, p16 promoter

<400> SEQUENCE: 8

```
gtgtaaagtc act                                                        13
```

<210> SEQ ID NO 9
<211> LENGTH: 2604
<212> TYPE: DNA
<213> ORGANISM: Artificial Sequence
<220> FEATURE:
<223> OTHER INFORMATION: p16 promoter

<400> SEQUENCE: 9

```
cttttatagc tacatctgca tagatcccct gtatgaaagc atgtactacc tggataataa    60
tatctgtatt tttctgtagt aggaaatcag tgtagttttt aaaaccaaaa agtattgtta   120
ttaatctatc tttgatctca aacaatttca atgaccagtag atagtgattt ctacggaaag   180
ccctgcaatt tactcaaagc agttttttaaa tattgtttta aaagtgtgtg tgtgtgtgtg   240
tgtgtgtgtg tgtgtgtgtg tggtgttaaa gtcattttca aacccctcac aatgtcttga   300
atgtgacatt tgagtcattt atggtaactt ataactcctt tgaagaagtt attcagaatt   360
gaggttccag acacacaaat gcacaataca ccatttttcc ttccagttaa caatcagagg   420
gcaacactta ttttttaaagg aaaatcgact ccataaggga ctttataaag gggtagacat   480
aaaccagtat cagggataaa ctctccgttc cctgtttaa cctaattttc cagggccat    540 cctggaatac gaattttctc ttgaaataca gtcaagaaa agtggtagg ctacagagca    600 gaggaaacac tggacacagc gacccacccc agagtcactt cccttaatct aatgactagg   660 tttttctga aagttatttt gttagaacac aggaactttt gcgaccacag tgatgctttt   720
agagggttga atcctcaaaa agaaaattaa tcgcaactag tagaagggag attacttatt   780
gattcttata acttctgcag gaatacacag ttatgagtta gggcaaagag aaaattgact   840
tttaatattc tctatcacta acatgagaga acatgtatgt gttccaaaat aattttat     900
```

```
tattgaaaac ccgctatata cctggatttt cacagaatat tcattactct ccaaaatggc      960
cttttctagg tgaattttat tttccttaca gacctcaaga agtttacata atttacttaa     1020
acctgaggag agagaacaaa gcctcagaaa atttacatag tttatttaaa ctaaactcag     1080
cttgcttggt agcagcttct aatcccagca gttaaagaga cagaagcagg gccaacctgg     1140
ggtataatat aaggtgagac tctcctttct ttctctctgt ctctgtctgt ctctgtctct     1200
gtgtgtgtgt gtgtgtgtgt gtgtgtgtgt gtgtgtctcc tctctctctc tctctctctc     1260
tctctctctc tctctgtctc tctctcccct ccctccctc cctctccccc tcctctctcc      1320
ctccctctcc ctccccccc ccacacatt tgaattcgtg gagttggtaa atgagggtc        1380 agttctctgt ctgtctgtag ttttgtgtcc acaggatatg actgacattc tcaccacaca     1440
catacaaagt caaaaatagc tgtggccata taaagaatat ggggagagaa aattattcaa     1500
aatctgcaga aaataatgcc aggcctttaa tcctggcacc caggaggcag aagggagaca     1560
gagttctgag tttatgctga gttccaggag tggaagaaag ggccattgcc tttctggtga     1620
ggactgtctt tttaaatcct cccttctgtc cagtactggt aactctgccc aaagcgtgtt     1680
cttcttcctg cctcacaaga ttgcaaagac gtttttaacg aacaatttaa accggtgcaa     1740
cgtttatgcg cagcacacca actcatttaa acaaacaaca gccccataaa atagaaatac     1800
tttataagca gattgccctc cgatgacttc acccccgtcac tttttttatag ttgtgtacag    1860 aatcctagca ctgatacagc aacatcagaa atgtttctgc aaatccttcg caaagattcg     1920
gatttcatac tgggcgtggt accctccaaa atgagttgtt tgagctaggg ttgttgggat     1980
ctcagcttgg cgaagttgta gctctttctt ctgaataaaa gatgacacaa ttttctgcta     2040
agatgttaaa taccttaagt ttcagtgtag tgatgaaaat taccctcctt cgttttctca     2100
atacctgggt gttgcactgg ggaggaagga gagatttcga gaaggactag ttcactttct     2160
cagaagacac gtgtgcactt ctttgctgtg cgggtccaga aggagcccag cgtgtcaaag     2220
ggtgaccagg catgggggag gggtgttagc gtgggtagca ggcgggggct gtccgatcct     2280
ttagcgctgt ttcaacgccc agctctcctc ctgaaccctg catctcttct gtagtccggg     2340
ctccatccct ttcccctccc ccatccggag gtgggggaa cagcagtgtt ttcaggggtg      2400
ttcaattcat gctatattca gggcaaatag cgccacctat ggcgggctgt ggagccaggt     2460
caggagcaga gtgtggctcc ccccccccc cacaccatcc tcagaggaag aaggaggga      2520 cccactggtc acacgactgg gcgattgggc gggcactgaa tctccgcgag gaaagcgaac     2580
tcgaggagag ccatcacgcg tagc                                             2604
```

<210> SEQ ID NO 10
<211> LENGTH: 702
<212> TYPE: DNA
<213> ORGANISM: Artificial Sequence
<220> FEATURE:
<223> OTHER INFORMATION: FKBP

<400> SEQUENCE: 10

```
atggggagta gcaagagcaa gcctaaggac cccagccagc gctctagagg cgtccaagtc       60
gaaaccatta gtcccggcga tggcagaaca tttcctaaaa ggggacaaac atgtgtcgtc      120
cattatacag gcatgttgga ggacggcaaa aaggtggaca gtagtagaga tcgcaataaa      180
cctttcaaat tcatgttggg aaaacaagaa gtcattaggg gatgggagga gggcgtggct      240
caaatgtccg tcggccaacg cgctaagctc accatcagcc ccgactacgc atacggcgct      300
```

```
accggacatc ccggaattat tcccctcac gctaccttgg tgtttgacgt cgaactgttg    360
aagctcgaga ctagaggagt gcaggtggag actatctccc caggagacgg gcgcaccttc    420
cccaagcgcg gccagacctg cgtggtgcac tacaccggga tgcttgaaga tggaaagaaa    480
gttgattcct cccgggacag aaacaagccc tttaagttta tgctaggcaa gcaggaggtg    540
atccgaggct gggaagaagg ggttgcccag atgagtgtgg gtcagagagc caaactgact    600
atatctccag attatgccta tggtgccact gggcacccag gcatcatccc accacatgcc    660
actctcgtct tcgatgtgga gcttctaaaa ctggaaacta gt                      702
```

```
<210> SEQ ID NO 11
<211> LENGTH: 789
<212> TYPE: DNA
<213> ORGANISM: Artificial Sequence
<220> FEATURE:
<223> OTHER INFORMATION: Casp8

<400> SEQUENCE: 11
agtgaatcac agactttgga caaagtttac caaatgaaaa gcaaacctcg gggatactgt    60
ctgatcatca acaatcacaa ttttgcaaaa gcacgggaga agtgcccaa acttcacagc    120 attagggaca ggaatggaac acacttggat gcaggggctt tgaccacgac ctttgaagag    180
cttcattttg agatcaagcc ccacgatgac tgcacagtag agcaaatcta tgagattttg    240
aaaatctacc aactcatgga ccacagtaac atggactgct tcatctgctg tatcctctcc    300
catggagaca agggcatcat ctatggcact gatggacagg aggcccccat ctatgagctg    360
acatctcagt tcactggttt gaagtgccct tcccttgctg aaaacccaa agtgttttt    420 attcaggctt gtcagggggga taactaccag aaaggtatac ctgttgagac tgattcagag    480
gagcaaccct atttagaaat ggatttatca tcacctcaaa cgagatatat cccggatgag    540
gctgactttc tgctggggat ggccactgtg aataactgtg tttcctaccg aaaccctgca    600 gagggaaacct ggtacatcca gtcactttgc cagagcctga gagagcgatg tcctcgaggc    660
gatgatattc tcaccatcct gactgaagtg aactatgaag taagcaacaa ggatgacaag    720
aaaaacatgg ggaaacagat gcctcagcct actttcacac taagaaaaaa acttgtcttc    780
ccttctgat                                                          789
```

```
<210> SEQ ID NO 12
<211> LENGTH: 27
<212> TYPE: DNA
<213> ORGANISM: Artificial Sequence
<220> FEATURE:
<223> OTHER INFORMATION: Flag/Tag/Stop

<400> SEQUENCE: 12
gattacaagg atgacgacga taagtga                                       27
```

```
<210> SEQ ID NO 13
<211> LENGTH: 5
<212> TYPE: DNA
<213> ORGANISM: Artificial Sequence
<220> FEATURE:
<223> OTHER INFORMATION: 3' UTR

<400> SEQUENCE: 13 ggatc                                                               5
```

```
<210> SEQ ID NO 14
<211> LENGTH: 39
```

<212> TYPE: DNA
<213> ORGANISM: Artificial Sequence
<220> FEATURE:
<223> OTHER INFORMATION: Multiple cloning site (MluI, PacI, XhoI, PmeI)

<400> SEQUENCE: 14

```
aacctcgagg aattcacgcg tttaattaac tcgaggttt                              39
```

<210> SEQ ID NO 15
<211> LENGTH: 1268
<212> TYPE: DNA
<213> ORGANISM: Artificial Sequence
<220> FEATURE:
<223> OTHER INFORMATION: IRES, GFP

<400> SEQUENCE: 15

```
tcgaggtcga cggtatcgat aagcttgata tcgaattccg cccctctccc tcccccccc      60
ctaacgttac tggccgaagc cgcttggaat aaggccggtg tgcgtttgtc tatatgttat    120
tttccaccat attgccgtct tttggcaatg tgagggcccg gaaacctggc cctgtcttct    180
tgacgagcat tcctaggggt cttccctctc tcgccaaagg aatgcaaggt ctgttgaatg    240
tcgtgaagga agcagttcct ctggaagctt cttgaagaca acaacgtct gtagcgaccc     300
tttgcaggca gcggaacccc ccacctggcg acaggtgcct ctgcggccaa aagccacgtg    360
tataagatac acctgcaaag gcggcacaac cccagtgcca cgttgtgagt tggatagttg    420
tggaaagagt caaatggctc tcctcaagcg tattcaacaa ggggctgaag gatgcccaga    480
aggtacccca ttgtatggga tctgatctgg ggcctcggtg cacatgcttt acatgtgttt    540
agtcgaggtt aaaaaaacgt ctaggcccccc cgaaccacgg ggacgtggtt ttcctttgaa   600
aaacacgatg ataatatggc cacaaccatg gtgagcaagg gcgaggagct gttcaccggg    660
gtggtgccca tcctggtcga gctggacggc gacgtaaacg gccacaagtt cagcgtgtcc    720
ggcgagggcg agggcgatgc cacctacggc aagctgaccc tgaagttcat ctgcaccacc    780
ggcaagctgc ccgtgccctg gcccaccctc gtgaccaccc tgacctacgg cgtgcagtgc    840
ttcagccgct accccgacca catgaagcag cacgacttct tcaagtccgc catgcccgaa    900
ggctacgtcc aggagcgcac catcttcttc aaggacgacg gcaactacaa gacccgcgcc    960
gaggtgaagt tcgagggcga caccctggtg aaccgcatcg agctgaaggg catcgacttc   1020
aaggaggacg gcaacatcct ggggcacaag ctggagtaca actacaacag ccacaacgtc   1080
tatatcatgg ccgacaagca gaagaacggc atcaaggtga acttcaagat ccgccacaac   1140
atcgaggacg gcagcgtgca gctcgccgac cactaccagc agaacacccc catcggcgac   1200
ggccccgtgc tgctgcccga caaccactac ctgagcaccc agtccgccct gagcaaagac   1260
cccaacga                                                            1268
```

<210> SEQ ID NO 16
<211> LENGTH: 565
<212> TYPE: DNA
<213> ORGANISM: Artificial Sequence
<220> FEATURE:
<223> OTHER INFORMATION: Rabbit beta-globin PA

<400> SEQUENCE: 16

```
gaagcgcgat cacatggtcc tgctggagtt cgtgaccgcc gccgggatca ctctcggcat     60
ggacgagctg tacaagtaaa gcggccgcga tcttttttcc tctgccaaaa attatgggga   120
catcatgaag ccccttgagc atctgacttc tggctaataa aggaaattta ttttcattgc   180
```

```
aatagtgtgt tggaattttt tgtgtctctc actcggaagg acatatggga gggcaaatca    240
tttaaaacat cagaatgagt atttggttta gagtttggca acatatgcca tatgctggct    300
gccatgaaca aggtggcta taaagaggtc atcagtatat gaaacagccc cctgctgtcc     360
attccttatt ccatagaaaa gccttgactt gaggttagat tttttttata ttttgttttg    420
tgttattttt ttctttaaca tccctaaaat tttccttaca tgttttacta gccagatttt    480
tcctcctctc ctgactactc ccagtcatag ctgtccctct tctcttatga agatccctcg    540
acctgcagcc caagcttggc gtaat                                          565
```

<210> SEQ ID NO 17
<211> LENGTH: 26
<212> TYPE: DNA
<213> ORGANISM: Artificial Sequence
<220> FEATURE:
<223> OTHER INFORMATION: M13-rev

<400> SEQUENCE: 17

```
catggtcata gctgtttcct gtgtga                                          26
```

<210> SEQ ID NO 18
<211> LENGTH: 285
<212> TYPE: DNA
<213> ORGANISM: Artificial Sequence
<220> FEATURE:
<223> OTHER INFORMATION: LacO

<400> SEQUENCE: 18

```
aattgttatc cgctcacaat tccacacaac atacgagccg gaagcataaa gtgtaaagcc    60
tggggtgcct aatgagtgag ctaactcaca ttaattgcgt tgcgctcact gcccgctttc   120
cagtcgggaa acctgtcgtg ccagcggatc cgcatctcaa ttagtcagca accatagtcc   180
cgcccctaac tccgcccatc ccgcccctaa ctccgcccag ttccgcccat tctccgcccc   240
atggctgact aatttttttt atttatgcag aggccgaggc cgcct                   285
```

<210> SEQ ID NO 19
<211> LENGTH: 58
<212> TYPE: DNA
<213> ORGANISM: Artificial Sequence
<220> FEATURE:
<223> OTHER INFORMATION: Fse1, linker

<400> SEQUENCE: 19

```
aaacggccgg ccatcgatac cgtcgacctc gagggggggc ccggtaccca gcttttgt      58
```

<210> SEQ ID NO 20
<211> LENGTH: 37
<212> TYPE: DNA
<213> ORGANISM: Artificial Sequence
<220> FEATURE:
<223> OTHER INFORMATION: T3

<400> SEQUENCE: 20

```
tccctttagt gagggttaat tgcgcgcttg gcgtaat                              37
```

<210> SEQ ID NO 21
<211> LENGTH: 26
<212> TYPE: DNA
<213> ORGANISM: Artificial Sequence
<220> FEATURE:
<223> OTHER INFORMATION: M13-rev

<400> SEQUENCE: 21
catggtcata gctgtttcct gtgtga                                          26

<210> SEQ ID NO 22
<211> LENGTH: 362
<212> TYPE: DNA
<213> ORGANISM: Artificial Sequence
<220> FEATURE:
<223> OTHER INFORMATION: LacO

<400> SEQUENCE: 22
aattgttatc cgctcacaat tccacacaac atacgagccg aagcataaa gtgtaaagcc      60 tggggtgcct aatgagtgag ctaactcaca ttaattgcgt tgcgctcact gcccgctttc    120
cagtcgggaa acctgtcgtg ccagctgcat taatgaatcg gccaacgcgc ggggagaggc    180
ggtttgcgta ttgggcgctc ttccgcttcc tcgctcactg actcgctgcg ctcggtcgtt    240
cggctgcggc gagcggtatc agctcactca aaggcggtaa tacggttatc cacagaatca    300
ggggataacg caggaaagaa catgtgagca aaaggccagc aaaaggccag gaaccgtaaa    360
aa                                                                   362

<210> SEQ ID NO 23
<211> LENGTH: 780
<212> TYPE: DNA
<213> ORGANISM: Artificial Sequence
<220> FEATURE:
<223> OTHER INFORMATION: ColE1 origin

<400> SEQUENCE: 23
ggccgcgttg ctggcgtttt tccataggct ccgcccccct gacgagcatc acaaaaatcg     60
acgctcaagt cagaggtggc gaaacccgac aggactataa agataccagg cgtttccccc    120
tggaagctcc ctcgtgcgct ctcctgttcc gaccctgccg cttaccggat acctgtccgc    180
ctttctccct tcgggaagcg tggcgctttc tcatagctca cgctgtaggt atctcagttc    240
ggtgtaggtc gttcgctcca agctgggctg tgtgcacgaa ccccccgttc agcccgaccg    300
ctgcgcctta tccggtaact atcgtcttga gtccaacccg gtaagacacg acttatcgcc    360
actggcagca gccactggta acaggattag cagagcgagg tatgtaggcg gtgctacaga    420
gttcttgaag tggtggccta actacggcta cactagaagg acagtatttg gtatctgcgc    480
tctgctgaag ccagttacct tcggaaaaag agttggtagc tcttgatccg gcaaacaaac    540
caccgctggt agcggtggtt tttttgtttg caagcagcag attacgcgca gaaaaaaagg    600
atctcaagaa gatcctttga tcttttctac ggggtctgac gctcagtgga acgaaaactc    660
acgttaaggg attttggtca tgagattatc aaaaaggatc ttcacctaga tccttttaaa    720
ttaaaaatga agttttaaat caatctaaag tatatatgag taaacttggt ctgacagtta    780

<210> SEQ ID NO 24
<211> LENGTH: 986
<212> TYPE: DNA
<213> ORGANISM: Artificial Sequence
<220> FEATURE:
<223> OTHER INFORMATION: AmpR

<400> SEQUENCE: 24
ccaatgctta atcagtgagg cacctatctc agcgatctgt ctatttcgtt catccatagt     60
tgcctgactc cccgtcgtgt agataactac gatacgggag ggcttaccat ctggccccag    120
tgctgcaatg ataccgcgag acccacgctc accggctcca gatttatcag caataaacca    180

| | |
|---|---|
| gccagccgga agggccgagc gcagaagtgg tcctgcaact ttatccgcct ccatccagtc | 240 |
| tattaattgt tgccgggaag ctagagtaag tagttcgcca gttaatagtt tgcgcaacgt | 300 |
| tgttgccatt gctacaggca tcgtggtgtc acgctcgtcg tttggtatgg cttcattcag | 360 |
| ctccggttcc caacgatcaa ggcgagttac atgatccccc atgttgtgca aaaaagcggt | 420 |
| tagctccttc ggtcctccga tcgttgtcag aagtaagttg gccgcagtgt tatcactcat | 480 |
| ggttatggca gcactgcata attctcttac tgtcatgcca ccgtaagat gcttttctgt | 540 |
| gactggtgag tactcaacca agtcattctg agaatagtgt atgcggcgac cgagttgctc | 600 |
| ttgcccggcg tcaatacggg ataataccgc gccacatagc agaactttaa aagtgctcat | 660 |
| cattggaaaa cgttcttcgg ggcgaaaact ctcaaggatc ttaccgctgt tgagatccag | 720 |
| ttcgatgtaa cccactcgtg cacccaactg atcttcagca tcttttactt tcaccagcgt | 780 |
| ttctgggtga gcaaaaacag gaaggcaaaa tgccgcaaaa agggaataa gggcgacacg | 840 |
| gaaatgttga atactcatac tcttcctttt tcaatattat tgaagcattt atcagggtta | 900 |
| ttgtctcatg agcggataca tatttgaatg tatttagaaa aataaacaaa tagggggttcc | 960 |
| gcgcacattt ccccgaaaag tgccac | 986 |

<210> SEQ ID NO 25
<211> LENGTH: 18
<212> TYPE: DNA
<213> ORGANISM: Artificial Sequence
<220> FEATURE:
<223> OTHER INFORMATION: Tubulin-A forward primer

<400> SEQUENCE: 25
cttcgtctcc gccatcag                                                    18

<210> SEQ ID NO 26
<211> LENGTH: 18
<212> TYPE: DNA
<213> ORGANISM: Artificial Sequence
<220> FEATURE:
<223> OTHER INFORMATION: Tubulin-A reverse primer

<400> SEQUENCE: 26
ttgccaatct ggacacca                                                    18

<210> SEQ ID NO 27
<211> LENGTH: 21
<212> TYPE: DNA
<213> ORGANISM: Artificial Sequence
<220> FEATURE:
<223> OTHER INFORMATION: IL-6 forward primer

<400> SEQUENCE: 27
gcccagctat gaactccttc t                                                21

<210> SEQ ID NO 28
<211> LENGTH: 18
<212> TYPE: DNA
<213> ORGANISM: Artificial Sequence
<220> FEATURE:
<223> OTHER INFORMATION: IL-6 reverse primer

<400> SEQUENCE: 28
gaaggcagca ggcaacac                                                    18

<210> SEQ ID NO 29
<211> LENGTH: 20

-continued

```
<212> TYPE: DNA
<213> ORGANISM: Artificial Sequence
<220> FEATURE:
<223> OTHER INFORMATION: IL-8 forward primer

<400> SEQUENCE: 29
agacagcaga gcacacaagc                                              20

<210> SEQ ID NO 30
<211> LENGTH: 18
<212> TYPE: DNA
<213> ORGANISM: Artificial Sequence
<220> FEATURE:
<223> OTHER INFORMATION: IL-8 reverse primer

<400> SEQUENCE: 30
atggttcctt ccggtggt                                                18

<210> SEQ ID NO 31
<211> LENGTH: 27
<212> TYPE: DNA
<213> ORGANISM: Artificial Sequence
<220> FEATURE:
<223> OTHER INFORMATION: MMP-3 foward primer

<400> SEQUENCE: 31
caaaacatat ttctttgtag aggacaa                                      27

<210> SEQ ID NO 32
<211> LENGTH: 21
<212> TYPE: DNA
<213> ORGANISM: Artificial Sequence
<220> FEATURE:
<223> OTHER INFORMATION: MMP-3 reverse primer

<400> SEQUENCE: 32
ttcagctatt tgcttgggaa a                                            21

<210> SEQ ID NO 33
<211> LENGTH: 18
<212> TYPE: DNA
<213> ORGANISM: Artificial Sequence
<220> FEATURE:
<223> OTHER INFORMATION: GR forward primer

<400> SEQUENCE: 33
gaaagccacg ctcccttc                                                18

<210> SEQ ID NO 34
<211> LENGTH: 25
<212> TYPE: DNA
<213> ORGANISM: Artificial Sequence
<220> FEATURE:
<223> OTHER INFORMATION: GR reverse primer

<400> SEQUENCE: 34
agacttaggt gaaactggaa ttgct                                        25

<210> SEQ ID NO 35
<211> LENGTH: 21
<212> TYPE: DNA
<213> ORGANISM: Artificial Sequence
<220> FEATURE:
<223> OTHER INFORMATION: IL-1alpha forward primer

<400> SEQUENCE: 35
```

```
ggttgagttt aagccaatcc a                                              21

<210> SEQ ID NO 36
<211> LENGTH: 20
<212> TYPE: DNA
<213> ORGANISM: Artificial Sequence
<220> FEATURE:
<223> OTHER INFORMATION: IL-1alpha reverse primer

<400> SEQUENCE: 36
tgctgaccta ggcttgatga                                                20

<210> SEQ ID NO 37
<211> LENGTH: 20
<212> TYPE: DNA
<213> ORGANISM: Artificial Sequence
<220> FEATURE:
<223> OTHER INFORMATION: IkappaBalpha forward primer

<400> SEQUENCE: 37
ggtgctgatg tcaatgctca                                                20

<210> SEQ ID NO 38
<211> LENGTH: 18
<212> TYPE: DNA
<213> ORGANISM: Artificial Sequence
<220> FEATURE:
<223> OTHER INFORMATION: IkappaBalpha reverese primer

<400> SEQUENCE: 38
acaccaggtc aggatttt                                                  18
```